United States Patent
Moon et al.

(10) Patent No.: US 6,858,842 B2
(45) Date of Patent: *Feb. 22, 2005

(54) ELECTROSPRAY NOZZLE AND MONOLITHIC SUBSTRATE

(75) Inventors: James E. Moon, Ithaca, NY (US); Timothy J. Davis, Trumansburg, NY (US); Gregory J. Galvin, Ithaca, NY (US); Gary A. Schultz, Ithaca, NY (US); Thomas N. Corso, Freeville, NY (US); Stephen Lowes, Freeville, NY (US)

(73) Assignees: Advion Biosciences, Inc., Ithaca, NY (US); Kionix, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/814,207

(22) Filed: Mar. 31, 2004

(65) Prior Publication Data

US 2004/0182818 A1 Sep. 23, 2004

Related U.S. Application Data

(60) Continuation of application No. 10/771,553, filed on Feb. 4, 2004, which is a continuation of application No. 09/702,955, filed on Oct. 31, 2000, now Pat. No. 6,780,313, which is a division of application No. 09/156,507, filed on Sep. 17, 1998, now abandoned.

(51) Int. Cl.[7] .......................... H01J 49/04; H01J 49/10; B01D 59/44
(52) U.S. Cl. .................... 250/288; 250/282; 250/281; 210/198.2; 210/243; 210/656; 210/748
(58) Field of Search ................................. 250/288, 281, 250/282; 210/198.2, 656, 243; 204/453, 452, 451

(56) References Cited

U.S. PATENT DOCUMENTS

| 3,150,442 A | 9/1964 | Straw et al. |
|---|---|---|
| 3,538,744 A | 11/1970 | Karasek |
| 3,586,933 A | 6/1971 | Bonini |
| 3,611,071 A | 10/1971 | Agusta |
| 3,663,194 A | 5/1972 | Greenstein et al. |

(List continued on next page.)

FOREIGN PATENT DOCUMENTS

| DE | 43 18 407 | 12/1994 |
|---|---|---|
| EP | 677322 | 10/1995 |

(List continued on next page.)

OTHER PUBLICATIONS

Amish Desai; Yu–Chong Tai; Michael T. Davis; and, Terry D. Lee, "A MEMS Electrospray Nozzle for Mass Spectroscopy," 1997 International Conference in Solid–State Sensors and Actuators, Chicago, Jun. 16–19, 1997, pp. 927–930.

(List continued on next page.)

*Primary Examiner*—Nikita Wells
*Assistant Examiner*—Johnnie L Smith, II
(74) *Attorney, Agent, or Firm*—Holme Roberts & Owen LLP

(57) ABSTRACT

An electrospray nozzle system is disclosed. The electrospray portion of the device comprises a substrate defining a channel between an entrance orifice on an injection surface and an exit orifice on an ejection surface, a nozzle defined by a portion recessed from the ejection surface surrounding the exit orifice, and an electrode for application of an electric potential to the substrate to optimize and generate an electrospray; and, optionally, additional electrode(s) to further modify the electrospray. The nozzle system may be utilized alone or as part of a liquid chromatography system.

5 Claims, 26 Drawing Sheets

U.S. PATENT DOCUMENTS

| | | |
|---|---|---|
| 3,669,881 A | 6/1972 | Cremer et al. |
| 3,725,186 A | 4/1973 | Lynch |
| 3,738,759 A | 6/1973 | Dittrich et al. |
| 3,770,405 A | 11/1973 | DeAngelis et al. |
| 3,915,652 A | 10/1975 | Natelson |
| 3,921,961 A | 11/1975 | Bassous |
| 3,940,301 A | 2/1976 | Straw et al. |
| 4,007,464 A | 2/1977 | Bassous et al. |
| 4,056,324 A | 11/1977 | Gohde |
| 4,092,166 A | 5/1978 | Olsen et al. |
| 4,209,696 A | 6/1980 | Fite |
| 4,356,722 A | 11/1982 | Bunce et al. |
| 4,366,118 A | 12/1982 | Bunce et al. |
| 4,369,664 A | 1/1983 | Bunce et al. |
| 4,403,234 A | 9/1983 | Miura et al. |
| 4,437,103 A | 3/1984 | Ikeda |
| 4,459,267 A | 7/1984 | Bunce et al. |
| 4,480,259 A | 10/1984 | Kruger et al. |
| 4,489,259 A | 12/1984 | White et al. |
| 4,490,728 A | 12/1984 | Vaught et al. |
| 4,590,482 A | 5/1986 | Hay et al. |
| 4,593,728 A | 6/1986 | Whitehead et al. |
| 4,683,042 A | 7/1987 | Scott |
| 4,708,782 A | 11/1987 | Andresen et al. |
| 4,728,392 A | 3/1988 | Miura et al. |
| 4,733,823 A | 3/1988 | Waggener et al. |
| 4,842,701 A | 6/1989 | Smith et al. |
| 4,879,097 A | 11/1989 | Whitehead et al. |
| 4,891,120 A | 1/1990 | Sethi et al. |
| 4,908,112 A | 3/1990 | Pace |
| 4,983,038 A | 1/1991 | Ohki et al. |
| 4,999,493 A | 3/1991 | Allen et al. |
| 5,015,845 A | 5/1991 | Allen et al. |
| 5,110,745 A | 5/1992 | Kricka et al. |
| 5,126,022 A | 6/1992 | Soane et al. |
| 5,132,012 A | 7/1992 | Miura et al. |
| 5,162,650 A | 11/1992 | Bier |
| 5,180,480 A | 1/1993 | Manz |
| 5,182,366 A | 1/1993 | Huebner et al. |
| 5,245,185 A | 9/1993 | Busch et al. |
| 5,269,900 A | 12/1993 | Jorgenson et al. |
| 5,283,036 A | 2/1994 | Hofmann et al. |
| 5,294,426 A | 3/1994 | Sekine et al. |
| 5,296,114 A | 3/1994 | Manz |
| 5,296,375 A | 3/1994 | Kricka et al. |
| 5,302,533 A | 4/1994 | Kricka |
| 5,304,487 A | 4/1994 | Wilding et al. |
| 5,306,621 A | 4/1994 | Kricka |
| 5,316,680 A | 5/1994 | Frechet et al. |
| 5,328,578 A | 7/1994 | Gordon |
| 5,331,159 A | 7/1994 | Apffel, Jr. et al. |
| 5,332,481 A | 7/1994 | Guttman |
| 5,334,310 A | 8/1994 | Frechet et al. |
| 5,338,427 A | 8/1994 | Shartle et al. |
| 5,349,186 A | 9/1994 | Ikonomou et al. |
| 5,374,834 A | 12/1994 | Geis et al. |
| 5,376,252 A | 12/1994 | Ekstrom et al. |
| 5,387,329 A | 2/1995 | Foos et al. |
| 5,401,376 A | 3/1995 | Foos et al. |
| 5,401,963 A | 3/1995 | Sittler |
| 5,415,841 A | 5/1995 | Dovichi et al. |
| 5,421,980 A | 6/1995 | Guttman |
| 5,423,964 A | 6/1995 | Smith et al. |
| 5,427,946 A | 6/1995 | Kricka et al. |
| 5,429,734 A | 7/1995 | Gajar et al. |
| 5,431,807 A | 7/1995 | Frechet et al. |
| 5,445,324 A | 8/1995 | Berry et al. |
| 5,453,185 A | 9/1995 | Frechet et al. |
| 5,481,110 A | 1/1996 | Krishnaswamy et al. |
| 5,486,335 A | 1/1996 | Wilding et al. |
| 5,493,115 A | 2/1996 | Deinzer et al. |
| 5,495,108 A | 2/1996 | Apffel, Jr. et al. |
| 5,498,392 A | 3/1996 | Wilding et al. |
| 5,501,883 A | 3/1996 | Ishikawa et al. |
| 5,501,893 A | 3/1996 | Laermer et al. |
| 5,505,832 A | 4/1996 | Laukien et al. |
| 5,512,131 A | 4/1996 | Kumar et al. |
| 5,512,451 A | 4/1996 | Kricka |
| 5,523,566 A | 6/1996 | Fuerstenau et al. |
| 5,536,939 A | 7/1996 | Freidhoff et al. |
| 5,541,408 A | 7/1996 | Sittler |
| 5,563,639 A | 10/1996 | Cameron et al. |
| 5,572,023 A | 11/1996 | Caprioli |
| 5,608,217 A | 3/1997 | Franzen et al. |
| 5,640,010 A | 6/1997 | Twerenbold |
| 5,641,400 A | 6/1997 | Kaltenbach et al. |
| 5,644,131 A | 7/1997 | Hansen |
| 5,647,979 A | 7/1997 | Liao et al. |
| 5,652,427 A | 7/1997 | Whitehouse et al. |
| 5,705,813 A | 1/1998 | Apffel et al. |
| 5,716,825 A | 2/1998 | Hancock et al. |
| 5,747,815 A | 5/1998 | Young et al. |
| 5,750,988 A | 5/1998 | Apffel et al. |
| 5,779,868 A | 7/1998 | Parce et al. |
| 5,789,746 A | 8/1998 | Kato et al. |
| 5,800,692 A | 9/1998 | Naylor et al. |
| 5,804,022 A | 9/1998 | Kaltenbach et al. |
| 5,856,082 A | 1/1999 | Aebersold et al. |
| 5,872,010 A | 2/1999 | Karger et al. |
| 5,876,957 A | 3/1999 | Douglas et al. |
| 5,877,495 A | 3/1999 | Takada et al. |
| 5,917,184 A | 6/1999 | Carson et al. |
| 5,917,185 A | 6/1999 | Yeung et al. |
| 5,969,351 A | 10/1999 | Nabeshima et al. |
| 5,969,353 A | 10/1999 | Hsieh |
| 5,972,187 A | 10/1999 | Parce et al. |
| 5,993,633 A | 11/1999 | Smith et al. |
| 5,994,696 A | 11/1999 | Tai et al. |
| 6,005,245 A | 12/1999 | Sakairi et al. |
| 6,007,775 A | 12/1999 | Yager |
| 6,032,876 A | 3/2000 | Bertsch et al. |
| 6,060,705 A | 5/2000 | Whitehouse et al. |
| 6,066,848 A | 5/2000 | Kassel et al. |
| 6,068,749 A | 5/2000 | Karger et al. |
| 6,110,343 A | 8/2000 | Ramsey et al. |
| 6,114,693 A | 9/2000 | Hirabayashi et al. |
| 6,171,875 B1 | 1/2001 | Silverbrook |
| 6,245,227 B1 * | 6/2001 | Moon et al. ............. 210/198.2 |
| 6,394,942 B2 | 5/2002 | Moon et al. |
| 6,417,510 B2 | 7/2002 | Moon et al. |
| 6,454,938 B2 * | 9/2002 | Moon et al. ............. 210/198.2 |
| 6,563,111 B1 * | 5/2003 | Moon et al. ................ 250/288 |
| 6,569,324 B1 * | 5/2003 | Moon et al. ............. 210/198.2 |
| 2001/0001452 A1 | 5/2001 | Davis et al. |
| 2001/0001455 A1 | 5/2001 | Davis et al. |
| 2001/0001456 A1 | 5/2001 | Davis et al. |
| 2001/0001460 A1 | 5/2001 | Davis et al. |
| 2001/0001474 A1 | 5/2001 | Davis et al. |

FOREIGN PATENT DOCUMENTS

| | | |
|---|---|---|
| EP | 259796 | 1/1996 |
| EP | 692713 | 1/1996 |
| EP | 637998 | 7/1996 |
| EP | 639223 | 7/1996 |
| EP | 565027 | 3/1997 |
| EP | 860858 | 8/1998 |
| EP | 588952 | 9/1999 |
| EP | 0 964428 A2 | 12/1999 |
| EP | 0 966022 A2 | 12/1999 |
| GB | 2 260 282 | 4/1993 |
| GB | 2287356 | 9/1995 |

| WO | WO 92/03720 | 3/1992 |
| WO | WO 93/22053 | 11/1993 |
| WO | WO 93/22055 | 11/1993 |
| WO | WO 96/04547 | 2/1996 |
| WO | WO 96/14933 | 5/1996 |
| WO | WO 96/14934 | 5/1996 |
| WO | WO 96/15269 | 5/1996 |
| WO | WO 97/04297 | 2/1997 |
| WO | WO 00/52455 | 9/2000 |
| WO | PCT/US00/34999 | 7/2001 |
| WO | PCT/US01/01785 | 7/2001 |
| WO | WO 01/50499 | 7/2001 |
| WO | WO 0153819 | 7/2001 |

OTHER PUBLICATIONS

Andren, Per E., et al., "Micro–Electrospray: Zeptomole/Attomole per Microliter Sensitivity for Peptides," 1994, American Society for Mass Spectrometry, pp. 867–869.

Angell, James B., et al., "Silicon Micromechanical Devices," 1983, Scientific American, pp. 44–55.

Beavis, R.C., et al., "Off–Line Coupling of a Microbore High–Performance Liquid Chromatograph to a Secondary Ion–Time of Flight Mass Spectrometer," 1990, Analytical Chemistry, pp. 1259–1264.

Beavis, Ronald C., et al., "Automated Dry Fraction Collection for Microbore High–Performance Liquid Chromatography–Mass Spectrometry," 1986, Journal of Chromatography, 359, pp. 489–497.

Bing He, Niall Talt, Fred Regnier, "Fabrication on Nanocolumns for Liquid Chromatography," Analytical Chemistry, vol. 70, No. 18, Sep., 1998, pp. 3790–3797.

Bruggrat, Norbert, et al., "Synchronized Cyclic Capillary Electrophoresis—A Novel Approach to Ion Separations in Solution", Oct., 1993, Journal of High Resolution Chromatography, vol. 16, pp. 594–596.

Cheng, Jing, et al., "Chip PCR.II. Investigation of Different PCR Amplification Systems in Microfabricated Silicon–Glass Chips," 1996, Nucleic Acids Research, vol. 24, No. 2, pp. 380–385.

Chu, Yen–Ho, et al., "Affinity Capillary Electrophoresis–Mass Spectrometry for Screening Cominatorial Libraries," 1996, Journal of the American Chemical Society, pp. 7827–7835.

Cowan, S., et al., "An On–Chip Miniatrure Liquid Chromatography System: Design, Construction and Characterization" 1995, Micro Total Analysis Systems, pp. 295–298.

D. Figeys, et al., Analytical Chemistry, vol. 69, Aug. 1977, pp. 3153–3160.

D. Jed Harrison; Karl Fluri; Kurt Seiler; Zhonghui Fan; Carlo S. Effenhauser; and, Andreas Manz, "Micromachining a Miniaturized Capillary Electrophoresis–Based Chemical Analysis System on a Chip," Science, vol. 261, Aug. 1993, 895–897.

David C. Gale and Richard D. Smith, "Small Volume and Low Flow–rate Electrospray Ionization Mass Spectrometry of Aqueous Samples," Rapid Communications in Mass Spectrometry, vol. 7, Sep., 1993, pp. 1017–1021.

David P. H. Smith, "The Electrohydrodynamic Atomization of Liquids," IEEE Transactions on Industry Applications, vol. IA–22, No. 3, pp. 572–535, May–Jun., 1986.

Davis, Michael T., et al., "A Microscale Electrospray Interface for On–Line, Capillary Liquid Chromatography/Tandem Mass Spectrometry of Complex Peptide Mixtures," 1995, Analytical Chemistry, 67, pp. 4549–4556.

Deml, M., et al., "Electric Sampler Splitter for Capillary Zone Electrophoresis," 1985, Journal of Chromatography, 320, pp. 159–165.

Doherty, Steven J., et al., "Rapid On–Line Analysis Using a Micromachined Gas Chromatograph Coupled to a Bench–Top Quadrupole Mass Spectrometer" 1994, LC–GC vol. 12, No. 11, pp. 846–850.

Effenhauser, Carlo S., et al, "Manipulation of Sample Fractions on a Capillary Electrophoresis Chip," Jul. 1, 1995, Analytical Chemistry, vol. 67, No. 13, pp. 2284–2287.

Effenhauser, Carlo S., et al., "Glass Chips for High–Speed Capillary Electrophoresis Separations with Submicrometer Plate Height," 1993, Analytical Chemistry, 65, pp. 2637–2642.

Effenhauser, Carol S., et al., "High–Speed Separation of Antisense Oligonucleotides on a Micromachined Capillary Electrophoresis Device," 1994, Analytical Chemistry, 66, pp. 2949–2953.

Elwenspoek, M., et al., "Silicon Microstructures for Fluid Handling," 1994, Analysis Magazine, pp. 1–4.

Emmett, Mark R., et al., "Micro–Electrospray Mass Spectrometry; Ultra–High–Sensitivity Analysis of Peptides and Proteins," 1994, American Society for Mass Specrometry, pp. 605–613.

Fan, Zhonghul H., et al., "Micromachining of Capillary Electrophoresis Injectors and Separators on Glass Chips and Evaluation of Flow at Capillary Intersections," Jan. 1, 1994, Analytical Chemistry, vol. 66, No. 1, pp. 177–184.

Fang, Liing, et al., "On–Line Time–of–Flight Mass Spectrometric Analysis of Peptides Separated by Capillary Electrophoresis" Nov. 1, 1994, Analytical Chemistry, vol. 66, No. 21, pp. 3696–3701.

Figueroa, Alvaro, et al., "High–Performance Immobilized Metal Affinity Chromatography of Proteins on Iminodiacetic and Acid Silica–Based Bonded Phases," 1986, Journal of Chromatography, 371, pp. 335–352.

Harrison D. Jed, et al., "Rapid Separation of Fluorescein Derivatives Using a Micromachined Capillary Elecrophoresis System," 1993, Analytical Chimica Acta, 283, pp. 361–366.

Harrison, D. Jed, et al., "Towards Miniaturized Electrophoresis and Chemical Analysis Systems on Silicon; An Alternative to Chemical Sensors," 1993, Sensors and Actuators, pp. 107–116.

Harrison, D. Jed., et al., "Capillary Electrophoresis and Sample Injection Systems, Integrated on Planar Glass Chip," 1992, Analytical Chemistry, pp. 1926–1932.

Jacobsen, Stephen C., et al., "Effects of Injection Schemes and Column Geometry on the Performance of Microchip Electrophoresis Devices," 1994, Analytical Chemistry, 66, pp. 1107–1113.

Jacobsen, Stephen C., et al., "Fused Quartz Substrates for Microchip Electrophoresis," 1995, Analytical Chemistry, 67, pp. 2059–2063.

Jacobsen, Stephen C., et al., "Integrated Microdevice for DNA Restriction Fragment Analysis," 1996, Analytical Chemistry, 68, pp. 720–723.

Jacobsen, Stephen C., et al., "Microchip Capillary Electrophoresis with an Integratd Postcolumn Reactor," Oct. 15, 1994, Analytical Chemistry, vol. 66, No. 20, pp. 3472–3476.

Jacobsen, Stephen C., et al., "Microchip Electrophoresis with Sample Stacking," 1995, Electrophoresis, 15, pp. 481–486.

Jacobsen, Stephen C., et al., "Precolumn Reactions with Electrophoretic Analysis Integrated on a Microchip," 1994, Analytical Chemistry, 66, pp. 4127–4132.

James N. Alexander IV, "Development of a Nano–electrospray Mass Spectrometry Source for Nanoscale Liquid Chromatograpy and Sheathless Capillary Electrophoresis," Rapid Communication in Mass Spectrometry, 12, Jul., 1998, pp. 1187–1191.

Jansson, Marten et al., "Micro Vials on a Silicon Wafer for Sample Introduction in Capillary Electrophoresis," 1992, Journal of Chromatography, 626, pp. 310–314.

John H. Know, "Theoretical Aspects of LC with Packed and Open Small–Bore Columns," Journal of Chromatographic Science, vol. 18, Sep., 1980, pp. 453–461.

Jorg P. Kutter, Stephen C. Jacobsen, and J. Michael Ramsey, "Integrated Microchip Device with Electrokinetically Controlled Solvent Mixing for Isocratic and Gradient Elution in Micellar Electrokinetic Chromatography," Analytical Chemistry, vol. 69, No. 24, Dec. 1997, pp. 5165–5171.

K. Vanhoutte, et al., Analytical Chemistry, vol. 69, Aug. 1997, pp. 3161–3168.

Ko, Wen H., et al., "Semiconductor Integrated Circuit Technology and Micromachining," pp. 109–168. Undated.

Korner, Roman, et al., "Nano Electrospray Combined with a Quadupole Ion Trap for the Analysis of Peptides and Protein Digests," 1996, American Society for Mass Spectrometry, pp. 150–156.

Koutney, Lance B., et al., "Microchip Electrophoretic Immunoassay for Serum Cortisol," 1996, Analytical Chemistry, 68, pp. 18–22.

Kriger, M. Scott, et al., "Durable Gold–Coated Fused Silica Capillaries for Use in Electrospray Mass Spectrometry," 1995, Analytical Chemistry, 67, pp. 385–389.

Malcolm Dole; L.L. Mack; R.L. Hixes; R.C. Mobley; L.D. Ferguson; and, M.B. Alice, "Molecular Beams of Macroions" The Journal of Chemical Physics, vol. 49, No. 5, Sep. 1, 1968, pp. 2240–2249.

Manz, A., et al., "Design of an Open–Tubular Column Liquid Chromatography Using Silicon Chip Technology," 1990, Sensors and Actuators, BI, pp. 249–255.

Manz, A., et al., "Micromachining of Monocrystalline Silicon and Glass for Chemical Analysis Systems," 1991, Trends in Analytical Chemistry, vol. 10, No. 5, pp. 144–149.

Manz, Andreas, et al., "Miniaturization of Separation Techniques Using Planar Chip Technology," 1993, Journal of High Resolution Chromatography, vol., 16, pp. 433–436.

Manz, Andreas, et al., "Planar Chip Technology for Capillary Electrophoresis," 1994, Fresenius Journal of Analytical Chemistry, 348, pp. 567–571.

Manz, Andreas, et al., "Planar Chips Technology for Miniaturization and Integration of Separation Techniques into Monitoring Systems," 1992, Journal of Chromatography, 593, pp. 253–258.

Manz, Andreas, et al., "Planar Chips Technology for Miniaturization of Separation Systems: A Development Perspective in Chemical Monitoring," 1993, Advances in Chromatography, pp. 1–67.

Masamichi Yamashita and John B. Fenn, Journal of Chemical Physics, vol. 88, 1984, pp. 4451–4459.

Matthias S. Wilm, Matthias Mann, "Electrospray and Taylor–Cone theory, Dole's beam of macromolecules at last?," International Journal of Mass Spectrometry and Ion Process and Ion Processes, Jun., 1994, pp. 167–180.

Matthias Wilm and Matthias Mann, "Analytical Properties of the Nanoelectrospray Ion Source," Analytical Chemistry, vol. 68, No. 1, Jan. 1, 1996, pp. 1–8.

Moore, Alvin W., Jr., et al., "Microchip Separations of Neutral Species via Micellar Electrokinetic Capillary Chromatography," 1996, Nov. 15, 1995, Analytical Chemistry, vol. 67, No. 22, pp. 4184–4189.

Nichols, William, et al., "CE–MS for Industrial Applications Using a Liquid Junction with Ion–Spray and CF–FAB Mass Spectrometry," 1992, LC–GC, vol. 10, No. 9, pp. 676–686.

Ocvirk, Gregor, et al., "High Performance Liquid Chromatography Partially Integrated onto a Silicon Chip," 1995, Analytical Methods and Instrumentation, pp. 74–82.

Oliveres, Jose A., et al. "On–Line Mass Spectrometric Detection for Capillary Zone Electrophoresis," 1987, Analytical Chemistry, 59, pp. 1230–1231.

Overton, E.B., et al., "Development of a Temperature Programmed Microchip, High Resolution Gas Chromatograph/Mass Spectrometer for Volatile Organic Analysis," pp. 395–398.

Peters, et al., "Rigid Macroporous Polymer Monolithis," Adv. Mater., 11(14):1169–1181 (1999).

Petersen, Kurt, "Biomedical Applications of MEMS," 1996, IEEE, pp. 239–242.

Qifeng Xue; Frantisek Foret; Yuriy M. Dunayevskiy; Paul M. Zavracky, Nicol E. McGruer, and, Barry L. Karger, "Multichannel Microchip Electrospray Mass Spectrometry," Analytical Chemistry, vol. 69, No. 3, Feb. 1, 1997, pp. 426–430.

R.S. Ramsey and J.M. Ramsey, "Generating Electrospray from Microchip Devices Using Electroosmotic Pumping," Analytical Chemistry, vol. 69, No. 6, Mar. 15, 1997, p. 1174–1178.

Raymond, Daniel E., et al., "Continuous Sample Pretreatment Using a Free–Flow Electrophoresis Device Integrated onto a Silicon Chip," Sep. 15, 1994, Analytical Chemistry, vol. 68, No. 18, pp. 2858–2865.

Richard B. Cole, "Electrospray Ionization Mass Spectrometry," John Wiley & Sons, Inc., 1997, pp. 1–63.

Roeraade, Johan, "Nano–Sized Systems for Bioanalysis (abstract)," Royal Institute of Technology, Sweden, pp. 3, 19 & 63.

Seiler, Kurt, et al., "Electroosmotic Pumping and Valveless Control of Fluid Flow within a Manifold of Capillaries on a Glass Chip," Oct. 15, 1994, Analytical Chemistry, vol. 66, No. 20, pp. 3485–3491.

Seiler, Kurt, et al., "Planar Glass Chips for Capillary Electrophoresis: Repetitive Sample Injection, Quantitation, and Separation Efficiency," 1993, Analytical Chemistry, vol. 65, No. 10, pp. 1481–1488.

Shoffner, Mann A., et al., "Chip PCR. I. Surface Passivation of Microfabricated Silicon–Glass Chips for PCR," 1996, Nucleic Acids Research, vol. 24, No. 2, pp. 375–379.

Sjolander, Stefan, et al., "Integrated Fluid Handling System for Biomolecular Interaction Analysis," 1991, Analytical Chemistry, 63, pp. 2338–2345.

Smith, R.D., et al., "New Developments in Microsale Separations and Mass Spectrometry for Biomonitoring; Capillary Electrophoresis and Electrospray Ionization Mass Spectrometry," 1993, Journal of Toxicology and Environmental Health, pp. 147–158.

Smith, Richard D., et al., "*Improved Electrospray Ionization Interface for Capillary Zone Electrophoresis–Mass Spectrometry,*" 1988, Analytical Chemistry, vol. 60, pp. 1948–1952.

Snyder, *Introduction to Modern Liquid Chromatography*, John Wiley & Sons, Inc., pp. 270–272 and 277–278 (1979).

Stephen C. Jacobson; Roland Hergenroder; Lance B. Koutny; and, J. Michael Ramsey, "*High–Speed Separations on a Microchip,*" Anal. Chem., Apr. 1, 1994, 66, 1114–1118.

Stephen, C. Jacobson; Roland Hergenroder; Lance B. Koutny; and, J. Michael Ramsey, "*Open Channel Electrochromatography on a Microchip,*" Anal. Chem. 1994, 66, 2369–2373.

Valaskovic, Gary A., et al., "*Attomole–Sensitivity Electrospray Source of Large Molecule Mass Spectrometry,*" Oct. 15, 1995, Analytical Chemistry, vol. 67, No. 20, pp. 3802–3805.

Wahl, Jon H., et al., "*Sheathless Capillary Elecrophoresis–Electrospray Ionization Mass Spectrometry Using 10 pm I.D. Capillaries; Analyses of Tryptic Digests of Cytochrome C,*" Journal of Chromatography A, 659, pp. 217–222.

Wang, Xuan–Qi, et al., "*Polymer–Based Electrospray Chips for Mass Spectrometry,*" 1999, IEEE, pp. 523–528.

Whitheouse, Craig M., et al., "*Electrospray Interface for Liquid Chromatographs and Mass Spectrometers,*" Mar., 1985, Analytical Chemistry, vol. 57, No. 3, pp. 675–679.

Wooley, Adam T., et al., "*Ultra–High–Speed DNA Sequencing Using Capillary Electrophoresis Chips,*" 1995, Analytical Chemistry, 67, pp. 3676–3680.

Woolley, et al., "*Ultra–High–Speed DNA Fragment Separations Using Microfabricated Capillary Array Electrophoresis Chips,*" Nov., 1994, Proc. Natl. Acad. Sci., USA, vol. 91, pp. 11348–11352.

Yoshida, Yu, et al., "*Direct Measurement of Mass Fragmentograms for Eluents from a Micro–Liquid Chromatography Using an Improved Nebulizing Interface,*" Jan., 1980, Journal of HRC & CC, vol. 3, pp. 16–20.

\* cited by examiner

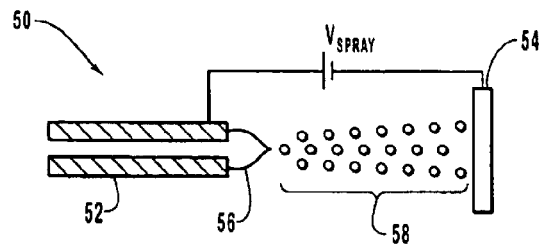
FIG. 1
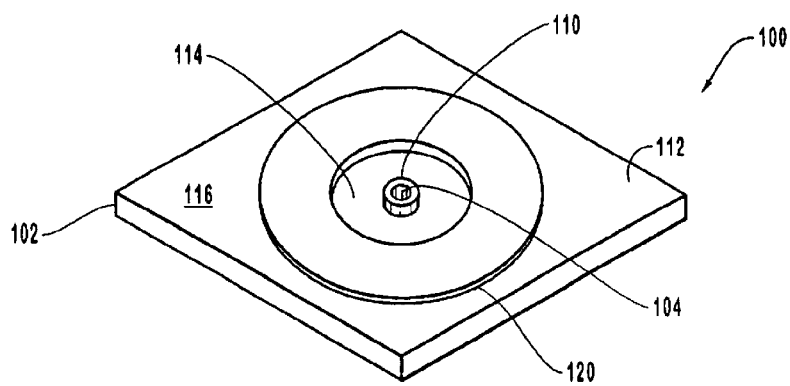
FIG. 2
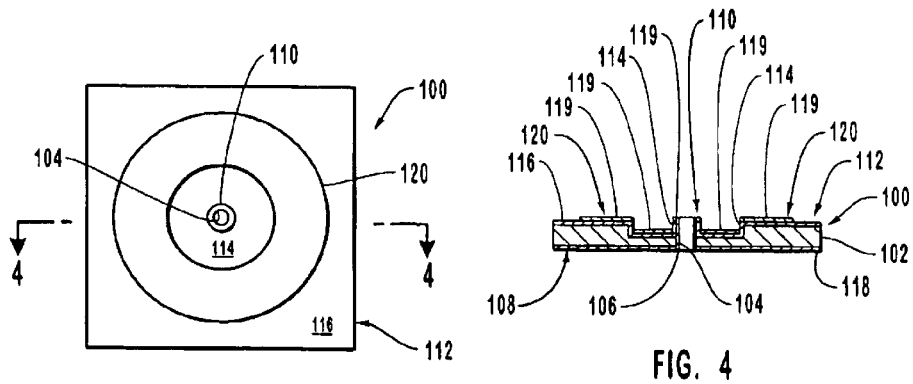
FIG. 3
FIG. 4

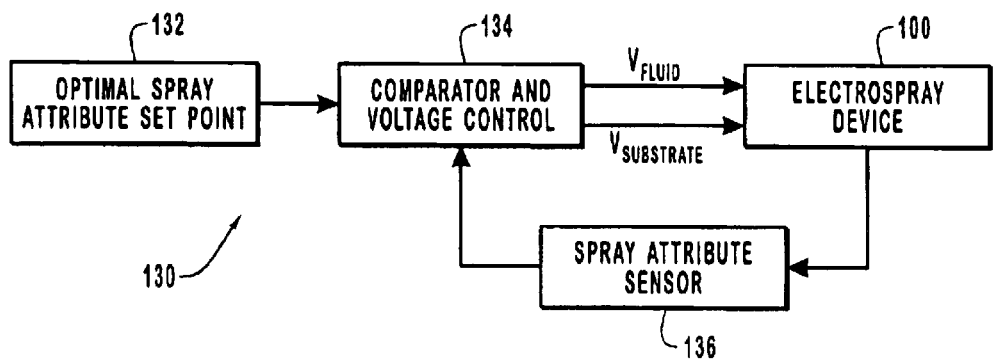
FIG. 8
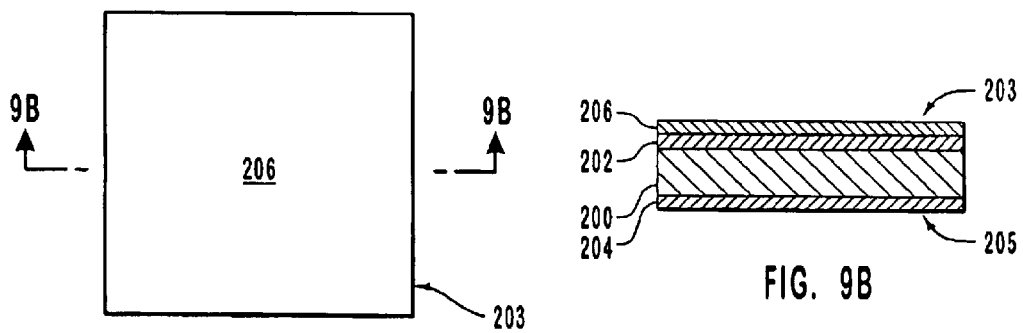
FIG. 9A
FIG. 9B

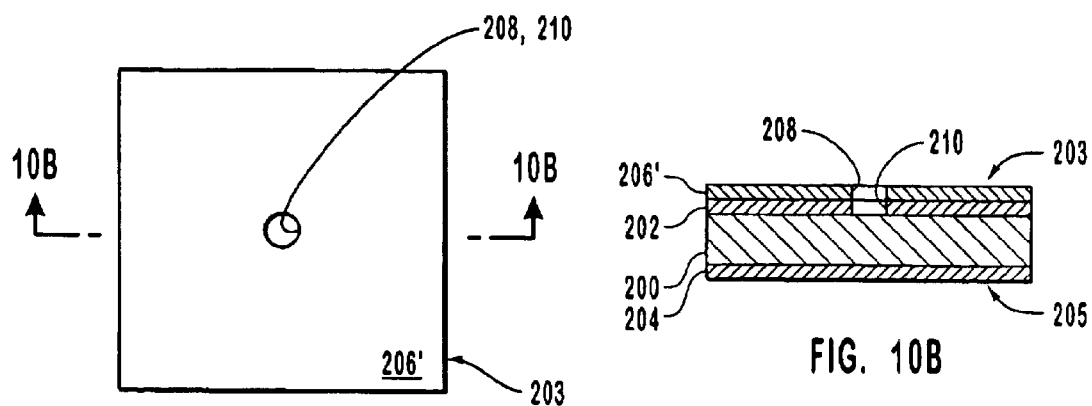
FIG. 10A
FIG. 10B
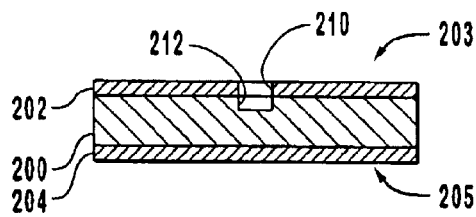
FIG. 11
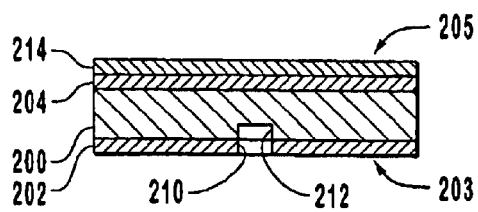
FIG. 12

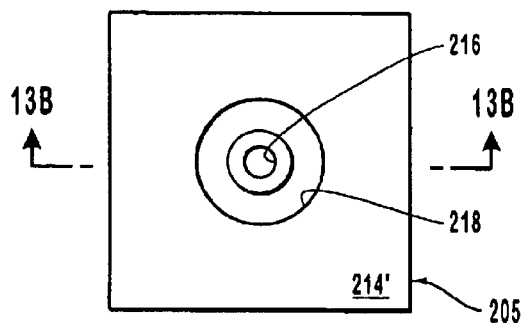
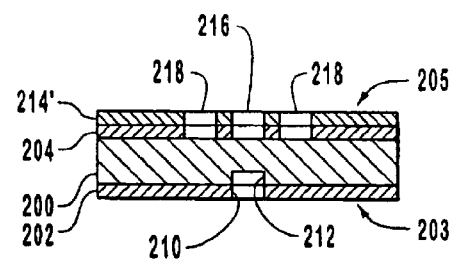
FIG. 13A
FIG. 13B
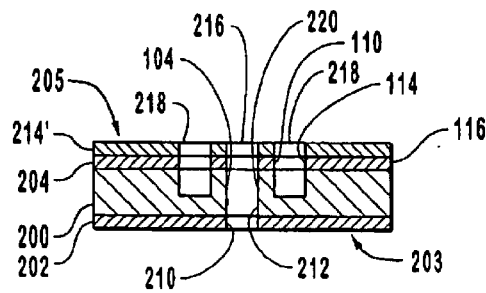
FIG. 14
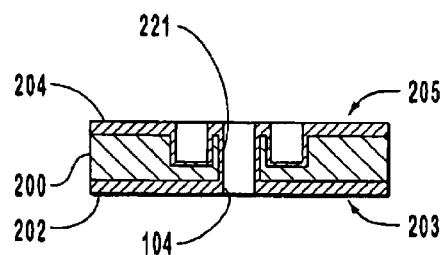
FIG. 15

ELECTROSPRAY NOZZLE AND MONOLITHIC SUBSTRATE

CROSS-REFERENCE TO RELATED APPLICATIONS

This application is a continuation of application Ser. No. 10/771,553, filed on Feb. 4, 2004, which was a continuation of application Ser. No. 09/702,955, filed on Oct. 31, 2000, now U.S. Pat. No. 6,780,313 which is a divisional of application Ser. No. 09/156,507, filed Sep. 17, 1998, now abandoned, all of which are incorporated herein in their entirety and to which priority is claimed.

This application is related to the following commonly owned patents and pending applications: U.S. Pat. No. 6,563,111; U.S. Pat No. 6,569,324; U.S. Pat. No. 6,579,452; U.S. Pat. No. 6,633,031; Ser. No. 09/698,329; Ser. No. 09/702,955; Ser. No. 10/426,455; Ser. No. 10/655,246; and Ser. No. 10/771,553.

BACKGROUND OF THE INVENTION

1. The Field of the Invention

The present invention relates generally to an integrated miniaturized chemical analysis system fabricated using microelectromechanical systems (MEMS) technology. In particular, the present invention relates to an integrated monolithic microfabricated electrospray and liquid chromatography device. This achieves a significant advantage in terms of high-throughput analysis by mass spectrometry, as used, for example, in drug discovery, in comparison to a conventional system.

2. The Field of the Invention

New developments in drug discovery and development are creating new demands on analytical techniques. For example, combinatorial chemistry is often employed to discover new lead compounds or to create variations of a lead compound. Combinatorial chemistry techniques can generate thousands or millions of compounds (combinatorial libraries) in a relatively short time (on the order of days to weeks). Testing such a large number of compounds for biological activity in a timely and efficient manner requires high-throughput screening methods which allow rapid evaluation of the characteristics of each candidate compound.

The compounds in combinatorial libraries are often tested simultaneously against a molecular target. For example, an enzyme assay employing a colorimetric measurement may be run in a 96-well plate. An aliquot of enzyme in each well is combined with tens or hundreds of compounds. An effective enzyme inhibitor will prevent development of color due to the normal enzyme reaction, allowing for rapid spectroscopic (or visual) evaluation of assay results. If ten compounds are present in each well, 960 compounds can be screened in the entire plate, and one hundred thousand compounds can be screened in 105 plates, allowing for rapid and automated testing of the compounds.

Often, however, determination of which compounds are present in certain portions of a combinatorial library is difficult, due to the manner of synthesis of the library. For example, the "split-and-pool" method of random peptide synthesis in U.S. Pat. No. 5,182,366, describes a way of creating a peptide library where each resin bead carries a unique peptide sequence. Placing ten beads in each well of a 96-well plate, followed by cleavage of the peptides from the beads and removal of the cleavage solution, would result in ten (or fewer) peptides in each well of the plate. Enzyme assays could then be carried out in the plate wells, allowing 100,000 peptides to be screened in 105 plates. However, the identity of the peptides would not be known, requiring analysis of the contents of each well.

The peptides could be analyzed by removing a portion of solution from each well and injecting the contents into a separation device such as liquid chromatography or capillary electrophoresis instrument coupled to a mass spectrometer. Assuming that such a method would take approximately 5 minutes per analysis, it would require over a month to analyze the contents of 105 96-well plates, assuming the method was fully automated and operating 24 hours a day.

This example illustrates the critical need for a method for rapid analysis of large numbers of compounds or complex mixtures of compounds, particularly in the context of high-throughput screening. Techniques for generating large numbers of compounds, for example through combinatorial chemistry, have been established. High-throughput screening methods are under development for a wide variety of targets, and some types of screens, such as the colorimetric enzyme assay described above and ELISA (enzyme linked immunosorbent assay) technology, are well-established. As indicated in the example above, a bottleneck often occurs at the stage where multiple mixtures of compounds, or even multiple individual compounds, must be characterized.

This need is further underscored when current developments in molecular biotechnology are considered. Enormous amounts of genetic sequence data are being generated through new DNA sequencing methods. This wealth of new information is generating new insights into the mechanism of disease processes. In particular, the burgeoning field of genomics has allowed rapid identification of new targets for drug development efforts. Determination of genetic variations between individuals has opened up the possibility of targeting drugs to individuals based on the individual's particular genetic profile. Testing for cytotoxicity, specificity, and other pharmaceutical characteristics could be carried out in high-throughput assays instead of expensive animal testing and clinical trials. Detailed characterization of a potential drug or lead compound early in the drug development process thus has the potential for significant savings both in time and expense.

Development of viable screening methods for these new targets will often depend on the availability of rapid separation and analysis techniques for analyzing the results of assays. For example, an assay for potential toxic metabolites of a candidate drug would need to identify both the candidate drug and the metabolites of that candidate. An assay for specificity would need to identify compounds which bind differentially to two molecular targets such as a viral protease and a mammalian protease.

It would therefore be advantageous to provide a method for efficient proteomic screening in order to obtain the pharmacokinetic profile of a drug early in the evaluation process. An understanding of how a new compound is absorbed in the body and how it is metabolized can enable prediction of the likelihood for an increased therapeutic effect or lack thereof.

Given the enormous number of new compounds that are being generated daily, an improved system for identifying molecules of potential therapeutic value for drug discovery is also critically needed.

It also would be desirable to provide rapid sequential analysis and identification of compounds which interact with a gene or gene product that plays a role in a disease of interest. Rapid sequential analysis can overcome the bottleneck of inefficient and time-consuming serial (one-by-one) analysis of compounds.

Accordingly, there is a critical need for high-throughput screening and identification of compound-target reactions in order to identify potential drug candidates.

Microchip-based separation devices have been developed for rapid analysis of large numbers of samples. Compared to other conventional separation devices, these microchip-based separation devices have higher sample throughput, reduced sample and reagent consumption and reduced chemical waste. The liquid flow rates for microchip-based separation devices range from approximately 1–300 nanoliters (nL) per minute for most applications.

Examples of microchip-based separation devices include those for capillary electrophoresis (CE), capillary electro-chromatography (CEC) and high-performance liquid chromatography (HPLC). See Harrison et. al, Science 1993, 261, 859–897; Jacobson et. al, Anal. Chem. 1994, 66, 1114–1118; and Jacobson et. al, Anal. Chem. 1994, 66, 2369–2373. Such separation devices are capable of fast analyses and provide improved precision and reliability compared to other conventional analytical instruments.

Liquid chromatography (LC) is a well-established analytical method for separating components of a fluid for subsequent analysis and/or identification. Traditionally, liquid chromatography utilizes a separation column, such as a cylindrical tube, filled with tightly packed beads, gel or other appropriate particulate material to provide a large surface area. The large surface area facilitates fluid interactions with the particulate material, and the tightly packed, random spacing of the particulate material forces the liquid to travel over a much longer effective path than the length of the column. In particular, the components of the fluid interact with the stationary phase (the particles in the liquid chromatography column) as well as the mobile phase (the liquid eluent flowing through the liquid chromatography column) based on the partition coefficients for each of the components. The partition coefficient is a defined as the ratio of the time an analyte spends interacting with the stationary phase to the time spent interacting with the mobile phase. The longer an analyte interacts with the stationary phase, the higher the partition coefficient and the longer the analyte is retained on the liquid chromatography column. The components may be detected spectroscopically after elution from the liquid chromatography column by coupling the exit of the column to a post-column detector.

Spectroscopic detectors rely on a change in refractive index, ultraviolet and/or visible light absorption, or fluorescence after excitation with a suitable wavelength to detect the separated components. Alternatively, the separated components may be passed from the liquid chromatography column into other types of analytical instruments for analysis. The analysis outcome depends upon the sequenced arrival of the components separated by the liquid chromatography column and is therefore time-dependent.

The length of liquid transport from the liquid chromatography column to the analysis instrument such as the detector is preferably minimized in order to minimize diffusion and thereby maximize the separation efficiency and analysis sensitivity. The transport length is referred to as the dead volume or extra-column volume.

Capillary electrophoresis is a technique that utilizes the electrophoretic nature of molecules and/or the electroosmotic flow of fluids in small capillary tubes to separate components of a fluid. Typically a fused silica capillary of 100 μm inner diameter or less is filled with a buffer solution containing an electrolyte. Each end of the capillary is placed in a separate fluidic reservoir containing a buffer electrolyte.

A potential voltage is placed in one of the buffer reservoirs and a second potential voltage is placed in the other buffer reservoir. Positively and negatively charged species will migrate in opposite directions through the capillary under the influence of the electric field established by the two potential voltages applied to the buffer reservoirs. Electroosmotic flow is defined as the fluid flow along the walls of a capillary due to the migration of charged species from the buffer solution. Some molecules exist as charged species when in solution and will migrate through the capillary based on the charge-to-mass ratio of the molecular species. This migration is defined as electrophoretic mobility. The electroosmotic flow and the electrophoretic mobility of each component of a fluid determine the overall migration for each fluidic component. The fluid flow profile resulting from electroosmotic flow is flat due to the reduction in frictional drag along the walls of the separation channel. This results in improved separation efficiency over liquid chromatography where the flow profile is parabolic resulting from pressure driven flow.

Capillary electrochromatography is a hybrid technique which utilizes the electrically driven flow characteristics of electrophoretic separation methods within capillary columns packed with a solid stationary phase typical of liquid chromatography. It couples the separation power of reversed-phase liquid chromatography with the high efficiencies of capillary electrophoresis. Higher efficiencies are obtainable for capillary electrochromatography separations over liquid chromatography because the flow profile resulting from electroosmotic flow is flat due to the reduction in frictional drag along the walls of the separation channel when compared to the parabolic flow profile resulting from pressure driven flows. Furthermore, smaller particle sizes can be used in capillary electrochromatography than in liquid chromatography because no back pressure is generated by electroosmotic flow. In contrast to electrophoresis, capillary electrochromatography is capable of separating neutral molecules due to analyte partitioning between the stationary and mobile phases of the column particles using a liquid chromatography separation mechanism.

The separated product of such separation devices may be introduced as the liquid sample to a device that is used to produce electrospray ionization. The electrospray device may be interfaced to an atmospheric pressure ionization mass spectrometer (API-MS) for analysis of the electrosprayed fluid.

A schematic of an electrospray system 50 is shown in FIG. 1. An electrospray is produced when a sufficient electrical potential difference $V_{spray}$ is applied between a conductive or partly conductive fluid exiting a capillary orifice and an electrode so as to generate a concentration of electric field lines emanating from the tip or end of a capillary 52 of an electrospray device. When a positive voltage $V_{spray}$ is applied to the tip of the capillary relative to an extracting electrode 54, such as one provided at the ion-sampling orifice to the mass spectrometer, the electric field causes positively-charged ions in the fluid to migrate to the surface of the fluid at the tip of the capillary. When a negative voltage $V_{spray}$ is applied to the tip of the capillary relative to an extracting electrode 54, such as one provided at the ion-sampling orifice to the mass spectrometer, the electric field causes negatively-charged ions in the fluid to migrate to the surface of the fluid at the tip of the capillary.

When the repulsion force of the solvated ions exceeds the surface tension of the fluid sample being electrosprayed, a volume of the fluid sample is pulled into the shape of a cone, known as a Taylor cone 56 which extends from the tip of the capillary. Small charged droplets 58 are formed from the tip of the Taylor cone 56 and are drawn toward the extracting electrode 54. This phenomenon has been described, for example, by Dole et al., *Chem. Phys.* 1968, 49, 2240 and Yamashita and Fenn, *J. Phys. Chem.* 1984, 88, 4451. The potential voltage required to initiate an electrospray is dependent on the surface tension of the solution as described by, for example, Smith, *IEEE Trans. Ind. App.* 1986, IA-22, 527–535. Typically, the electric field is on the order of approximately $10^6$ V/m. The physical size of the capillary determines the density of electric field lines necessary to induce electrospray.

One advantage of electrospray ionization is that the response for an analyte measured by the mass spectrometer detector is dependent on the concentration of the analyte in the fluid and independent of the fluid flow rate. The response of an analyte in solution at a given concentration would be comparable using electrospray ionization combined with mass spectrometry at a flow rate of 100 $\mu$/min compared to a flow rate of 100 nL/min.

The process of electrospray ionization at flow rates on the order of nanoliters per minute has been referred to as "nanoelectrospray". Electrospray into the ion-sampling orifice of an API mass spectrometer produces a quantitative response from the mass spectrometer detector due to the analyte molecules present in the liquid flowing from the capillary.

Thus, it is desirable to provide an electrospray ionization device for integration upstream with microchip-based separation devices and for integration downstream with API-MS instruments.

Attempts have been made to manufacture an electrospray device which produces nanoelectrospray. For example, Wilm and Mann, *Anal. Chem.* 1996, 68, 1–8 describes the process of electrospray from fused silica capillaries drawn to an inner diameter of 2–4 $\mu$m at flow rates of 20 nL/min. Specifically, a nanoelectrospray at 20 nL/min was achieved from a 2 $\mu$m inner diameter and 5 $\mu$m outer diameter pulled fused-silica capillary with 600–700 V at a distance of 1–2 mm from the ion-sampling orifice of an API mass spectrometer.

Ramsey et al., *Anal. Chem.* 1997, 69, 1174–1178 describes nanoelectrospray at 90 nL/min from the edge of a planar glass microchip with a closed separation channel 10 $\mu$m deep, 60 $\mu$m wide and 33 mm in length using electroosmotic flow and applying 4.8 kV to the fluid exiting the closed separation channel on the edge of the microchip for electrospray formation, with the edge of the chip at a distance of 3–5 mm from the ion-sampling orifice of an API mass spectrometer. Approximately 12 nL of the sample fluid collects at the edge of the chip before the formation of a Taylor cone and stable nanoelectrospray from the edge of the microchip. However, collection of approximately 12 nL of the sample fluid will result in remixing of the fluid, thereby undoing the separation done in the separation channel. Remixing causes band broadening at the edge of the microchip, fundamentally limiting its applicability for nanoelectrospray-mass spectrometry for analyte detection. Thus, nanoelectrospray from the edge of this microchip device after capillary electrophoresis or capillary electrochromatography separation is rendered impractical. Furthermore, because this device provides a flat surface, and thus a relatively small amount of physical asperity, for the formation of the electrospray, the device requires an impractically high voltage to initiate electrospray, due to poor field line concentration.

Xue, Q.; Foret, F.; Dunayevskiy, Y. M.; Zavracky, P. M.; McGruer, N.E.; Karger, B. L. *Anal. Chem.* 1997, 69, 426–430 describes a stable nanoelectrospray from the edge of a planar glass microchip with a closed channel 25 $\mu$m deep, 60 $\mu$m wide and 35–50 mm in length and applying 4.2 kV to the fluid exiting the closed separation channel on the edge of the microchip for electrospray formation, with the edge of the chip at a distance of 3–8 mm from the ion-sampling orifice of an API mass spectrometer. A syringe pump is utilized to deliver the sample fluid to the glass microchip electrosprayer at a flow rate between 100–200 nL/min. The edge of the glass microchip is treated with a hydrophobic coating to alleviate some of the difficulties associated with nanoelectrospray from a flat surface and which slightly improves the stability of the nanoelectrospray. Electrospraying in this manner from a flat surface again results in poor field line concentration and yields an inefficient electrospray.

Desai et al. 1997 *International Conference on Solid-State Sensors and Actuator*, Chicago, Jun. 16–19, 1997, 927–930 describes a multi-step process to generate a nozzle on the edge of a silicon microchip 1–3 $\mu$m in diameter or width and 40 $\mu$m in length and applying 4 kV to the entire microchip at a distance of 0.25–0.4 mm from the ion-sampling orifice of an API mass spectrometer. This nanoelectrospray nozzle reduces the dead volume of the sample fluid. However, the extension of the nozzle from the edge of the microchip exposes the nozzle to accidental breakage. Because a relatively high spray voltage was utilized and the nozzle was positioned in very close proximity to the mass spectrometer sampling orifice, a poor field line concentration and a low efficient electrospray were achieved.

In all of the above-described devices, edge-spraying from a microchip is a poorly controlled process due to the inability to rigorously and repeatably determine the physical form of the chip's edge. In another embodiment of edge-spraying, ejection nozzles, such as small segments of drawn capillaries, are separately and individually attached to the chip's edge. This process is inherently cost-inefficient and unreliable, imposes space constraints in chip design, and is therefore unsuitable for manufacturing.

Thus, it is also desirable to provide an electrospray ionization device with controllable spraying and a method for producing such a device which is easily reproducible and manufacturable in high volumes.

SUMMARY OF THE INVENTION

The present invention provides a silicon microchip-based electrospray device for producing reproducible, controllable and robust nanoelectrospray ionization of a liquid sample. The electrospray device may be interfaced downstream to an atmospheric pressure ionization mass spectrometer (API-MS) for analysis of the electrosprayed fluid and/or interfaced upstream to a miniaturized liquid phase separation device, which may have, for example, glass, plastic or silicon substrates or wafers.

The electrospray device of the present invention generally comprises a silicon substrate or microchip defining a channel between an entrance orifice on an injection surface and a nozzle on an ejection surface (the major surface) such that the electrospray generated by the electrospray device is generally approximately perpendicular to the ejection surface. The nozzle has an inner and an outer diameter and is defined by an annular portion recessed from the ejection surface. The annular recess extends radially from the outer diameter. The tip of the nozzle is co-planar or level with and does not extend beyond the ejection surface and thus the nozzle is protected against accidental breakage. The nozzle, channel and recessed portion are etched from the silicon substrate by reactive-ion etching and other standard semiconductor processing techniques.

All surfaces of the silicon substrate preferably have a layer of silicon dioxide thereon created by oxidization to electrically isolate the liquid sample from the substrate and the ejection and injection surfaces from each other such that different potential voltages may be individually applied to each surface and the liquid sample. The silicon dioxide layer also provides for biocompatibility. The electrospray apparatus further comprises at least one controlling electrode electrically contacting the substrate through the oxide layer for the application of an electric potential to the substrate.

Preferably, the nozzle, channel and recess are etched from the silicon substrate by reactive-ion etching and other standard semiconductor processing techniques. The injection-side feature(s), through-substrate fluid channel, ejection-side features, and controlling electrodes—are formed monolithically from a monocrystalline silicon substrate. That is, they are formed during the course of and as a result of a fabrication sequence that requires no manipulation or assembly of separate components.

Because the electrospray device is manufactured using reactive-ion etching and other standard semiconductor processing techniques, the dimensions of such a device can be very small, for example, as small as 2 $\mu$m inner diameter and 5 $\mu$m outer diameter. Thus, a nozzle having, for example, 5 $\mu$m inner diameter and 250 $\mu$m in height only has a volume of 4.9 pL (picoliter). In contrast, an electrospray device from the flat edge of a glass microchip would introduce additional dead volume of 12 nL compared to the volume of a separation channel of 19.8 nL thereby allowing remixing of the fluid components and undoing the separation done by the separation channel. The micrometer-scale dimensions of the electrospray device minimizes the dead volume and thereby increases efficiency and analysis sensitivity.

The electrospray device of the present invention provides for the efficient and effective formation of an electrospray. By providing an electrospray surface from which the fluid is ejected with dimensions on the order of micrometers, the electrospray device limits the voltage required to generate a Taylor cone as the voltage is dependent upon the nozzle diameter, surface tension of the fluid and the distance of the nozzle from the extracting electrode. The nozzle of the electrospray device provides the physical asperity on the order of micrometers on which a large electric field is concentrated. Further, the electrospray device may provide additional electrode(s) on the ejecting surface to which electric potential(s) may be applied and controlled independent of the electric potentials of the fluid and the extracting electrode in order to advantageously modify and optimize the electric field. The combination of the nozzle and the additional electrode(s) thus enhance the electric field between the nozzle and the extracting electrode. The large electric field, on the order of $10^6$ V/m or greater and generated by the potential difference between the fluid and extracting electrode, is thus applied directly to the fluidic cone rather than uniformly distributed in space.

The microchip-based electrospray ionization device of the present invention provides minimal extra-column dispersion as a result of a reduction in the extra-column volume and provides efficient, reproducible, reliable and rugged formation of an electrospray. The design of the ionization device is also robust such that the electrospray device can be readily mass-produced in a cost-effective, high-yielding process.

In operation, a conductive or partly conductive liquid sample is introduced into the channel through the entrance orifice on the injection surface. The liquid sample and nozzle are held at the potential voltage applied to the fluid, either by means of a wire within the fluid delivery channel to the electrospray device or by means of an electrode formed on the injection surface isolated from the surrounding surface region and from the substrate. The electric field strength at the tip of the nozzle is enhanced by the application of a voltage to the substrate and/or the ejection surface, preferably approximately less than one-half of the voltage applied to the fluid. Thus, by the independent control of the fluid/nozzle and substrate/ejection surface voltages, the electrospray device of the present invention allows the optimization of the electric field lines emanating from the nozzle. Further, when the electrospray device is interfaced downstream with a mass spectrometry device, the independent control of the fluid/nozzle and substrate/ejection surface voltages also allows for the direction and optimization of the electrospray into an acceptance region of the mass spectrometry device.

The electrospray device of the present invention may be placed 1–2 mm or up to 10 mm from the orifice of an API mass spectrometer to establish a stable nanoelectrospray at flow rates as low as 20 nL/min with a voltage of, for example, 700 V applied to the nozzle and 0–350 V applied to the substrate and/or the planar ejection surface of the silicon microchip.

An array or matrix of multiple electrospray devices of the present invention may be manufactured on a single microchip as silicon fabrication using standard, well-controlled thin-film processes not only eliminates handling of such micro components but also allows for rapid parallel processing of functionally alike elements. The nozzles may be radially positioned about a circle having a relatively small diameter near the center of the chip. Thus, the electrospray device of the present invention provides significant advantages of time and cost efficiency, control, and reproducibility. The low cost of these electrospray devices allows for one-time use such that cross-contamination from different liquid samples may be eliminated.

The electrospray device of the present invention can be integrated upstream with miniaturized liquid sample handling devices and integrated downstream with an API mass spectrometer. The electrospray device may be chip-to-chip or wafer-to-wafer bonded to silicon microchip-based liquid separation devices capable of, for example, capillary electrophoresis, capillary electrochromatography, affinity chromatography, liquid chromatography (LC) or any other condensed-phase separation technique. The electrospray device may be alternatively bonded to glass-and/or polymer-based liquid separation devices with any suitable method.

In another aspect of the invention, a microchip-based liquid chromatography device may be provided. The liquid chromatography device generally comprises a separation substrate or wafer defining an introduction channel between an entrance orifice and a reservoir and a separation channel between the reservoir and an exit orifice. The separation channel is populated with separation posts extending from a side wall of the separation channel perpendicular to the fluid flow though the separation channel. Preferably, the separation posts do not extend beyond and are preferably coplanar or level with the surface of the separation substrate such that they are protected against accidental breakage during the manufacturing process. Component separation occurs in the separation channel where the separation posts perform the liquid chromatography function by providing large surface areas for the interaction of fluid flowing through the separation channel. A cover substrate may be bonded to the separation substrate to enclose the reservoir and the separation channel adjacent the cover substrate.

The liquid chromatography device may further comprise one or more electrodes for application of electric potentials to the fluid at locations along the fluid path. The application of different electric potentials along the fluid path may facilitate the fluid flow through the fluid path.

The introduction and separation channels, the entrance and exit orifices and the separation posts are preferably etched from a silicon substrate by reactive-ion etching and other standard semiconductor processing techniques. The separation posts are preferably oxidized silicon posts which may be chemically modified to optimize the interaction of the components of the sample fluid with the stationary separation posts.

In another aspect of the invention, the liquid chromatography device may be integrated with the electrospray device such that the exit orifice of the liquid chromatography device forms a homogenous interface with the entrance orifice of the electrospray device, thereby allowing the on-chip delivery of fluid from the liquid chromatography device to the electrospray device to generate an electrospray. The nozzle, channel and recessed portion of the electrospray device may be etched from the cover substrate of the liquid chromatography device.

In yet another aspect of the invention, multiples of the liquid chromatography-electrospray system may be formed on a single chip to deliver a multiplicity of samples to a common point for subsequent sequential analysis. The multiple nozzles of the electrospray devices may be radially positioned about a circle having a relatively small diameter near the center of the single chip.

The radially distributed array of electrospray nozzles on a multi-system chip may be interfaced with a sampling orifice of a mass spectrometer by positioning the nozzles near the sample orifice. The tight radial configuration of the electrospray nozzles allows the positioning thereof in close proximity to the sampling orifice of a mass spectrometer.

The multi-system chip thus provides a rapid sequential chemical analysis system fabricated using microelectromechanical system MEMS) technology. For example, the multi-ion system chip enables automated, sequential and injection of a multiplicity of samples, resulting in significantly greater analysis throughput and utilization of the mass spectrometer instrument for, for example, high-throughput detection of compounds for drug discovery.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 1 shows a schematic of an electrospray system;

FIG. 2 shows a perspective view of an electrospray device of the present invention;

FIG. 3 shows a plan view of the electrospray device of FIG. 2;

FIG. 4 shows a cross-sectional view of the electrospray device of FIG. 3 taken along line 4—4;

FIG. 8 illustrates a feedback control circuit incorporating an electrospray device of the present invention;

FIGS. 9–20G show an example of a fabrication sequence of the electrospray device;

FIGS. 36A–46C show an example of a fabrication sequence of the liquid chromatography device;

DETAILED DESCRIPTION OF THE INVENTION

Figure 5:
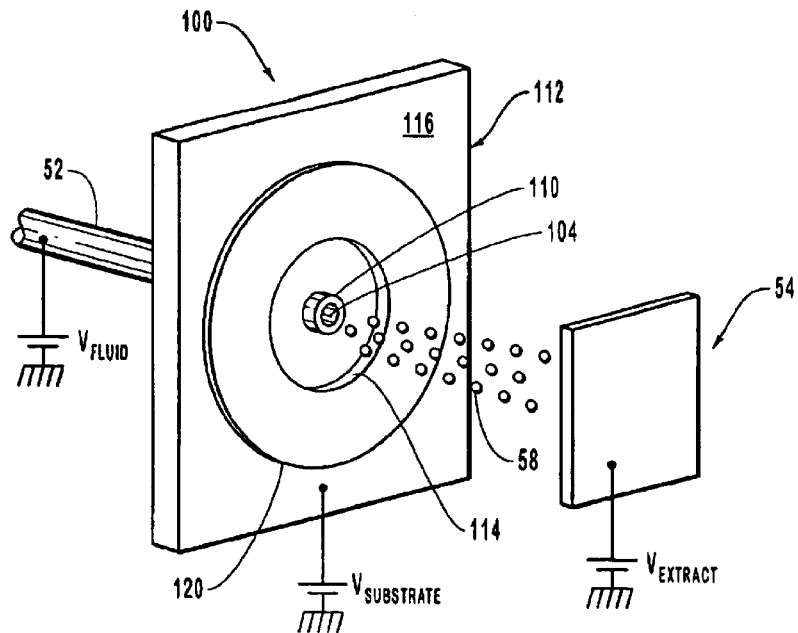
FIG. 5 shows a schematic of an electrospray system comprising an electrospray device of the present invention.

An aspect of the present invention provides a silicon microchip-based electrospray device for producing electrospray ionization of a liquid sample. The electrospray device may be interfaced downstream to an atmospheric pressure ionization mass spectrometer (API-MS) for analysis of the electrosprayed fluid. Another aspect of the invention is an integrated miniaturized liquid phase separation device, which may have, for example, glass, plastic or silicon substrates integral with the electrospray device. The descriptions that follow present the invention in the context of a liquid chromatograph separation device. However, it will be readily recognized that equivalent devices can be made that utilize other microchip-based separation devices. The following description is presented to enable any person skilled in the art to make and use the invention. Descriptions of specific applications are provided only as examples. Various modifications to the preferred embodiment will be readily apparent to those skilled in the art, and the general principles defined herein may be applied to other embodiments and applications without departing from the spirit and scope of the invention. Thus, the present invention is not intended to be limited to the embodiments shown, but is to be accorded the widest scope consistent with the principles and features disclosed herein.

Electrospray Device

FIGS. 2–4 show, respectively, a perspective view, a plan view and a cross-sectional view of an electrospray device 100 of the present invention. The electrospray apparatus of the present invention generally comprises a silicon substrate or microchip or wafer 102 defining a channel 104 through substrate 102 between an entrance orifice 106 on an injection surface 108 and a nozzle 110 on an ejection surface 112. The channel may have any suitable cross-sectional shape such as circular or rectangular. The nozzle 110 has an inner and an outer diameter and is defined by a recessed region 114. The region 114 is recessed from the ejection surface 112, extends outwardly from the nozzle 110 and may be annular. The tip of the nozzle 110 does not extend beyond and is preferably coplanar or level with the ejection surface 112 to thereby protect the nozzle 110 from accidental breakage.

Preferably, the injection surface 108 is opposite the ejection surface 112. However, although not shown, the injection surface may be adjacent to the ejection surface such that the channel extending between the entrance orifice and the nozzle makes a turn within the device. In such a configuration, the electrospray device would comprise two substrates bonded together. The first substrate may define a through-substrate channel extending between a bonding surface and the ejection surface, opposite the bonding surface. The first substrate may further define an open channel recessed from the bonding surface extending from an orifice of the through-substrate channel and the injection surface such that the bonding surface of the second substrate encloses the open channel upon bonding of the first and second substrates. Alternatively, the second substrate may define an open channel recessed from the bonding surface such that the bonding surface of the first substrate encloses the open channel upon bonding of the first and second substrates. In yet another variation, the first substrate may further define a second through-substrate channel while the open channel extends between the two through-substrate channels. Thus, the injection surface is the same surface as the ejection surface.

A grid-plane region 116 of the ejection surface 112 is exterior to the nozzle 110 and to the recessed region 114 and may provide a surface on which a layer of conductive material 119, including a conductive electrode 120, may be formed for the application of an electric potential to the substrate 102 to modify the electric field pattern between the ejection surface 112, including the nozzle tip 110, and the extracting electrode 54. Alternatively, the conductive electrode may be provided on the injection surface 108 (not shown).

The electrospray device 100 further comprises a layer of silicon dioxide 118 over the surfaces of the substrate 102 through which the electrode 120 is in contact with the substrate 102 either on the ejection surface 112 or on the injection surface 108. The silicon dioxide 118 formed on the walls of the channel 104 electrically isolates a fluid therein from the silicon substrate 102 and thus allows for the independent application and sustenance of different electrical potentials to the fluid in the channel 104 and to the silicon substrate 102. The ability to independently vary the fluid and substrate potentials allows the optimization of the electrospray through modification of the electric field line pattern, as described below. Alternatively, the substrate 102 can be controlled to the same electrical potential as the fluid when appropriate for a given application.

As shown in FIG. 5, to generate an electrospray, fluid may be delivered to the entrance orifice 106 of the electrospray device 100 by, for example, a capillary 52 or micropipette. The fluid is subjected to a potential voltage $V_{fluid}$ via a wire (not shown) positioned in the capillary 52 or in the channel 104 or via an electrode (not shown) provided on the injection surface 108 and isolated from the surrounding surface region and the substrate 102. A potential voltage $V_{substrate}$ may also be applied to the electrode 120 on the grid-plane 116, the magnitude of which is preferably adjustable for optimization of the electrospray characteristics. The fluid flows through the channel 104 and exits or is ejected from the nozzle 110 in the form of very fine, highly charged fluidic droplets 58. The electrode 54 may be held at a potential voltage $V_{extract}$ such that the electrospray is drawn toward the extracting electrode 54 under the influence of an electric field. As it is the relative electric potentials which affect the electric field, the potential voltages of the fluid, the substrate and the extracting electrode may be easily adjusted and modified to achieve the desired electric field. Generally, the magnitude of the electric field should not exceed the dielectric breakdown strength of the surrounding medium, typically air.

In one embodiment, the nozzle 110 may be placed up to 10 mm from the sampling orifice of an API mass spectrometer serving as the extracting electrode 54. A potential voltage $V_{fluid}$ ranging from approximately 500–1000 V, such as 700 V, is applied to the fluid. The potential voltage of the fluid $V_{fluid}$ may be up to 500 V/μm of silicon dioxide on the surface of the substrate 102 and may depend on the surface tension of the fluid being sprayed and the geometry of the nozzle 110. A potential voltage of the substrate $V_{substrate}$ of approximately less than half of the fluid potential voltage $V_{fluid}$, or 0–350 V, is applied to the electrode on the grid-plane 116 to enhance the electric field strength at the tip of the nozzle 110. The extracting electrode 54 may be held at or near ground potential $V_{extract}$ (0 V). Thus, a nanoelectrospray of a fluid introduced to the electrospray device 100 at flow rates less than 1,000 nL/min is drawn toward the extracting electrode 54 under the influence of the electric field.

The nozzle 110 provides the physical asperity for concentrating the electric field lines emanating from the nozzle 110 in order to achieve efficient electrospray. The nozzle 110 also forms a continuation of and serves as an exit orifice of the through-substrate channel 104. Furthermore, the recessed region 114 serves to physically isolate the nozzle 110 from the grid-plane region 116 of the ejection surface 112 to thereby promote the concentration of electric field lines and to provide electrical isolation between the nozzle 110 and the grid-plane region 116. The present invention allows the optimization of the electric field lines emanating from the nozzle 110 through independent control of the potential voltage $V_{fluid}$ of the fluid and nozzle 110 and the potential voltage $V_{substrate}$ of the electrode on the grid-plane 116 of the ejection surface 112.

Figure 6:
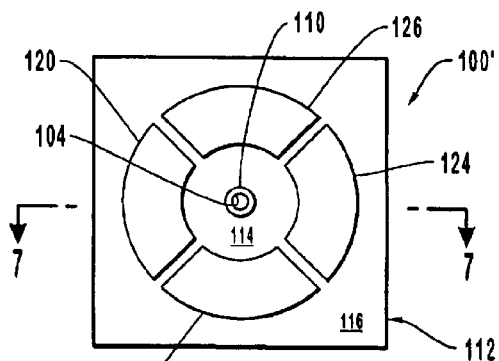
FIG. 6 shows a plan view of an electrospray device having multiple electrodes on the ejection surface of the device.
Figure 7:
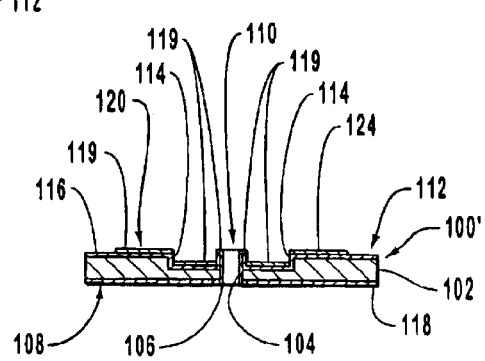
FIG. 7 shows a cross-sectional view of the electrospray device of FIG. 6 taken along line 7—7.
Figure 16:
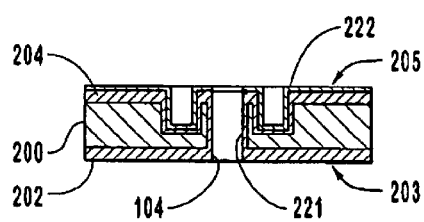
Figure 17:
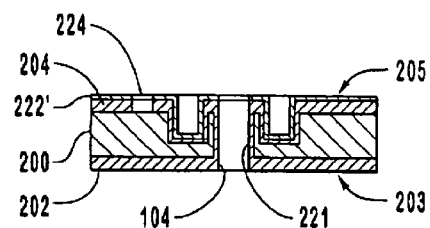

In addition to the electrode 120, one or more additional conductive electrodes may be provided on the silicon dioxide layer 118 on the ejection surface 112 of the substrate 102. FIGS. 6 and 7 show, respectively, a plan view and a cross-sectional view of an example of an electrospray device 100' wherein the conductive layer 119 defines three additional electrodes 122, 124, 126 on the ejection surface 112 of the substrate 102. Because the silicon dioxide layer 118 on the ejection surface 112 electrically isolates the silicon substrate 102 from the additional electrodes 122, 124, 126 on the ejection surface 112 and because the additional electrodes 122, 124, 126 are physically separated from each other, the electrical potential applied to each of the additional electrodes 122, 124, 126 can be controlled independently from each other, from the substrate 102 and from the fluid. Thus, additional electrodes 122, 124, 126 may be utilized to further modify the electric field line pattern to effect, for example, a steering and/or shaping of the electrospray. Although shown to be of similar sizes and shapes, electrode 120 and additional electrodes 122, 124, 126 may be of any same or different suitable shapes and sizes.

To further control and optimize the electrospray, a feedback control circuit 130 as shown in FIG. 8 may also be provided with the electrospray device 100. The feedback circuit 130 includes an optimal spray attribute set point 132, a comparator and voltage control 134 and one or more spray attribute sensors 136. The optimal spray attribute set point 132 is set by an operator or at a determined or default value. The one or more spray attribute sensors 136 detect one or more desired attributes of the electrospray from the electrospray device 100, such as the electrospray ion current and/or the spatial concentration of the spray pattern. The spray attribute sensor 136 sends signals indicating the value of the desired attribute of the electrospray to the comparator and voltage control 134 which compares the indicated value of the desired attribute with the optimal spray attribute set point 132. The comparator and voltage control 134 then applies potential voltages $V_{fluid}$, $V_{substrate}$ to the fluid and the silicon substrate 102, respectively, which may be independently varied to optimize the desired electrospray attribute. Although not shown, the comparator and voltage control 134 may apply independently controlled additional potential voltages to each of one or more additional conductive electrodes.

The feedback circuit 130 may be interfaced with the electrospray device 100 in any suitable fashion. For example, the feedback circuit 130 may be fabricated as an integrated circuit on the electrospray device 100, as a separate integrated circuit with electrical connection to the electrospray device 100, or as discrete components residing on a common substrate electrically connected to the substrate of the electrospray device.

Dimensions of the electrospray device 100 can be determined according to various factors such as the specific application, the layout design as well as the upstream and/or downstream device to which the electrospray device 100 is interfaced or integrated. Further, the dimensions of the channel and nozzle may be optimized for the desired flow rate of the fluid sample. The use of reactive-ion etching techniques allows for the reproducible and cost effective production of small diameter nozzles, for example, a 2 μm inner diameter and 5 μm outer diameter.

In one currently preferred embodiment, the silicon substrate 102 of the electrospray device 100 is approximately 250–600 μm in thickness and the cross-sectional area of the channel 104 is less than approximately 50,000 μm². Where the channel 104 has a circular cross-sectional shape, the channel 104 and the nozzle 110 have an inner diameter of up to 250 μm, more preferably up to 145 μm; the nozzle 110 has an outer diameter of up to 255 μm, more preferably up to 150 μm; and nozzle 110 has a height of (and the recessed portion 114 has a depth of) up to 500 μm. The recessed portion 114 preferably extends up to 1000 μm outwardly from the nozzle 110. The silicon dioxide layer 118 has a thickness of approximately 1–4 μm, preferably 1–2 μm.

Electrospray Device Fabrication Procedure

The fabrication of the electrospray device 100 will now be explained with reference to FIGS. 9–20B. The electrospray device 100 is preferably fabricated as a monolithic silicon integrated circuit utilizing established, well-controlled thin-film silicon processing techniques such as thermal oxidation, photolithography, reactivation etching (RIE), ion implantation, and metal deposition. Fabrication using such silicon processing techniques facilitates massively parallel processing of similar devices, is time- and cost-efficient, allows for tighter control of critical dimensions, is easily reproducible, and results in a wholly integral device, thereby eliminating any assembly requirements. Further, the fabrication sequence may be easily extended to create physical aspects or features on the injection surface and/or ejection surface of the electrospray device to facilitate interfacing and connection to a fluid delivery system or to facilitate integration with a fluid delivery sub-system to create a single integrated system.

Injection Surface Processing: Entrance to Through-Wafer Channel

FIGS. 9A–11 illustrate the processing steps for the injection side of the substrate in fabricating the electrospray device 100 of the present invention. Referring to the plan and cross-sectional views, respectively, of FIGS. 9A and 9B, a double-side polished silicon wafer substrate 200 is subjected to an elevated temperature in an oxidizing ambient to grow a layer or film of silicon dioxide 202 on the injection side 203 and a layer or film of silicon dioxide 204 on the ejection side 205 of the substrate 200. Each of the resulting silicon dioxide layers 202, 204 has a thickness of approximately 1–2 μm. The silicon dioxide layers 202, 204 provide electrical isolation and also serve as masks for subsequent selective etching of certain areas of the silicon substrate 200.

A film of positive-working photoresist 206 is deposited on the silicon dioxide layer 202 on the injection side 203 of the substrate 200. An area of the photoresist 206 corresponding to the entrance to a through-wafer channel which will be subsequently etched is selectively exposed through a mask by an optical lithographic exposure tool passing short-wavelength light such as blue or near-ultraviolet at wavelengths of 365, 405, or 436 nanometers.

As shown in the plan and cross-sectional views. respectively, of FIGS. 10A and 10B, after development of the photoresist 206, the exposed area 208 of the photoresist is removed and open to the underlying silicon dioxide layer 202 while the unexposed areas remain protected by photoresist 206'. The exposed area 210 of the silicon dioxide layer 202 is then etched by a fluorine-based plasma with a high degree of anisotropy and selectivity to the protective photoresist 206' until the silicon substrate 200 is reached. The remaining photoresist is removed in an oxygen plasma or in an actively oxidizing chemical bath like sulfuric acid ($H_2SO_4$) activated with hydrogen peroxide ($H_2O_2$).

As shown in the cross-sectional view of FIG. 11, an injection side portion 212 of the through channel in the silicon substrate 200 is vertically etched by another fluorine-based etch. An advantage of the fabrication process described herein is that the dimensions of the through channel, such as the aspect ratio (depth to width), can be reliably and reproducibly limited and controlled. In the case where the etch aspect ratio of the processing equipment is a limiting factor, it is possible to overcome this limitation by a first etch on one side of a wafer followed by a second etch on a second side of the wafer. For example, a current silicon etch process is generally limited to an etch aspect ratio of 30:1, such that a channel having a diameter less than approximately 10 $\mu$m through a substrate 200 having customary thickness approximately 250–600 $\mu$m would be etched from both surfaces of the substrate 200.

The depth of the channel portion 212 should be at or above a minimum in order to connect with another portion of the through channel etched from the ejection side 205 of the substrate 200. The desired depth of the recessed region 114 on the ejection side 205 determines approximately how far the ejection side portion 220 of the channel 104 is etched. The remainder of the channel 104, the injection side portion 212, is etched from the injection side. The minimum depth of channel portion 212 is typically 50 $\mu$m, although the exact etch depth above the minimum etch depth does not impact the device performance or yield of the electrospray device.

Ejection Surface Processing: Nozzle and Surrounding Surface Structure

FIGS. 12–20B illustrate the processing steps for the ejection side 205 of the substrate 200 in fabricating the electrospray device 100 of the present invention. As shown in the cross-sectional view in FIG. 12, a film of positive-working photoresist 214 is deposited on the silicon dioxide layer 204 on the ejection side 205 of the substrate 200. Patterns on the ejection side 205 are aligned to those previously formed on the injection side 203 of the substrate 200. Because silicon and its oxide are inherently relatively transparent to light in the infrared wavelength range of the spectrum, i.e. approximately 70–1000 nanometers, the extant pattern on the injection side 203 can be distinguished with sufficient clarity by illuminating the substrate 200 from the patterned injection side 203 with infrared light. Thus, the mask for the ejection side 205 can be aligned within required tolerances.

After alignment, certain areas of the photoresist 214 corresponding to the nozzle and the recessed region are selectively exposed through an ejection side mask by an optical lithographic exposure tool passing short-wavelength light, such as blue or near-ultraviolet at wavelengths of 365, 405, or 436 nanometers. A s shown in the plan and cross-sectional views, respectively, of FIGS. 13A and 13B, the photoresist 214 is then developed to remove the exposed areas of the photo resist such that the nozzle area 216 and recessed region area 218 are open to the underlying silicon dioxide layer 204 while the unexposed areas remain protected by photoresist 214'. The exposed areas 216, 218 of the silicon dioxide layer 204 are then etched by a fluorine-based plasma with a high degree of anisotropy and selectivity to the protective photoresist 214' until the silicon substrate 200 is reached.

As shown in the cross-sectional view of FIG. 14, the remaining photoresist 214' provides additional masking during a subsequent fluorine based silicon etch to vertically etch certain patterns into the ejection side 205 of the silicon substrate 200. The remaining photoresist 214' is then removed in an oxygen plasma or in an actively oxidizing chemical bath like sulfuric acid ($H_2SO_4$) activated with hydrogen peroxide ($H_2O_2$).

The fluorine-based etch creates a channel 104 through the silicon substrate 200 by forming an ejection side portion 220 of the channel 104. The fluorine based etch also creates an ejection nozzle 110, a recessed region 114 exterior to the nozzle 110 and a grid-plane region 116 exterior to the nozzle 110 and to the recessed region 114. The grid-plane region 116 is preferably co-planar with the tip of the nozzle 110 so as to physically protect the nozzle 110 from casual abrasion, stress fracture in handling and/or accidental breakage. The grid-plane region 116 also serves as a platform on which one or more conductive electrodes may be provided.

The fabrication sequence confers superior mechanical stability to the fabricated electrospray device by etching the features of the electrospray device from a monocrystalline silicon substrate without any need for assembly. The fabrication sequence allows for the control of the nozzle height by adjusting the relative amounts of injection side and ejection side silicon etching. Further, the lateral extent and shape of the recessed region 114 can be controlled independently of its depth, which affects the nozzle height and which is determined by the extent of the etch on the ejection side of the substrate. Control of the lateral extent and shape of the recessed region 114 provides the ability to modify and control the electric field pattern between the electrospray device 100 and an extracting electrode.

Oxidation for Electrical Isolation

As shown in the cross-sectional view of FIG. 15, a layer of silicon dioxide 221 is grown on all silicon surfaces of the substrate 200 by subjecting the silicon substrate 200 to elevated temperature in an oxidizing ambient. For example, the oxidizing ambient may be an ultra-pure steam produced by oxidation of hydrogen for a silicon dioxide thickness greater than approximately several hundred nanometers or pure oxygen for a silicon dioxide thickness of approximately several hundred nanometers or less. The layer of silicon dioxide 221 over all silicon surfaces of the substrate 200 electrically isolates a fluid in the channel from the silicon substrate 200 and permits the application and sustenance of different electrical potentials to the fluid in the channel 104 and to the silicon substrate 200.

All silicon surfaces are oxidized to form silicon dioxide with a thickness that is controllable through choice of temperature and time of oxidation. The final thickness of the silicon dioxide can be selected to provide the desired degree of electrical isolation in the device, where a thicker layer of silicon dioxide provides a greater resistance to electrical breakdown.

Metallization for Electric Field Control

FIGS. 16–20B illustrate the formation of a single conductive electrode electrically connected to the substrate 200 on the ejection side 205 of the substrate 200. As shown in the cross-sectional view of FIG. 16, a film of positive-working photoresist 222 is deposited over the silicon dioxide layer on the ejection side 205 of the substrate 200. An area of the photoresist 222 corresponding to the electrical contact area between the electrode and the substrate 200 is selectively exposed through another mask by an optical lithographic exposure tool passing short-wavelength light, such as blue or near-ultraviolet at wavelengths of 365, 405, or 436 nanometers.

The photoresist 222 is then developed to remove the exposed area 224 of the photoresist such that the electrical contact area between the electrode and the substrate 200 is open to the underlying silicon dioxide layer 204 while the unexposed areas remain protected by photoresist 222'. The exposed area 224 of the silicon dioxide layer 204 is then etched by a fluorine-based plasma with a high degree of anisotropy and selectivity to the protective photoresist 222' until the silicon substrate 200 is reached, as shown in the cross-sectional view of FIG. 17.

Figure 18:
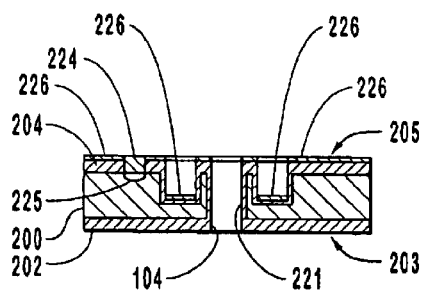
Figure 19:
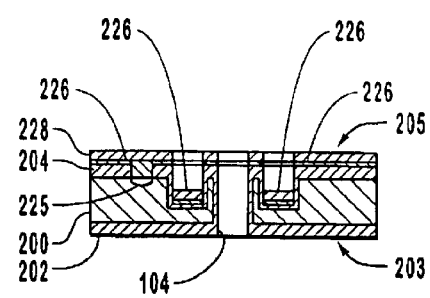

Referring now to the cross-sectional view of FIG. 18, the remaining photoresist is then removed in an oxygen plasma or in an actively oxidizing chemical bath like sulfuric acid ($H_2SO_4$) activated with hydrogen peroxide ($H_2O_2$). Utilizing the patterned ejection side silicon dioxide layer 204 as a mask. a high-dose implantation is made to form an implanted region 225 to ensure a low-resistance electrical connection between the electrode and the substrate 200. A conductive film 226 such as aluminum may be uniformly deposited on the ejection side 205 of the substrate 200 by thermal or election-beam evaporation to form an electrode 120. The thickness of the conductive film 226 is preferably approximately 3000 A, although shown having a larger thickness for clarity.

The conductive film 226 may be created by any method which does not produce a continuous film of the conductive material on the side walls of the ejection nozzle 110. Such a continuous film would electrically connect the fluid in the channel 104 and the substrate 200 so as to prevent the independent control of their respective electrical potentials. For example, the conductive film may be deposited by thermal or electron-beam evaporation of the conductive material, resulting in line-of-sight deposition on presented surfaces. Orienting the substrate 200 such that the side walls of the ejection nozzle 110 are out of the line-of-sight of the evaporation source ensures that no conductive material is deposited as a continuous film on the side walls of the ejection nozzle 110. Sputtering of conductive material in aplasma is an example of a deposition technique which would result in deposition of conductive material on all surfaces and thus is undesirable.

One or more additional conductive electrodes may be easily formed on the ejection side 205 of the substrate 200, as described above with reference to FIGS. 6 and 7. As shown in the cross-sectional view of FIG. 19, a film of positive-working photoresist 228 is deposited over the conductive film 226 on the ejection side 205 of the substrate 200. Certain areas of the photoresist 228 corresponding to the physical spaces between the electrodes are selectively exposed through another mask by an optical lithographic exposure tool passing short-wavelength light, such as blue or near-ultraviolet at wavelengths of 365, 405, or 436 nanometers.

Figure 20A:
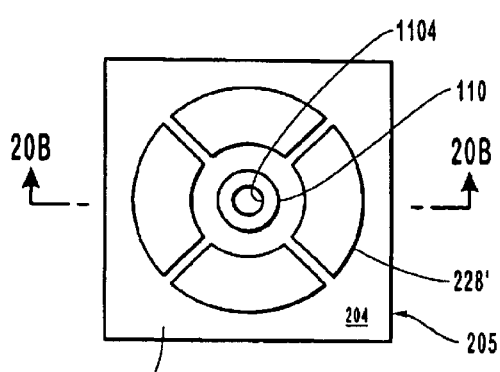
Figure 20B:
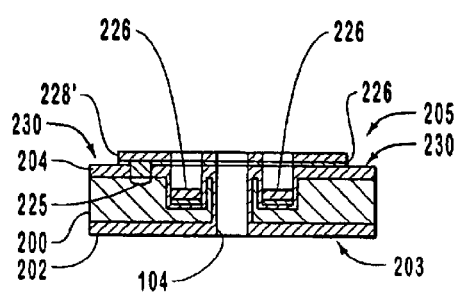

Referring now to the plan and cross-sectional views of FIGS. 20A and 20B, the photoresist 228 is developed to remove the exposed areas 230 of the photoresist such that the exposed areas are open to the underlying conductive film 226 while the unexposed areas remain protected by photoresist 228'. The exposed areas 230 of the conductive film 226 are then etched using either a wet chemical etch or a reactive-ion etch, as appropriate for the particular conductive material. The etch is either selective to the underlying silicon dioxide layer 204 or the etch must be terminated on the basis of etch rate and time of etch. Finally, the remaining photoresist is then removed in an oxygen plasma.

The etching of the conductive film 226 to the underlying silicon dioxide layer 204 results in physically and electrically separate islands of conductive material or electrodes. As described above, these electrodes can be controlled independently from the silicon substrate or channel fluid because they are electrically isolated from the substrate by the silicon dioxide and from each other by physical separation. They can be used to further modify the electric field line pattern and thereby effect a steering and/or shaping of the electrosprayed fluid. This step completes the processing and fabrication sequence for the electrospray device 100.

As described above, the conductive electrode for application of an electrical potential to the substrate of the electrospray device may be provided on the injection surface rather than the ejection surface. The fabrication sequence is similar to that for the conductive electrode provided on the ejection side 205 of the substrate 200. FIGS. 20C–20G illustrate the formation of a single conductive electrode electrically connected to the substrate 200 on the injection side 203 of the substrate 200.

Figure 20C:
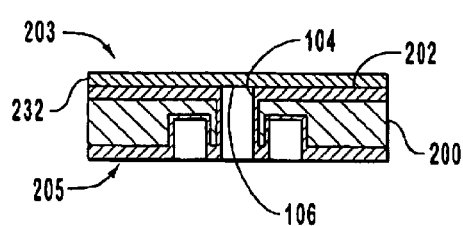
Figure 20D:
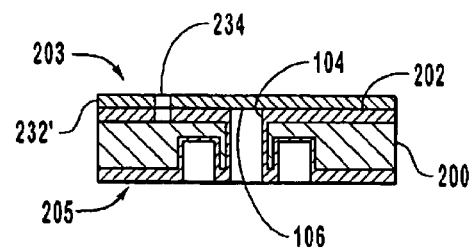

As shown in the cross-sectional view of FIG. 20C, a film of positive-working photoresist 232 is deposited over the silicon dioxide layer on the injection side 203 of the substrate 200. An area of the photoresist 232 corresponding to the electrical contact area between the electrode and the substrate 200 is selectively exposed through another mask by an optical lithographic exposure tool passing shortwavelength light, such as blue or near-ultraviolet at wavelengths of 365, 405, or 436 nanometers.

The photoresist 232 is then developed to remove the exposed area 234 of the photoresist such that the electrical contact area between the electrode and the substrate 200 is open to the underlying Silicon dioxide layer 202 while the unexposed areas remain protected by photoresist 232'. The exposed area 234 of the silicon dioxide layer 202 is then etched by a fluorine-based plasma with a high degree of anisotropy and selectivity to the protective photoresist 232' until the silicon substrate 200 is reached, as shown in the cross-sectional view of FIG. 20D.

Figure 20E:
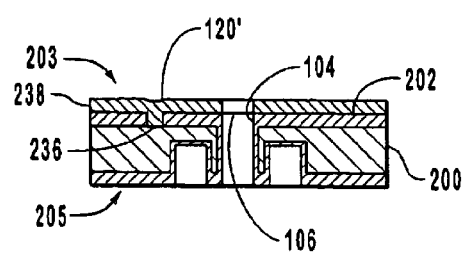

Referring now to the cross-sectional view of FIG. 20E. the remaining photoresist is then removed in an oxygen plasma or in an actively oxidizing chemical bath like sulfuric acid ($H_2SO_4$) activated with hydrogen peroxide ($H_2O_2$). Utilizing the patterned injection side silicon dioxide layer 202 as a mask, a high-dose implantation is made to form an implanted region 236 to ensure a low-resistance electrical connection between the electrode and the substrate 200. A conductive film 238 such as aluminum may be uniformly deposited on the injection side 203 of the substrate 200 by thermal or electron beam evaporation to form an electrode 120'.

In contrast to the formation of the conductive electrode on the ejection surface of the electrospray device, sputtering, in addition to thermal or electron-beam evaporation, may be utilized to form the conductive electrode on the injection surface. Because the nozzle is on the ejection rather than the injection side of the substrate, sputtering may be utilized to form the electrode on the injection side as the injection side electrode layer does not extend to the nozzle to create a physically continuous and thus electrically conductive path with the nozzle.

With the formation of the electrode on the injection surface of the electrospray device, sputtering may be preferred over evaporation because of its greater ability to produce conformal coatings on the sidewalls of the exposed area 234 etched through the silicon dioxide layer 202 to the substrate 200 to ensure electrical continuity and reliable electrical contact to the substrate 200.

For certain applications, it may be necessary to ensure electrical isolation between the substrate 200 and the fluid in the electrospray device by removing the conductive film from the region of the surface adjacent to the entrance orifice 106 on the injection side 203. The extent of the conductive film 238 which should be removed is irrespective of etching method and may be determined by the specific method utilized in creating the interface between the upstream fluid delivery system/sub-system and the injection side of the electrospray device. For example, a diameter of between approximately 0.2–2 mm of the conductive film 238 may be removed from the region surrounding the entrance orifice 106.

Figure 20F:
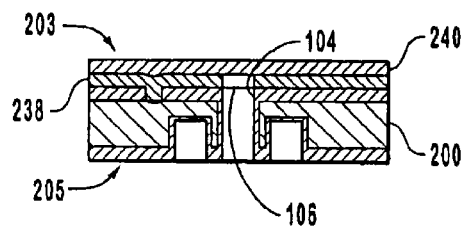
Figure 20G:
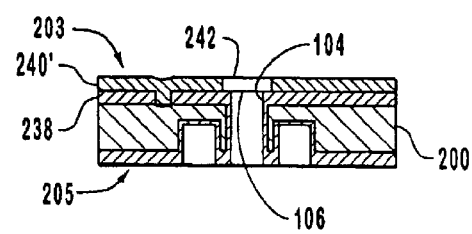

As shown in the cross-sectional view of FIG. 20F, another film of positive-working photoresist 240 is deposited over the conductive film 238 on the injection side 203 of the substrate 200. An area of the photoresist 240 corresponding to the region adjacent to the entrance orifice 106 on the injection side 203 is selectively exposed through another mask by an optical lithographic exposure tool passing short-wavelength light, such as blue or near-ultraviolet at wavelengths of 365, 405, or 436 nanometers.

The photoresist 240 is then developed to remove the exposed area 242 of the photoresist such that the region adjacent to the entrance orifice 106 on the injection side 203 is open to the underlying conductive film 238 while the unexposed areas remain protected by photoresist 240'. The exposed area 242 of the conductive film 238 is then etched by, for example, a chlorine-based plasma with a high degree of anisotropy and selectivity to the protective photoresist 240' until the silicon dioxide layer 203 is reached, as shown in the cross-sectional view of FIG. 20G.

The specific technique for etching the conductive film 238 may be determined by the specific conductive material deposited. For example, aluminum may be etched either in a wet chemical bath using standard aluminum etchant or in a plasma using reactive-ion etching (RIE) and chlorine-based gas chemistry. Utilization of standard wet aluminum etchant to etch an aluminum film may be preferred as such wet etching may facilitate the removal of any undesired conductive material deposited in the channel 104 via the entrance orifice 106. Further, although chlorine-based reactive-ion etching may be utilized, such etching may lead to aluminum corrosion if removal of the photoresist is delayed.

Forming the electrode on the injection surface for application of an electric potential to the substrate of the electrospray device may provide several advantages. For example, because the ability to uniformly coat photoresist on a surface is limited by nonplanar surface topology, coating photoresist on the much flatter injection side results in a more uniform and continuous photoresist film than coating photoresist on the ejection side. The uniformity and continuity of the photoresist film directly and positively impact the reliability and yield, at least in part because failure of photoresist coverage would allow subsequent etching of silicon dioxide in undesired locations during the etching of exposed areas 224, 234.

Another advantage of forming the electrode on the injection surface is the greater flexibility and reliability in the conductive material deposition step because the interior surfaces of the nozzle are not coated by the conductive material deposited onto the injection surface rather than onto the ejection surface of the electrospray device. As a result, sputtering may be utilized as a deposition technique to ensure conformal coating of the conductive material and electrical continuity from the surface to the substrate contact. Further, the provision of the electrode on the injection surface does not preclude the deposition and patterning of additional conductive electrodes on the ejection side to further modify the electric field line pattern to effect, for example, a steering and/or shaping of the electrospray, as such additional electrodes do not require electrical contact to the substrate.

The ability to form the electrode on the injection surface may also be advantageous in certain applications where physical constraints, such as in packaging, may dictate the need for injection-side rather than ejection-side electrical connection.

The above described fabrication sequence for the electrospray device 100 can be easily adapted to and is applicable for the simultaneous fabrication of a single monolithic system comprising multiple electrospray devices including multiple channels and/or multiple ejection nozzles embodied in a single monolithic substrate. Further, the processing steps may be modified to fabricate similar or different electrospray devices merely by, for example, modifying the layout design and/or by changing the polarity of the photomask and utilizing negative-working photoresist rather than utilizing positive-working photoresist.

Further, although the fabrication sequence is described in terms of fabricating a single electrospray device, the fabrication sequence facilitates and allows for massively parallel processing of similar devices. The multiple electrospray devices or systems fabricated by massively parallel processing on a single wafer may then be cut or otherwise separated into multiple devices or systems.

Interface or Integration of the Electrospray Device
Downstream Interface or Integration of the Electrospray Device The electrospray device 100 may be interfaced or integrated downstream to a sampling device, depending on the particular application. For example, the analyte may be electrosprayed onto a surface to coat that surface or into another device for purposes of conveyance, analysis, and/or synthesis. As described above with reference to FIG. 5, highly charged droplets are formed at atmospheric pressure by the electrospray device 100 from nanoliter-scale volumes of an analyte. The highly charged droplets produce gas-phase ions upon sufficient evaporation of solvent molecules which may be sampled, for example, through an orifice of an atmospheric pressure ionization mass spectrometer (API-MS) for analysis of the electrosprayed fluid.

Upstream Interface or Integration of the Electrospray Device

Figure 21A:
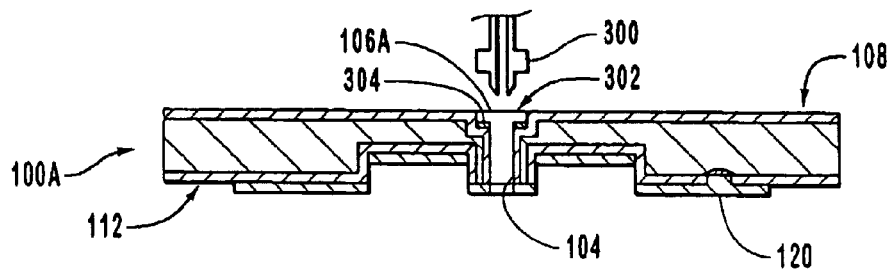
FIG. 21A shows a cross-sectional view of a piezoelectric pipette positioned at a distance from and for delivery of a fluid sample to the entrance orifice of the electrospray device.
Figure 21B:
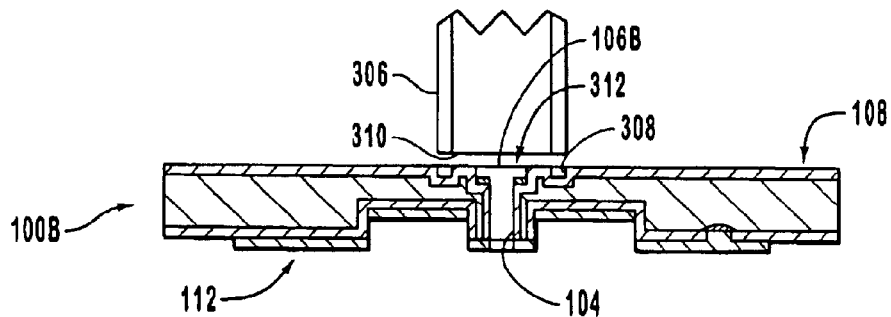
FIG. 21B shows a cross-sectional view of a capillary for delivery of a fluid sample to and prior to attachment to the entrance orifice of the electrospray device.
Figure 22:
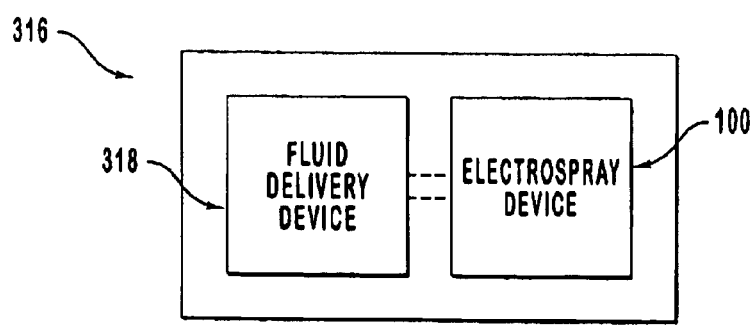
FIG. 22 shows a schematic of a single integrated system comprising an upstream fluid delivery device and an electrospray device having a homogeneous interface with the fluid delivery device.

Referring now to FIGS. 21–23, fluid may be delivered to the entrance orifice of the electrospray device in any suitable manner by upstream interface or integration with one or more fluid delivery devices, such as piezoelectric pipettes, micropipettes, capillaries and other types of microdevices. The fluid delivery device may be a separate component to form a heterogeneous interface with the entrance orifice of the electrospray device. Alternatively, the fluid delivery device may be integrated with the electrospray device to form a homogeneous interface with the entrance orifice of the electrospray device.

FIGS. 21A and 21B illustrate examples of fluid delivery devices forming heterogeneous interfaces with the entrance orifice of the electrospray device. Preferably, the heterogeneous interface is a non-contacting interface where the fluid delivery device and the electrospray device are physically separated and do not contact. For example, as shown in the cross-sectional view of FIG. 21A, a piezoelectric pipette 300 is positioned at a distance above the injection surface 108 of the electrospray device 100A. The piezoelectric pipette 300 deposits a flow of microdroplets, each approximately 200 pL in volume, into the channel 104 through the entrance orifice 106A. Preferably, the electrospray device 100A provides an entrance well 302 at the entrance orifice 106A for containing the sample fluid prior to entering the channel 104 particularly when it is desirable to spray a volume of fluid greater than the volume of the through-substrate channel 104 and continual supply of fluid is not feasible such as when using the piezoelectric pipette 300. The entrance well 302 preferably has a volume of 0.1 nL to 100 nL. Furthermore, to apply an electric potential to the fluid, an entrance well electrode 304 may be provided on a surface of the entrance well 302 parallel to the injection surface 108. Alternatively, a wire (not shown) may be positioned in channel 104 via the entrance orifice 106A. Preferably, some fluid is present in the entrance well 302 to ensure electrical contact between the fluid and the entrance well electrode 304.

Alternatively, the heterogeneous interface may be a contacting interface where a fluid delivery device is attached by any suitable method, such as by epoxy bonding, to the electrospray device to form a continuous sealed flow path between the upstream fluid source and the channel of the electrospray device. For example, FIG. 21B shows a cross-sectional view of a capillary 306 prior to attachment to the entrance orifice 106 of the electrospray device 100B. The injection surface 108 of the electrospray device 100B may be adapted to facilitate attachment of the capillary 306. Such features can be easily designed into the mask for the injection side of the substrate and can be simultaneously formed with the injection side portion of the channel during the etching performed on the injection-side.

For example, where the inner diameter of the capillary 306 is greater than that of the channel 104 and the entrance orifice 106, the electrospray device 100B preferably defines a region 308 recessed from the injection surface 108 to form a mating collar for mating and affixing with the capillary 306. Thus, capillary 306 may be positioned and attached in the recessed region 308 such that the exit orifice 310 portion of the capillary 302 is positioned around the entrance orifice 106. Further, the electrospray device 100B may optionally provide an entrance well 312 at the entrance orifice 106B for containing the sample fluid prior to entering the channel 104. Although not shown, if the outer diameter of the capillary is less than that of the channel and the entrance orifice, the capillary may be inserted into and attached to the entrance orifice of the electrospray device.

Referring now to the schematic of FIG. 22, rather than a heterogeneous interface, a single integrated system 316 is provided wherein an upstream fluid delivery device 318 forms a homogeneous interface with the entrance orifice (not shown) of an electrospray device 100. The system 316 allows for the fluid exiting the upstream fluid delivery device 318 to be delivered on-chip to the entrance orifice of the electrospray device 100 in order to generate an electrospray.

The single integrated system 316 provides the advantage of minimizing or eliminating extra fluid volume to reduce the risk of undesired fluid changes, such as by reactions and/or mixing. The single integrated system 316 also provides the advantage of eliminating the need for unreliable handling and attachment of components at the microscopic level and of minimizing or eliminating fluid leakage by containing the fluid within one integrated system.

The upstream fluid delivery device 318 may be a monolithic integrated circuit having an exit orifice through which a fluid sample can pass directly or indirectly to the entrance orifice of the electrospray device 100. The upstream fluid delivery device 318 may be a silicon microchip-based liquid separation device capable of, for example, capillary electrophoresis, capillary electrochromatography, affinity chromatography, liquid chromatography (LC) or any other condensed-phase separation methods. Further, the upstream fluid delivery device 318 may be a silicon, glass, plastic and/or polymer based device such that the electrospray device 100 may be chip-to-chip or wafer-to-wafer bonded thereto by any suitable method. An example of a monolithic liquid chromatography device for utilization in, for example, the single integrated system 316, is described below.

Electrospray Device for Sample Transfer of Combinatorial Chemistry Libraries Synthesized in Microdevices The electrospray device may also serve to reproducibly distribute and deposit a sample from a mother plate to daughter plate(s) by nanoelectrospray deposition. Electrospray device(s) may be etched into a microdevice capable of synthesizing combinatorial chemical libraries. At the desired time, the nozzle may spray a desired amount of the sample from the mother plate to the daughter plate(s). Control of the nozzle dimensions, applied voltages, and time of spraying may provide a precise and reproducible method of sample deposition from an array of nozzles, such as the generation of sample plates for molecular weight determinations by matrix-assisted laser desorption/ionization time-of-flight mass spectrometry (MALDI-TOFMS). The capability of transferring analytes from a mother plate to daughter plates may also be utilized to make other daughter plates for other types of assays, such as proteomic screening.

Figure 23A:
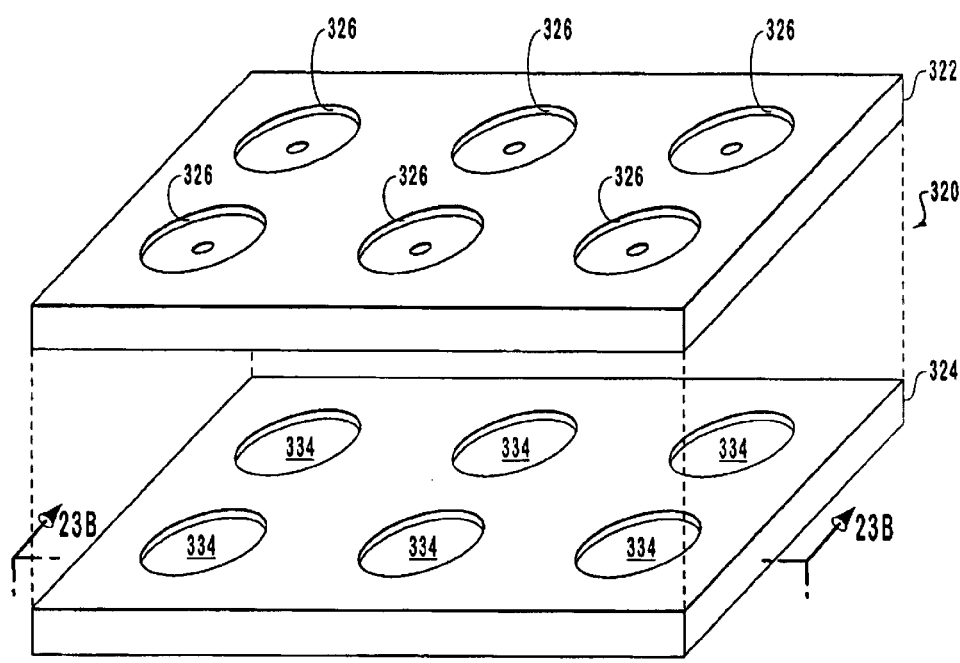
FIG. 23A shows an exploded perspective view of a chip-based combinatorial chemistry system comprising a reaction well block and a daughter plate.
Figure 23B:
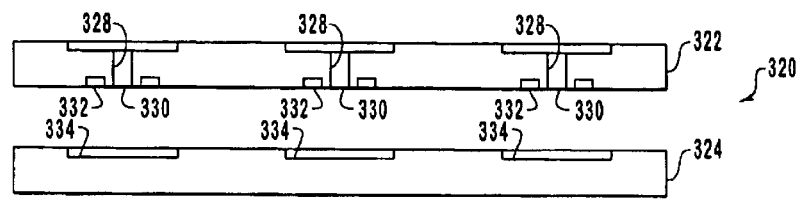
FIG. 23B shows a cross-sectional view of the chip-based combinatorial chemistry system of FIG. 23A taken along line 23B—23B.

FIGS. 23A and 23B show; respectively, an exploded perspective view and a cross-sectional view along line 23B—23B, of a chip-based combinatorial chemistry system 320 comprising a reaction well block or titer plate 322 and a receiving or daughter plate 324. The reaction well block 322 defines an array of reservoirs 326 for containing the reaction products from a combinatorially synthesized compound. The reaction well block 322 further defines channels 328, nozzles 330 and recessed portions 332 such that the fluid in each reservoir 326 may flow through a corresponding channel 328 and exit through a corresponding nozzle 330 in the form of an electrospray. The reaction well block 322 may define any number of reservoir(s) in any desirable configuration, each reservoir being of a suitable dimension and shape. The volume of a reservoir 326 may range from a few nanoliters up to several microliters and more preferably ranges between approximately 200 nL to 1 $\mu$L.

The reaction well block 322 may serve as a mother plate to interface to a microchip-based chemical synthesis apparatus such that the electrospray function of the reaction well block 322 may be utilized to reproducibly distribute discrete quantities of the product solutions to a receiving or daughter plate 324. The daughter plate 324 defines receiving wells 334 which correspond to each of the reservoirs 326. The distributed product solutions in the daughter plate 324 may then be utilized to screen the combinatorial chemical library against biological targets.

Illustration of an Electrospray Device Generating an Electrospray Spray

Figure 24A:
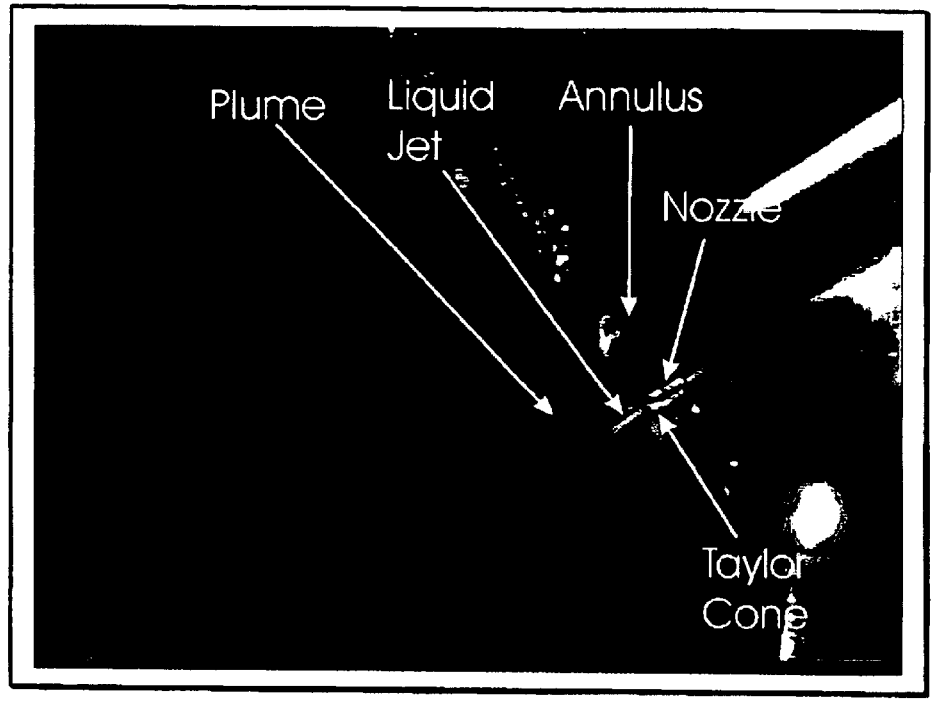
FIGS. 24A and 24B shows a real Taylor cone emanating from an integrated silicon chip-based nozzle.
Figure 24B:
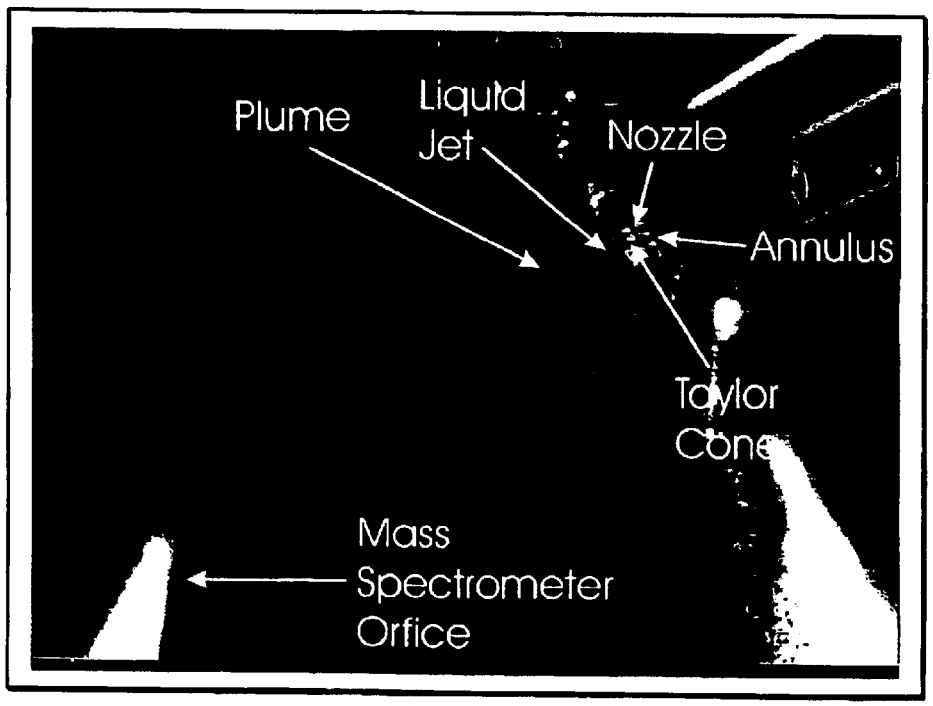
Figure 24C:
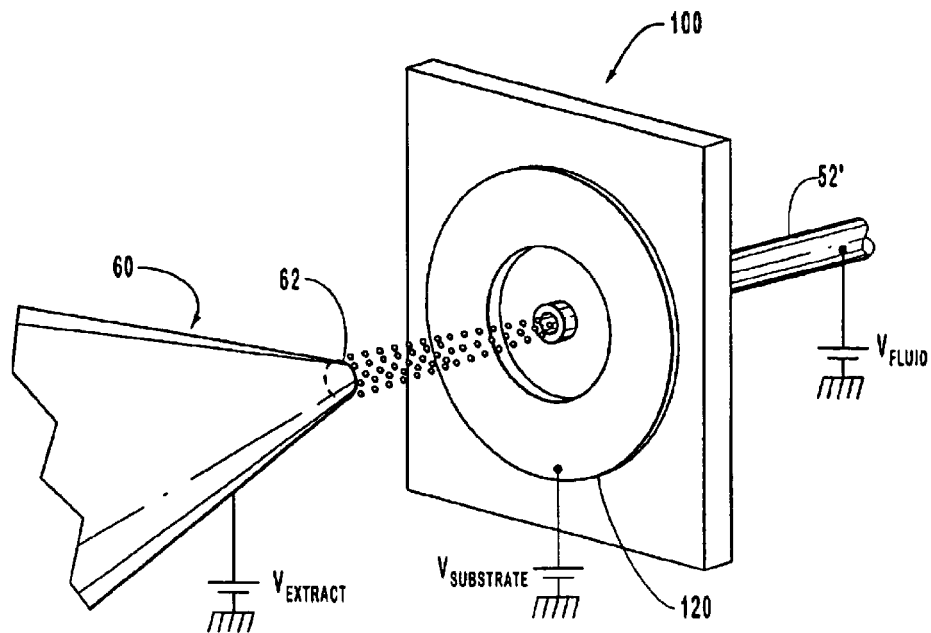
FIGS. 24C and 24D are perspective and side cross-sectional views, respectively, of the electrospray device and mass spectrometry system of FIGS. 24A and 24B.
Figure 24D:
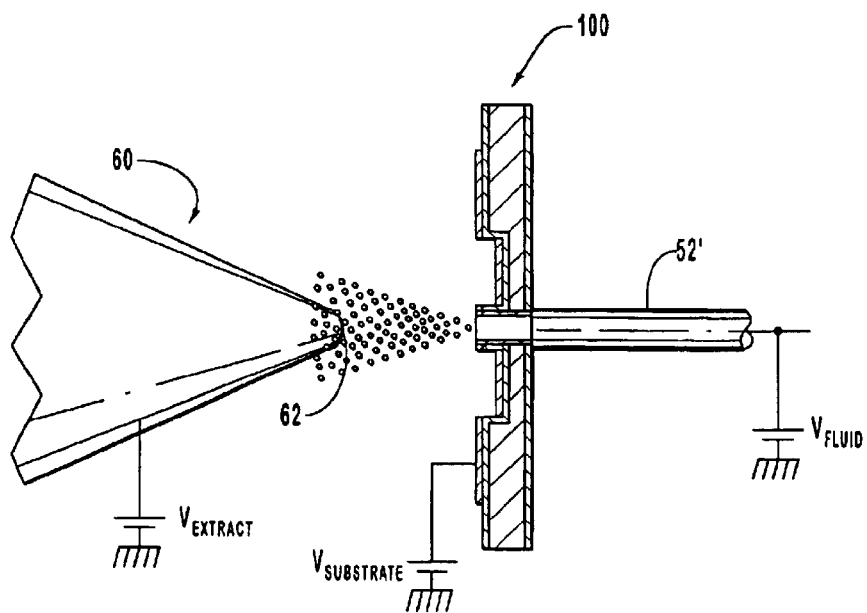

FIGS. 24A and 24B show color images of a real Taylor cone emanating from an integrated silicon chip-based nozzle. FIGS. 24C and 24D are perspective and side cross-sectional views, respectively, of the electrospray device and mass spectrometer system shown in FIGS. 24A and 24B. FIGS. 24A shows a chip-integrated electrospray device comprising a nozzle and a recessed portion or annulus, and a Taylor cone, liquid jet and plume of highly-charged electrosprayed droplets of methanol containing 10 $\mu$g/mL polypropylene glycol 425 (PPG425) containing 0.2% formic acid. FIG. 24B shows an ion-sampling orifice of a mass spectrometer in addition to the electrospray device.

The electrospray device 100 is interfaced upstream with a pipette 52'. As shown in the upper right corner of each of FIGS. 24A and 24B and in FIGS. 24C and 24D, the tip of the pipette 52' is press-sealed to the injection side of the electrospray device 100. The electrospray device 100 has a 10 μm diameter entrance orifice on the injection side, a 30 μm inner diameter and a 60 μm outer diameter nozzle, a 15 μm nozzle wall thickness and a 150 μm nozzle depth. The recessed portion or the annulus extends 300 μm from the outer diameter of the nozzle. The voltage applied to the fluid $V_{fluid}$ introduced to the electrospray device and thus the nozzle voltage is 900 V. The voltage applied to the substrate $V_{substrate}$ and thus the electrospray device is 0 V. The voltage applied to the mass spectrometer which also serves as an extracting electrode $V_{extract}$ is approximately 40 V. The liquid sample was pumped using a syringe pump at a flow of 333 nL/min through the pipette tip pressed-sealed against the injection side of the electrospray device. The nozzle is approximately 5 mm from the ion-sampling orifice 62 of the mass spectrometer 60. The ion-sampling orifice 62 of the mass spectrometer 60 generally defines the acceptance region of the mass spectrometer 60. The mass spectrometer for acquiring the data was the LCT Time-Of-Flight mass spectrometer of Micromass, Inc.

Figure 24E:
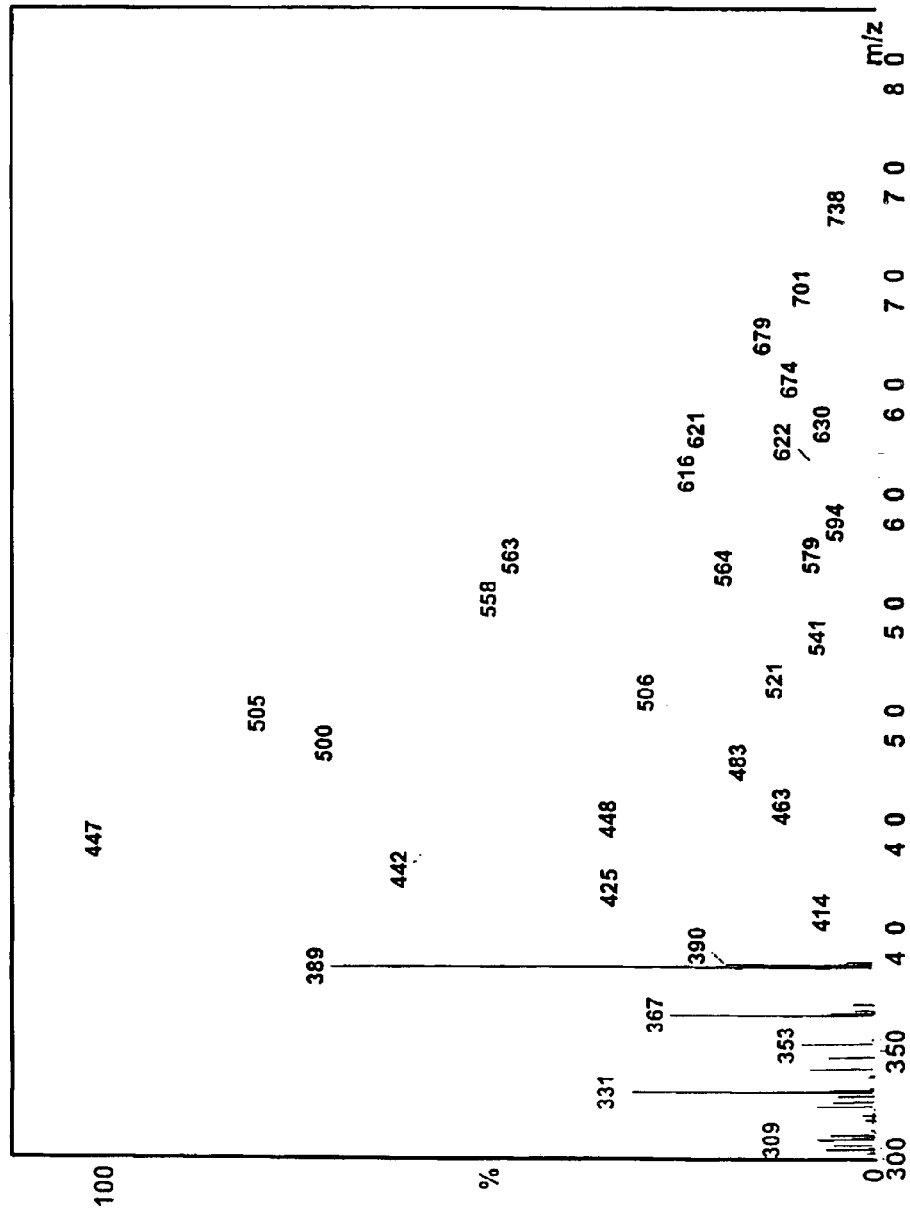
FIG. 24E shows a mass spectrum of 1 µg/mL PPG425 in 50% water, 50% methanol containing 0.1% formic acid, 0.1% acetonitrile and 2 mM ammonium acetate, collected at a flow rate of 333 nL/min.

FIG. 24E shows a mass spectrum of 1 μg/mL PPG425 in 50% water, 50% methanol containing 0.1% formic acid, 0.1% acetonitrile and 2 mM ammonium acetate. The data were collected at a flow rate of 333 nL/min.

Liquid Chromatography Device

Figure 25A:
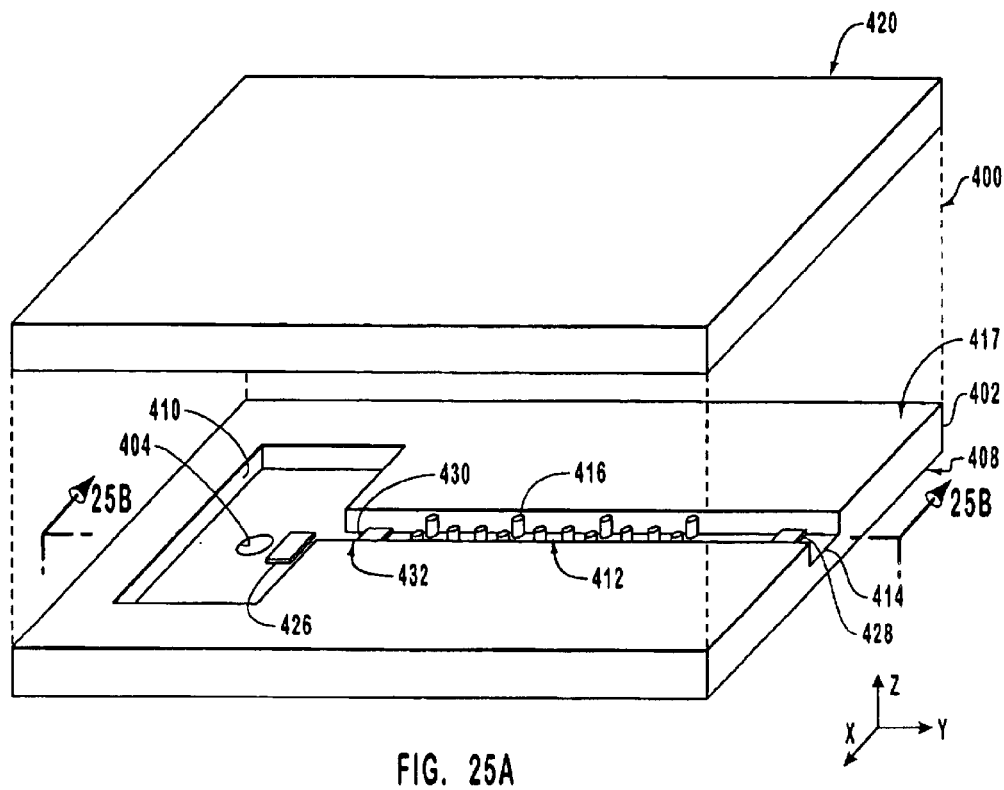
FIG. 25A shows an exploded perspective view of a liquid chromatography device for homogeneous integration with the electrospray device of the present invention.
Figure 25B:
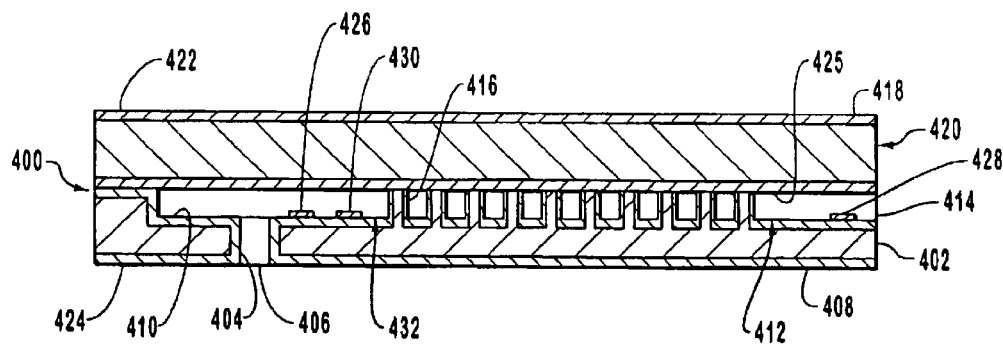
FIG. 25B shows a cross-sectional view of the liquid chromatography device of FIG. 25A taken along line 25B—25B.

In another aspect of the invention shown in the exploded perspective and cross-sectional views of FIGS. 25A and 25B, respectively, a silicon-based liquid chromatography device 400 generally comprises a silicon substrate or microchip 402 defining an introduction channel 404 through the substrate 402 extending between an entrance orifice 406 on a first surface 408 and a fluid reservoir 410, a separation channel 412 extending between the reservoir 410 and an exit orifice 414, a plurality of separation posts 416 along the separation channel 412, and a cover 420 to provide an enclosure surface adjacent the cover 420 for the reservoir 410 and the separation channel 412 adjacent the cover 420.

The plurality of separation posts 416 extends from a side wall of the separation channel 412 in a direction perpendicular to the fluid flow though the separation channel 412. Preferably, one of the ends of each separation post 416 does not extend beyond and is preferably coplanar or level with the second surface 417. The separation channel 412 is functionally similar to the liquid chromatography column in that component separation occurs in the separation channel 412 where the plurality of separation posts 416 perform the liquid chromatography function. Component separation occurs through the interaction of the fluid flowing through the separation channel 412 wherein the columnar separation posts 416 provides the large surface area. The surfaces of the separation channel 412 and the separation posts 416 are preferably provided with an insulating layer to insulate the fluid in the separation channel 412 from the substrate 402. Specifically, the separation posts 416 are preferably oxidized silicon posts which may be chemically modified using known techniques in order to optimize the interaction of the components of the sample fluid with the stationary phase, the separation posts 416. In one embodiment, the separation channel 412 extends beyond the separation posts 416 to the edge of the substrate 402 and terminating as the exit orifice 414.

The introduction channel, 404, the separation channel 412, the reservoir 410 and the separation posts 416 may have any suitable cross-sectional shapes such as circular and/or rectangular. Preferably, the separation posts 416 have the same cross-sectional shapes and sizes but may nonetheless have different cross-sectional shapes and/or sizes.

The liquid chromatography device 400 further comprises a layer of silicon dioxide 422 over the surfaces of the substrate of the cover 420 and a layer of silicon dioxide 424 over the surfaces of the substrate 402. The silicon dioxide layers 422, 424 electrically isolate a fluid contained in the reservoir 410 and the separation channel 412 from the substrate 402 and the substrate of the cover 420. The silicon dioxide layers 422, 424 are also relatively inactive and thus less likely to interact with fluids in the reservoir 410 and the separation channel 412 than bare silicon.

Depending on the specific application, the substrate 402 may provide a surface on which one or more conductive electrodes in electrical contact with the fluid in the device 400 may be formed. For example, a reservoir electrode 426 and/or an exit electrode 428 may be provided on the second surface 417 of the substrate 402 such that a corresponding electrode would be in electrical contact with fluid in the reservoir 410 and near the exit orifice 414, respectively. A filling electrode 430 may also be provided on the second surface 417 of the substrate 402 such that it would be in electrical contact with fluid in the unpopulated portion 432 of the separation channel 412 between the reservoir 410 and the first occurrence of separation posts 416. The shape, size and location along the fluidic flow path of each electrode on the substrate 402 may be determined by design considerations such as the distance between adjacent electrodes. Further, any or all of the electrodes may be alternatively or additionally formed on the bonding surface 425 of the cover 420. For example, the filling electrode 430 may be alternatively positioned such that it would be in electrical contact with fluid in the separation channel 412 adjacent the reservoir 410. Further, additional electrodes may be provided, for example, to create an arbitrary electrical potential distribution along the fluidic flow path.

Providing two or more of the reservoir, filling and exit electrodes along with electrical isolation of the fluid sample in the device 400 from the substrate 402 and the substrate of the cover 420 allows for the application and sustenance of different (or same) electric potentials at two or more different locations along the fluidic path. The difference in electric potentials at two or more different locations along the fluidic path causes fluidic motion to occur between the two or more locations. Thus, these electrodes may facilitate the filling of the reservoir 410 and/or the driving of the fluid through the separation channel 412.

Further, through appropriate layout design and fabrication processes, the substrate 402 and/or the cover 420 may also provide additional functionalities such as pre-conditioning of the fluid prior to delivery into the reservoir 410, and/or conveying, analyzing, and/or otherwise treating fluidic samples exiting from the separation channel 412. The cover 420 may provide such additional functionality on either or both surfaces and/or the bulk of the cover 420.

The cover 420 may comprise a substrate 418 comprising silicon or any other suitable material, such as glass. plastics and/or polymers. The specific material for the cover 420 may depend upon, for example, whether direct observation of a fluoresced fluid is desired such that glass may be more desirable and/or the consideration of the ease of fabrication of the cover 420 by utilizing similar processing techniques as for the substrate 402 such that silicon may be more desirable. The cover 420 may be bonded or otherwise affixed to form a hermetic seal between the substrate 402 and the cover 420 in order to ensure the appropriate level of fluid containment and isolation. For example, several methods of bonding silicon to silicon or glass to silicon are known in the art, including anodic bonding, sodium silicate bonding, eutectic bonding, and fusion bonding. The specific hermetic bonding method may depend on various factors such as the physical form of the surfaces of the substrate 402 and the cover 420 and/or the application and functionality of the integrated system and/or the liquid chromatography device 400.

Dimensions of the liquid chromatography device 400 may be determined according to various factors such as the specific application, the layout design as well as the device with which it is to be interfaced or integrated. The surface dimensions, i.e. the dimensions in the X and Y directions, of the elements of the liquid chromatography device 400 may be determined by layout design and through the corresponding photomasks used in fabrication. The depth or height, i.e. the dimension in the Z direction, of the elements of the liquid chromatography device 400 may be determined by the etch processes during fabrication, as described below. The depth or height of the elements is independent of the surface dimensions to a first-order approximation although the aspect ratio limitations of the reactive-ion etch places constraints on the etch depth, particularly with the small surface openings in the channel 412 between the separation posts 416.

Further, the size, number, cross-sectional shape, spacing and placement of the separation posts 416 may also be determined by layout design to achieve the desired flow rate and to prevent low-resistance lines of sight within the separation channel 412 to ensure adequate fluid-surface interaction. Each separation post 416 may have the same or different characteristics such as size and/or cross-sectional shape. The cross-sectional shape of the posts may be chosen in layout design to optimize fluid/boundary layer interactions at the post surfaces. The separation posts 416 may be placed in any desired pattern in the separation channel 412, such as periodic, semi-periodic, or random. Close spacing of the separation posts 416 may be desirable for maximization of the surface interactions with the fluid. Similarly, minimizing the cross-sectional area of the separation posts 416 may permit placement of greater number in the separation channel 412. However, the reduction of the cross-sectional area of the separation posts 416 is limited by the resulting reduction in the mechanical stability necessary during processing.

Control of the size, number, cross-sectional shape, spacing and placement of the separation posts 416 provides advantages over traditional liquid chromatography as the traditional separation column packing materials have undesired dispersion in size distribution as well as random spacing variations.

In one currently preferred embodiment, the substrate 402 of the liquid chromatography device 400 is approximately 250–600 $\mu$m in thickness, the separation channel 412 has a depth of approximately 10 $\mu$m, the rectangular reservoir 410 is approximately 1000 $\mu$m by 1000 $\mu$m resulting in a volume of approximately 10 nL. The depth of the reservoir 410 and the separation channel 412 is limited by the height of the separation posts 416 which is in turn limited by the maximum etch aspect ratio. The nearest-neighbor spacing of the separation posts 416 is preferably less than approximately 5 $\mu$m. The dimensions of the reservoir 410 determine the volume of the fluid sample which can be used for the liquid chromatography separation and, as is evident, through the independent control of surface dimensions and the depth, the reservoir 410 may be designed to have any desired volume. Preferably, the diameter of the entrance orifice 406 is 100 $\mu$m or less such that the fluid surface tension would be sufficient to maintain the fluid in the reservoir 410 to prevent leakage therefrom.

The silicon-based liquid chromatography device 400 reduces the size of a typical liquid chromatography device by nearly two orders of magnitude. The dimensional scaling may provide the advantage of significantly reducing the mass of the analyte and/or the volume of the fluid sample required for accurate analysis. Further, by reducing a macroscopic separation column and its packing materials to a monolithic device, the liquid chromatography device 400 can be a component of an on-chip integrated system.

Further, all features such as the reservoir, the separation channel and the separation posts are recessed from the substrate 402. The portion of the substrate 402 exterior to the reservoir and the separation channel thus serves to physically protect the separation posts from casual abrasion and stress fracture in handling and subsequent bonding of the substrate 402 and the cover 420. Because the posts are integral with the substrate, the posts are inherently stable and thus allow for the use of a pressurized system without the risk of damage to the stationary phase which may otherwise result with the use of conventional packing materials in conventional high-performance liquid chromatography systems.

An upstream fluid delivery system, such as a micropipette, piezoelectric pipette or small capillary, may be press-sealed onto the exterior surface of the liquid chromatography device 400 such that the pipette or capillary is concentric with the entrance orifice 406. Optionally, the liquid chromatography device may provide a collar (not shown) to facilitate the mating and affixing of the fluid delivery device to the liquid chromatography device similar to the mating collar of the electrospray device as discussed with reference to FIG. 21B.

To operate the liquid chromatography device 400, the fluid reservoir 410 may first be filled with a sample fluid by injecting the fluid from a fluid delivery device through the introduction channel 404 via the entrance orifice 406. Any suitable fluid delivery device such as a micropipette, a piezoelectric pipette or a small capillary may be utilized. The volume of the sample fluid injected into the liquid chromatography device 400 may be up to approximately the volume of the reservoir 410 plus a relatively small volume remaining in the introduction channel 404.

The filling of the reservoir 410 may be facilitated by applying an appropriate potential voltage difference between the reservoir electrode 426 and the filling electrode 430, such as approximately 1000 V/cm of introduction channel 404. In particular, a volume of the fluid is first introduced into the reservoir 410 through the introduction channel 404 via the entrance orifice 406 to coat or prime the surfaces of the reservoir 410 and the introduction channel 404 by capillary action to allow for electrical contact between the fluid and the reservoir and filling electrodes 426, 430. Where the filling electrode 430 is positioned in a portion of the separation channel 412 unpopulated by separation posts 416, the filling electrode 430 also facilitates the filling of the portion of the channel 412 between the reservoir 410 and the filling electrode 430.

After filling the reservoir 410 with an appropriate volume of the sample fluid, any suitable method may then be utilized to drive the fluid from the reservoir 410 into the separation channel 412. For example, the fluid may be driven from the filled reservoir 410 through the separation channel 412 by applying hydrostatic pressure to the reservoir 410 via the entrance orifice 406.

Alternatively or additionally, the fluid may be driven through the separation channel 412 by applying a suitable electrokinetic potential voltage difference between the reservoir electrode 426 and the exit electrode 428 to generate electrophoretic or electroosmotic fluidic motion. Preferably, the electric potential difference is approximately 1000 V/cm of separation channel length. Of course, any other suitable methods of inducing fluidic motion may be utilized. Pressure-driven and voltage-driven flow effect different separation efficiencies. Thus, depending upon the application, one or both may be utilized.

Figure 26:
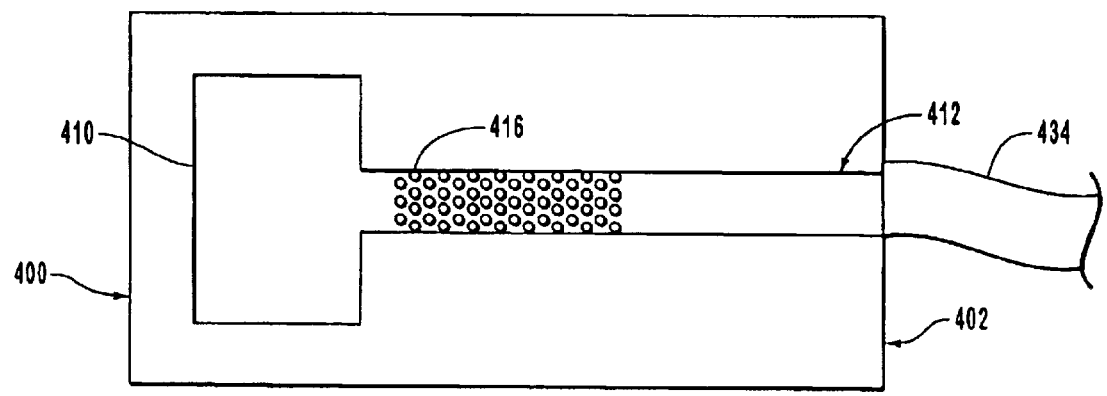
FIG. 26 shows a plan view of a liquid chromatography device having an exit orifice forming an off-chip interconnection with an off-chip device.
Figure 27:
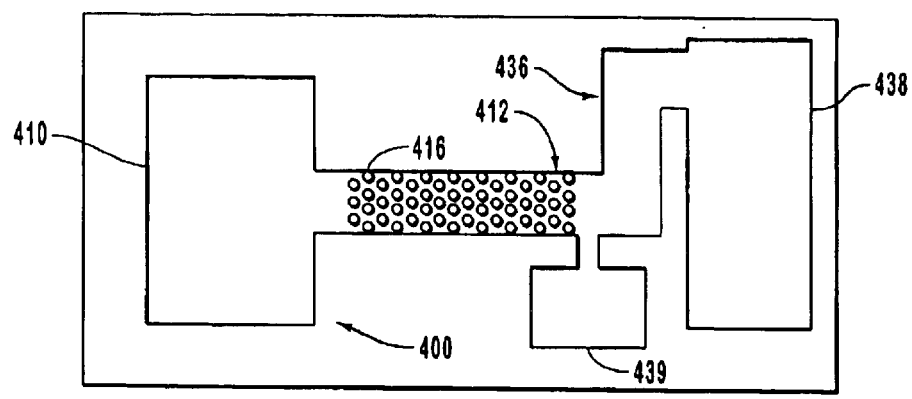
FIG. 27 shows a plan view of a liquid chromatography device having an exit orifice forming an on-chip interconnection with another on-chip device.

Fluid then exits from the separation channel 412 through the exit orifice 414 to, for example, a capillary 434, which has an off-chip interconnection with the exit orifice 414, as shown in FIG. 26. Alternatively, as shown in FIG. 27, the liquid chromatography device 400 may perform separation on the fluid from reservoir 410 such that selected analytes from the separation performed by posts 416 passes through unpopulated channel 436 to another on-chip device 438, such as for analysis and/or mixing, while the remainder of the fluid is directed to the waste reservoir 439. The unpopulated channel 436 may be a mere continuation of the separation channel 412 of the liquid chromatography device 400 or a channel separate from the separation channel 412.

Two or more fluid samples may be driven through the liquid chromatography device 400 by successively filling the reservoir and driving the fluid through the separation channel 412. For example, in certain applications, it may be desirable or necessary to first coat the surfaces of the separation posts 416 with one or more reagents and then pass an analyte sample over the conditioned separation posts 416.

Figure 28:
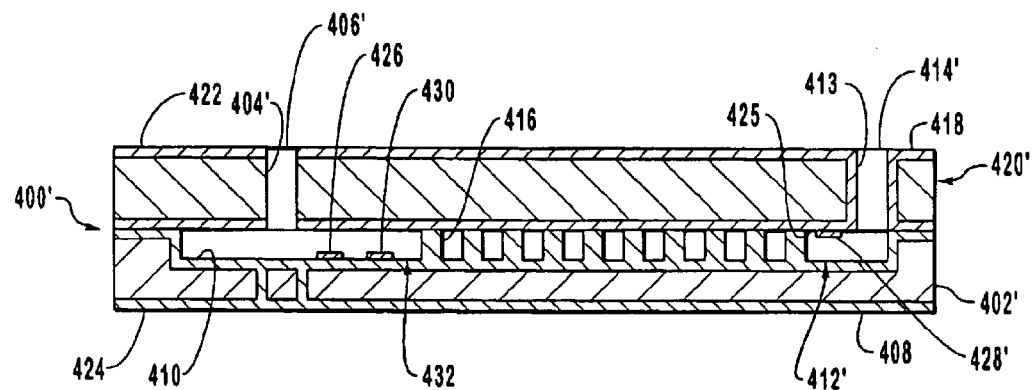
FIGS. 28–29 show cross-sectional views of liquid chromatography devices having alternative configurations.

Various modifications may be made to the liquid chromatography device describe above. For example, as shown in FIG. 28, rather than defining the entrance orifice and the introduction channel in the substrate, the liquid chromatography device 400' may provide an introduction channel 404' in the cover 420' such that the entrance orifice 406' is defined on an exterior surface of the cover 420'. Further, the cover 420' may define an exit channel 413 between an exit orifice 414' defined on an exterior surface of the cover 420' and a separation channel 412' which terminates within the substrate 402'.

Figure 29:
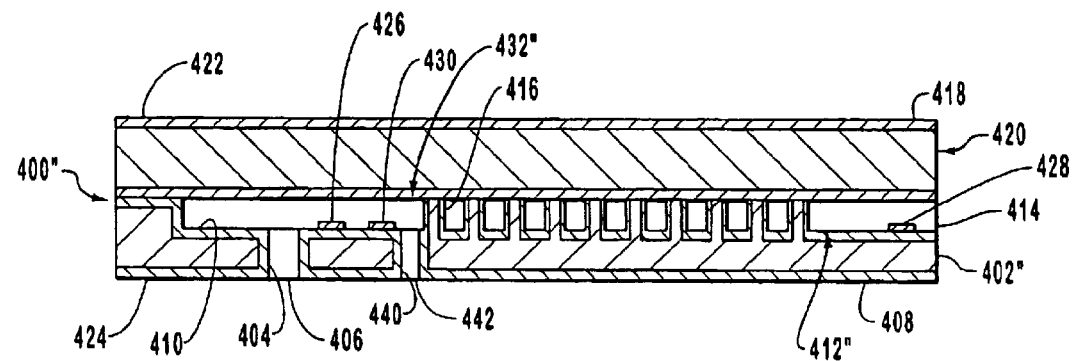

In another variation, an additional introduction channel 440 and entrance orifice 442 may be defined in the substrate 402", as shown in FIG. 29, or in the cover (not shown). The additional introduction channel 440 introduces fluid to the separation channel 412" such that the fluid from the additional introduction channel 440 intersects the path of fluid flow from the reservoir 410 through the unpopulated portion 432" of the separation channel 412". The fluid reservoir 410 may be utilized as a buffer for an eluent and the additional introduction channel 440 may be utilized to introduce the fluid sample to the separation channel 412". Further, the additional entrance orifice 442 may be utilized to introduce several fluid samples in succession into the separation channel 412". For example, in certain applications, it may be necessary to first coat the surfaces of the separation posts 416 with one reagent and then pass an analyte over the conditioned surfaces of the separation posts 416.

Referring now to FIGS. 30–35, although the liquid chromatography device has been described as comprising a single reservoir and a single separation channel, the monolithic liquid chromatography device may be easily adapted and modified to comprise multiples of the liquid chromatography device and/or multiple entrance orifices, exit orifices, reservoirs and/or separation channels. In each of the variations, any or all of the reservoir(s), separation channel (s), and separation posts may have different dimensions and/or shapes.

Figure 30:
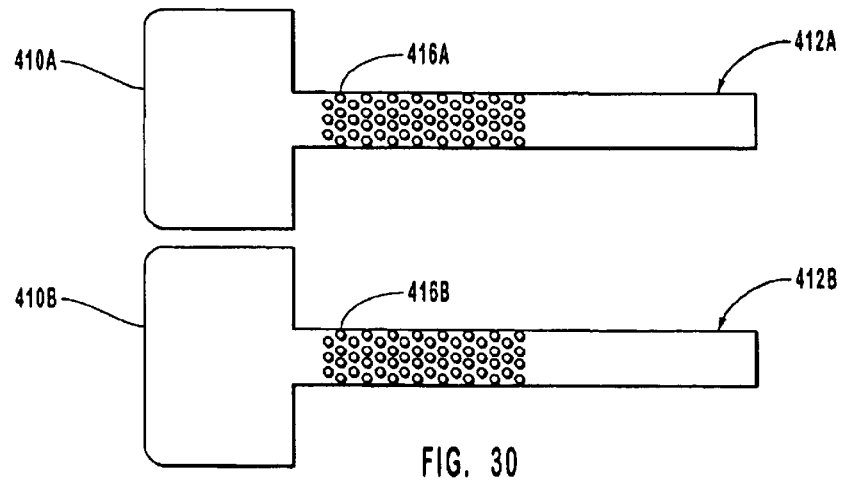
FIGS. 30–35 show plan views of liquid chromatography devices having alternative configurations.

For example, multiple reservoir-separation channel combinations may be provided on a single chip. In particular, as shown in FIG. 30, a reservoir 410A may feed into a separation channel 412A having separation posts 416A and another reservoir 410B may feed into another separation channel 412B having separation posts 416B.

Figure 31:
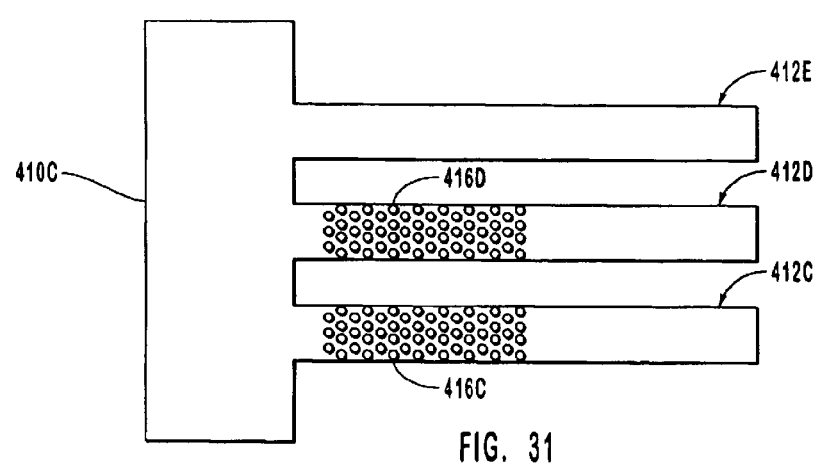

In another variation as shown in FIG. 31, a single reservoir 410C may feed multiple separation channels 412C, 412D. Each of separation channels 412C, 412D may have therein separation posts 416C, 416D, respectively, which may have the same or different properties, such as number, size and shape. Another channel 412E may be provided as a null channel completely unpopulated by separation posts. The output from the null channel 412E may be utilized as a basis of comparison to the output from the separation channel(s) populated by separation posts. Alternatively, all of the channels 412C, 412D, 412E may be separation channels having separation posts.

Figure 32:
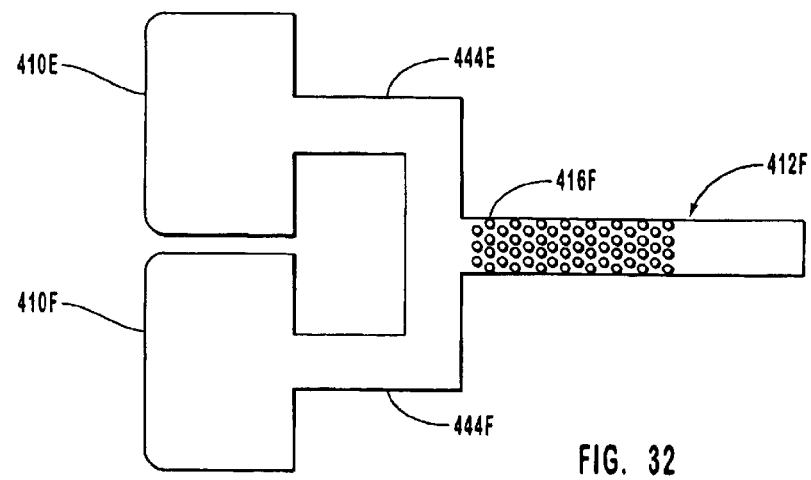

Referring now to FIG. 32, fluid from multiple reservoirs 410E and 410F may feed into a single separation channel 412F via connecting channels 444E, 444F, respectively. The connecting channels 444E, 444F are preferably unpopulated by separation posts to facilitate the mixing of the fluid samples from the reservoirs 410E, 410F prior to passage through the separation channel 412F. The mixing of samples may be utilized to condition the primary sample of interest prior to separation or to effect a reaction between the samples prior to passage through the populated portion of the separation channel 412F. Alternatively, fluid such as a conditioning fluid from one reservoir 410E may flow through the separation channel 412F in order to condition the surfaces of the separation posts 416F prior to the passage of the other sample such as an analyte sample from the other reservoir 410F. Although the separation posts 416F are shown as having different cross-sections, separation posts 416F may have the same size and cross-sectional shape.

Figure 33:
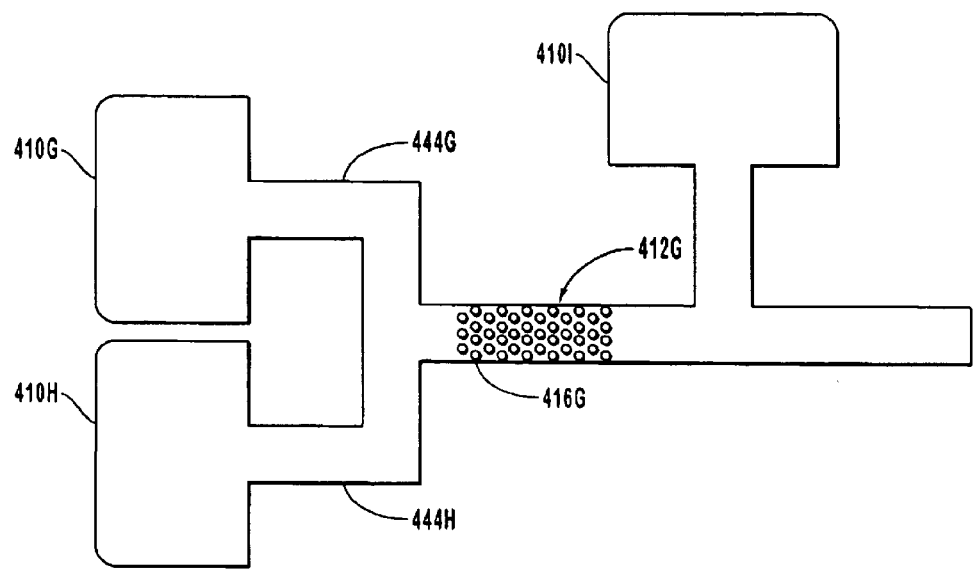
Figure 34:
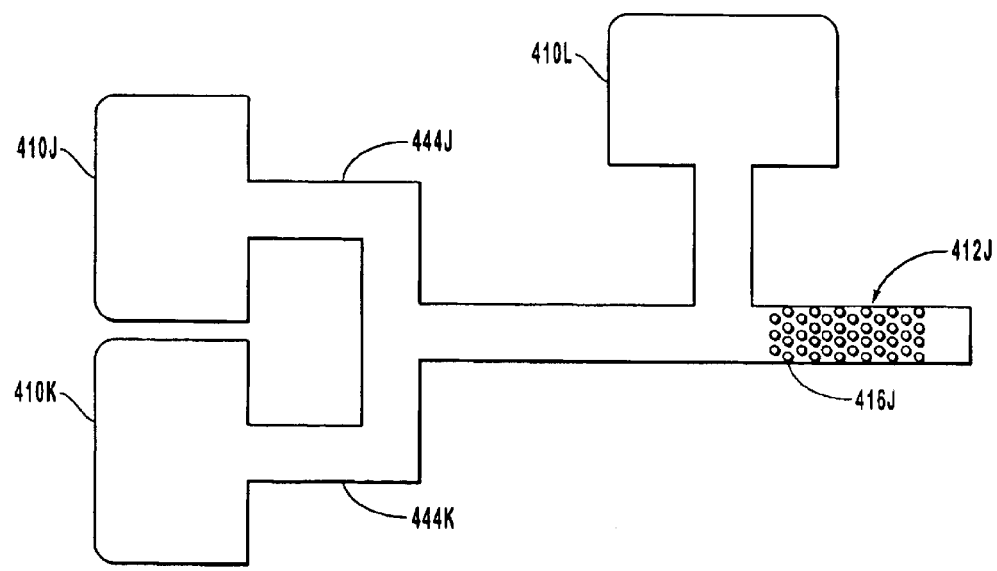

Alternatively, in addition to having fluid from multiple reservoirs feed into a single separation channel via connecting channels, fluid from another reservoir may be introduced to the fluid flow along the separation channel, before and/or after the fluid has passed through the populated portion of the separation channel. For example, FIG. 33 shows that the fluid from multiple reservoirs 410G, 410H may be fed into a single separation channel 412G via connecting channels 444G, 444H, respectively, and fluid from another reservoir 410I may be introduced to the fluid flow along the separation channel 412G after the fluid has passed the separation posts 416G. FIG. 34 shows that the fluid from multiple reservoirs 410J, 410K may be fed into a single separation channel 412J via connecting channels 444J, 444K, respectively, and fluid from another reservoir 410L may be introduced to the fluid flow along the separation channel 412J prior to the fluid passing the separation posts 416J.

For devices having multiple reservoirs and/or multiple channels, separate electrodes may be provided for each reservoir and/or for each channel, for example, in the unpopulated portion of the channel upstream from the separation posts and/or near the exit of the channel. Such provision of separate electrodes allow for the separate and independent control of the fluidic flow for filling each reservoir and/or for driving the fluid through the separation channel.

The electric control may be simplified by having one common reservoir electrode, one common filling electrode, and/or one exit electrode among the multiple reservoirs and/or multiple channels. For example, each of the multiple reservoirs may be separately filled by applying a first voltage to the common reservoir electrode and a second voltage, different from the first voltage, to the filling electrode corresponding to the reservoir to be filled while applying the first voltage to each of the other filling electrodes. As is evident, the multiple reservoirs may be simultaneously filled by applying a first voltage to the common reservoir electrode and a second, different voltage to each of the filling electrodes. Similarly, fluid may be separately driven through each of the multiple channels by applying a third voltage to the common reservoir electrode while applying a fourth voltage, different from the third voltage, to the exit electrode corresponding to the channel through which fluid is to be driven and the third voltage to each of the other exit electrodes.

Figure 35:
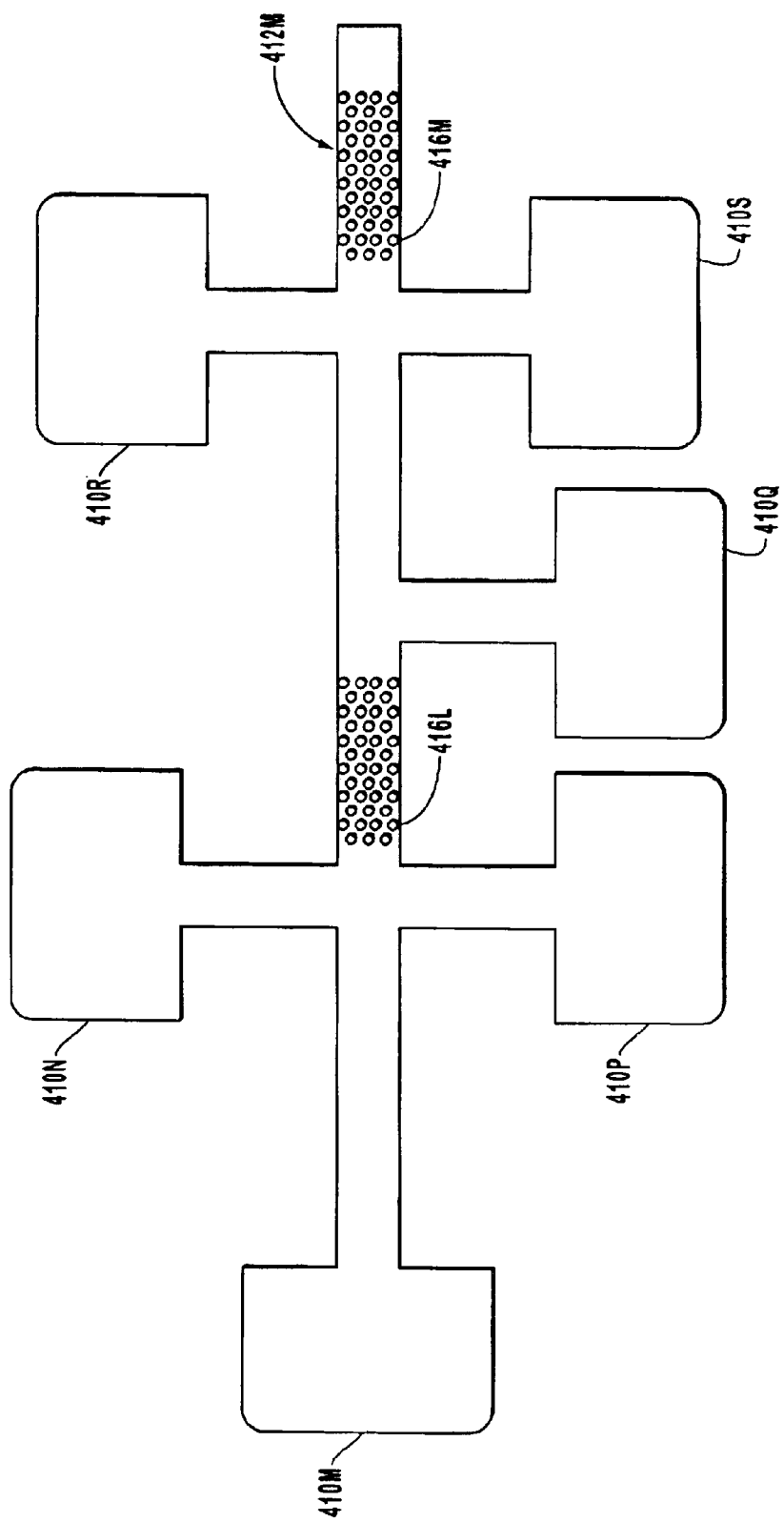

In yet another variation shown in FIG. 35, in addition to a sample reservoir 410M and separation posts 416M, a plurality of posts 416L may be provided in a channel 412M upstream from the separation posts 416M for providing additional functionality such as solid-phase extraction (SPE) for sample pretreatment. The SPE posts 416L may be the same, similar to or different from the separation posts 416M simply by varying the layout design. The SPE posts 416L may provide surface functionality different from that of the separation posts 416M. Alternatively, rather than providing a sample reservoir, an introduction channel (not shown) may be utilized to introduce a fluidic sample directly in the channel 412M by allowing direct injection of the sample therein. Further, reservoirs 41 ON, 410P may be provided to contain fluidic buffers necessary for sample pretreatment upstream of the posts 416L. For example, an eluent reservoir may be provided for eluting analytes and a wash reservoir may be provided for sample cleanup.

After the fluid samples pass the SPE posts 416L, waste products from, for example, the solid-phase extraction process may be directed into a waste reservoir 410Q. In particular, during the SPE process, voltage differences may be applied between or amongst reservoirs 410M, 410N, 410P, and 410Q such that a portion of the fluid from reservoirs 410M, 410N is directed to waste reservoir 410Q while the remaining portion of the fluid from reservoir 410M remain on the SPE posts 416L. Material may then be washed off of the SPE posts 416L by directing fluid from, for example, reservoir 410P through channel 412M for separation of the extracted material by separation posts 416M. Additional reservoirs 410R, 410S downstream of the waste reservoir 410Q and upstream of the separation posts 416M may be provided to contain gradient elution of analytes in one reservoir and a diluent in the other reservoir. Gradient elution facilitates chromatography by changing the mobile phase composition, i.e. the polarity to facilitate analyte interactions with the stationary phase, and thus facilitate separation of the analytes. In addition, the diluent provides the correct polarity of the solution for the next separation.

Liquid Chromatography Device Fabrication Procedure

The fabrication of the liquid chromatography device of the present invention will now be explained with reference to FIGS. 36A–46B. The liquid chromatography device is preferably fabricated as a monolithic silicon micro device utilizing established, well-controlled thin-film silicon processing techniques such as thermal oxidation, photolithography, reactive-ion etching (RIE), ion implantation, and metal deposition. Fabrication using such silicon processing techniques facilitates massively parallel processing of similar devices, is time- and cost-efficient, allows for tighter control of critical dimensions, is easily reproducible, and results in a wholly integral device, thereby eliminating any assembly requirements. Manipulation of separate components and/or sub-assemblies to build an liquid chromatography device with high reliability and yield is not desirable and may not be possible at the micrometer dimensions required for efficient separation.

Further, the fabrication sequence may be easily extended to create physical aspects or features to facilitate interfacing, integration and/or connection with devices having other functionalities or to facilitate integration with a fluid delivery subsystem to create a single integrated system. Consequently, the liquid chromatography device may be fabricated and utilized as a disposable device, thereby eliminating the need for column regeneration and eliminating the risks of sample cross-contamination.

Figures 36A, 36B:
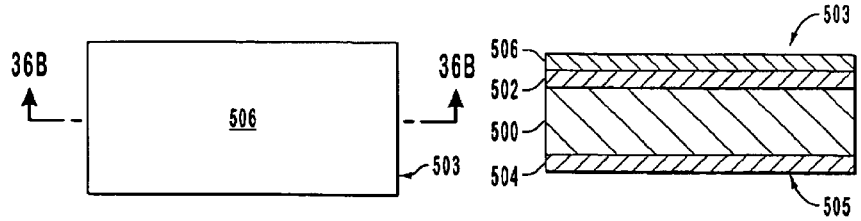

Referring to the plan and cross-sectional views, respectively, of FIGS. 36A and 36B, a silicon wafer separation substrate 500, double-side polished and approximately 250–600 $\mu$m in thickness, is subjected to an elevated temperature in an oxidizing ambient to grow a layer or film of silicon dioxide 502 on the reservoir side 503 and a layer or film of silicon dioxide 504 on the back side 505 of the separation substrate 500. Each of the resulting silicon dioxide layers 502, 504 has a thickness of approximately 1–2 $\mu$m. The silicon dioxide layers 502, 504 provide electrical isolation and also serve as masks for subsequent selective etching of certain areas of the separation substrate 500.

A film of positive-working photoresist 506 is deposited on the silicon dioxide layer 502 on the reservoir side 503 of the separation substrate 500. Certain areas of the photoresist 506 corresponding to the reservoir, separation channel and separation posts which will be subsequently etched are selectively exposed through a mask by an optical lithographic exposure tool passing short-wavelength light, such as blue or near-ultraviolet at wavelengths of 365, 405, or 436 nanometers.

Figures 37A, 37B:
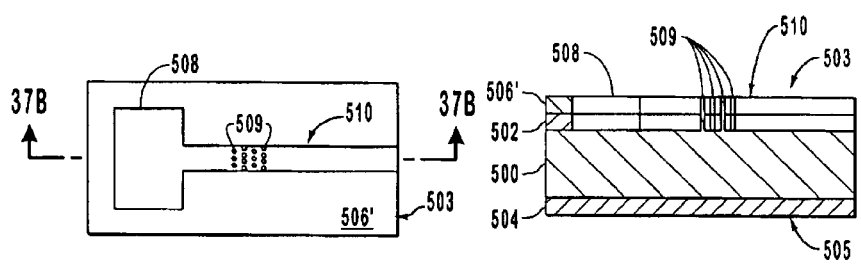

Referring to the plan and cross-sectional views, respectively, of FIGS. 37A and 37B, after development of the photoresist 506, the exposed areas 508, 509, 510 of the photoresist corresponding to the reservoir, separation posts and channel, respectively, are removed and open to the underlying silicon dioxide layer 502 while the unexposed areas remain protected by photoresist 506'. The exposed areas 508, 509, 510 of the silicon dioxide layer 502 are then etched by a fluorine-based plasma with a high degree of anisotropy and selectivity to the protective photoresist 506' until the silicon separation substrate 500 is reached. The remaining photoresist is removed in an oxygen plasma or in an actively oxidizing chemical bath like sulfuric acid ($H_2SO_4$) activated with hydrogen peroxide ($H_2O_2$).

Figure 38:
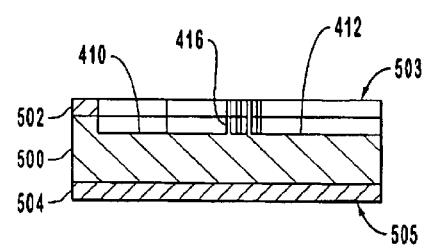

As shown in the cross-sectional view of FIG. 38, the reservoir 410, the separation channel 412, and the separation posts 416 in the separation channel 412 are vertically formed in the silicon separation substrate 500 by another fluorine-based etch. Preferably, the reservoir 410 and the separation channel 412 have the same depth controlled by the etch time at a known etch rate. The simultaneous formation of the reservoir 410 and the channel 412 ensures uniform depth such that there are no discontinuities in the fluid-constraining surfaces to impede the fluid flow. The depth of the reservoir 410 and the channel 412 is preferably between approximately 5–20 $\mu$m and more preferably approximately 10 $\mu$m. The etch can reliably and reproducibly be executed to produce an aspect ratio (etch depth to width) of up to 30:1. Although not shown, any other reservoirs and/or channels, populated or unpopulated, may also be formed by this etch sequence.

A film of positive-working photoresist is then deposited over the silicon dioxide layer 502 and the exposed separation substrate 500 on the reservoir side 503 of the separation substrate 500. An area of the photoresist corresponding to the introduction channel which will be subsequently etched is selectively exposed through a mask by an optical lithographic exposure tool passing short-wavelength light, such as blue or near-ultraviolet at wavelengths of 365, 405, or 436 nanometers. After development of the photoresist, the exposed area of the photoresist corresponding to the introduction channel is removed and open to the underlying separation substrate 500 while the unexposed areas remain protected by the photoresist.

Figure 39A:
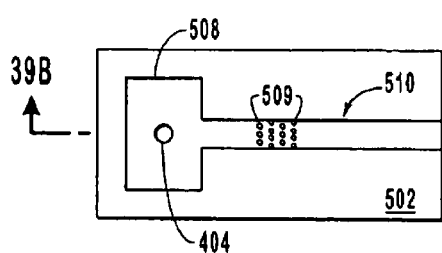
Figure 39B:
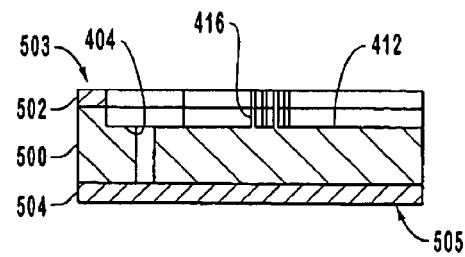

As shown in the plan and cross-sectional views of FIGS. 39A and 39B, respectively, the exposed area of the separation substrate 500 is then vertically etched by a fluorine-based plasma with a high degree of anisotropy and selectivity to the protective photoresist until the silicon dioxide layer 504 on back side 505 is reached. Thus, a portion of the introduction channel 404 is formed through the separation substrate 500. The remaining photoresist is removed in an oxygen plasma or in an actively oxidizing chemical bath like sulfuric acid ($H_2SO_4$) activated with hydrogen peroxide ($H_2O_2$). The silicon dioxide layer 504 on the back side 505 may then be removed by, for example, an unpatterned etch in a fluorine-based plasma.

Figure 40A:
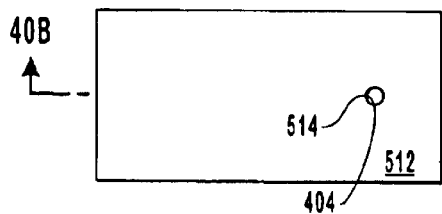
Figure 40B:
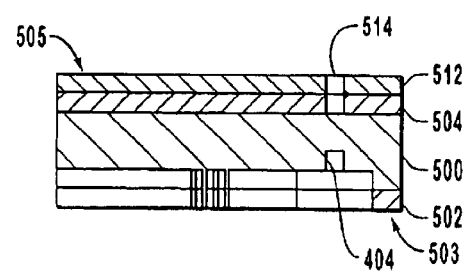
Figure 41:
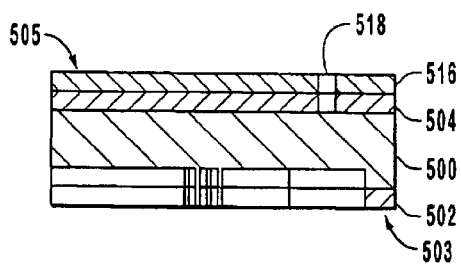

Alternatively, as shown in FIGS. 40A and 40B, the introduction channel 404 may be formed by etching from both the reservoir side 503 and the back side 505 of the substrate 500. After performing a vertical etch though a portion of the substrate 500 to form a portion of the introduction channel 404 in a manner similar to that described above, a film of positive-working photoresist 512 is deposited on the silicon dioxide layer 504 on the back side 505 of the separation substrate 500. Patterns on the back side 505 may be aligned to those previously formed on the reservoir side 503 of the separation substrate 500. Because silicon and its oxide are inherently relatively transparent to light in the infrared wavelength range of the spectrum, i.e. approximately 700–1000 nanometers, the extant pattern on the reservoir side 503 can be distinguished with sufficient clarity by illuminating the separation substrate 500 from the patterned reservoir side 503 with infrared light. Thus, the mask for the back side 505 can be aligned within required tolerances. Upon alignment, an area of the photoresist 512 corresponding to the entrance orifice and the introduction channel which will be subsequently etched is selectively exposed through a mask by an optical lithographic exposure tool passing short-wavelength light, such as blue or near-ultraviolet at wavelengths of 365, 405, or 436 nanometers.

After development of the photoresist 512, the exposed area 514 of the photoresist corresponding to the entrance orifice is removed to expose the underlying silicon dioxide layer 504 on the back side 505 of the separation substrate 500 while the unexposed areas remain protected by the photoresist 512. The exposed area 514 of the silicon dioxide layer 504 is then etched by a fluorine-based plasma with a high degree of anisotropy and selectivity to the protective photoresist 512 until the substrate 500 is reached. The remaining photoresist provides additional masking during a subsequent fluorine-based silicon etch to vertically etch the backside portion of the introduction channel. Thus, a through-substrate introduction channel 404 is complete. The remaining photoresist is removed in an oxygen plasma or in an actively oxidizing chemical bath like sulfuric acid ($H_2SO_4$) activated with hydrogen peroxide ($H_2O_2$).

Preferably, the introduction channel 404 has the same diameter as the entrance orifice. A practical limit on etch aspect ratio of 30:1 constrains the diameter of the entrance orifice being etched to be approximately 10 $\mu$m or greater for substrates of approximately 300 $\mu$m thickness. Preferably, the entrance orifice 406 and the introduction channel 404 are approximately 100 $\mu$m in diameter due to practical considerations. For example, the etch aspect ratio imposes a minimum diameter, and the diameter is preferably sufficiently large to enable ease of filling the reservoir 410 yet sufficiently small to ensure a fluid surface tension to prevent the fluid from leaking out of the reservoir 410.

Alternatively, both the introduction channel and the entrance orifice may be formed by etching from the back side 505 of the separation substrate 500. This may be preferable as it may be difficult to satisfactorily coat the separation posts 416 with photoresist. Further, this may be desirable depending on the application of the device, e.g. the external sample delivery system, the desired chip handling devices, the interfacing with other devices, chip-based or non-chip based, and/or the packaging considerations of the chip. Referring to the cross-sectional view of FIG. 41, after the reservoir, separation channel and the separation posts are etched in the separation substrate 500 (shown in FIG. 38), a film of positive-working photoresist 516 is deposited on the silicon dioxide layer 504 on the back side 505 of the separation substrate 500. Patterns on the back side 505 may be aligned to those previously formed on the reservoir side 503 of the separation substrate 500 by illuminating the separation substrate 500 from the patterned reservoir side 503 with infrared light, as described above. Upon alignment, an area of the photoresist 516 corresponding to the entrance orifice which will be subsequently etched is selectively exposed through a mask by an optical lithographic exposure tool passing short-wavelength light, such as blue or near-ultraviolet at wavelengths of 365, 405, or 436 nanometers.

After development of the photoresist 516, the exposed area 518 of the photoresist 516 corresponding to the entrance orifice is removed to expose the underlying silicon dioxide layer 504 on the back side 505 of the separation substrate 500. The exposed area 518 of the silicon dioxide layer 504 is then etched by a fluorine-based plasma with a high degree of anisotropy and selectivity to the protective photoresist 512 until the silicon separation substrate 500 is reached. The remaining photoresist is left in place to provide additional masking during the subsequent etch through the silicon separation substrate 500.

Figure 42:
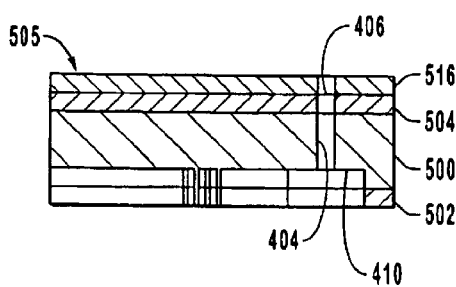

Referring now to the cross-sectional view of FIG. 42, the introduction channel 404 is vertically formed through the silicon separation substrate 500 by another fluorine-based etch. The introduction channel 404 is completed by etching through the separation substrate 500 until the reservoir 410 is reached. Thus, the introduction channel 404 extends through the separation substrate 500 between the entrance orifice 406 on the back side 505 of the separation substrate 500 and the reservoir 410. The remaining photoresist is removed in an oxygen plasma or in an actively oxidizing chemical bath like sulfuric acid ($H_2SO_4$) activated with hydrogen peroxide ($H_2O_2$)

Oxidation for Surface Passivation and Fluid Isolation

Figure 43:
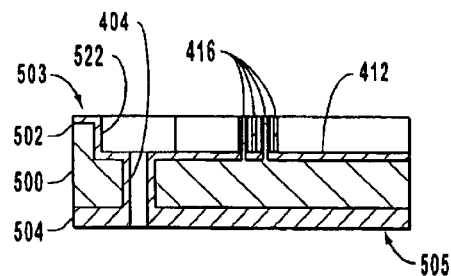

As shown in the cross-sectional view of FIG. 43, a layer of silicon dioxide 522 is grown on all silicon surfaces of the substrate 500 by subjecting the silicon substrate 500 to elevated temperature in an oxidizing ambient. For example, the oxidizing ambient may be an ultra-pure steam produced by oxidation of hydrogen for a silicon dioxide thickness greater than approximately several hundred nanometers or pure oxygen for a silicon dioxide thickness of approximately several hundred nanometers or less. The layer of silicon dioxide 522 over all silicon surfaces of the separation substrate 500 electrically isolates a fluid in the channel from the silicon substrate 500 and permits the application and sustenance of an electric potential difference between the reservoir and the exit of the separation channel, between the reservoir and an unpopulated portion of the separation channel near the reservoir to facilitate in filling the reservoir and/or between other points along the fluid flow path. Thus, the application and sustenance of a significant voltage across the fluid sample may be achieved. Further, oxidation renders a surface inactive relative to a bare silicon surface, resulting in surface passivation.

All silicon surfaces are oxidized to form silicon dioxide with a thickness that is controllable through choice of temperature and time of oxidation. The final thickness of the silicon dioxide can be selected to provide the desired degree of electrical isolation in the device, where a thicker layer of silicon dioxide provides a greater resistance to electrical breakdown.

Photolithography and reactive-ion etching limit the layout design of separation post diameters and inter-post spacing to greater than approximately 1 $\mu$m. However, because the thermal oxidation process consumes approximately 0.44 $\mu$m of silicon to form each micrometer of silicon dioxide, the thermal oxidation process results in a volumetric expansion. This volumetric expansion may be utilized to reduce the spacing between the separation posts 416 to sub-micrometer dimensions. For example, with a layout inter-post spacing of approximately 1.5 $\mu$m, oxidation producing a 1 $\mu$m silicon dioxide film or layer would result in a nearest-neighbor spacing of approximately 0.5 $\mu$m. Further, because the oxidation process is well-controlled, separation post dimensions, including the inter-post spacing, in the sub-micrometer regime can be formed reproducibly and in a high yielding manner.

Figure 44A:
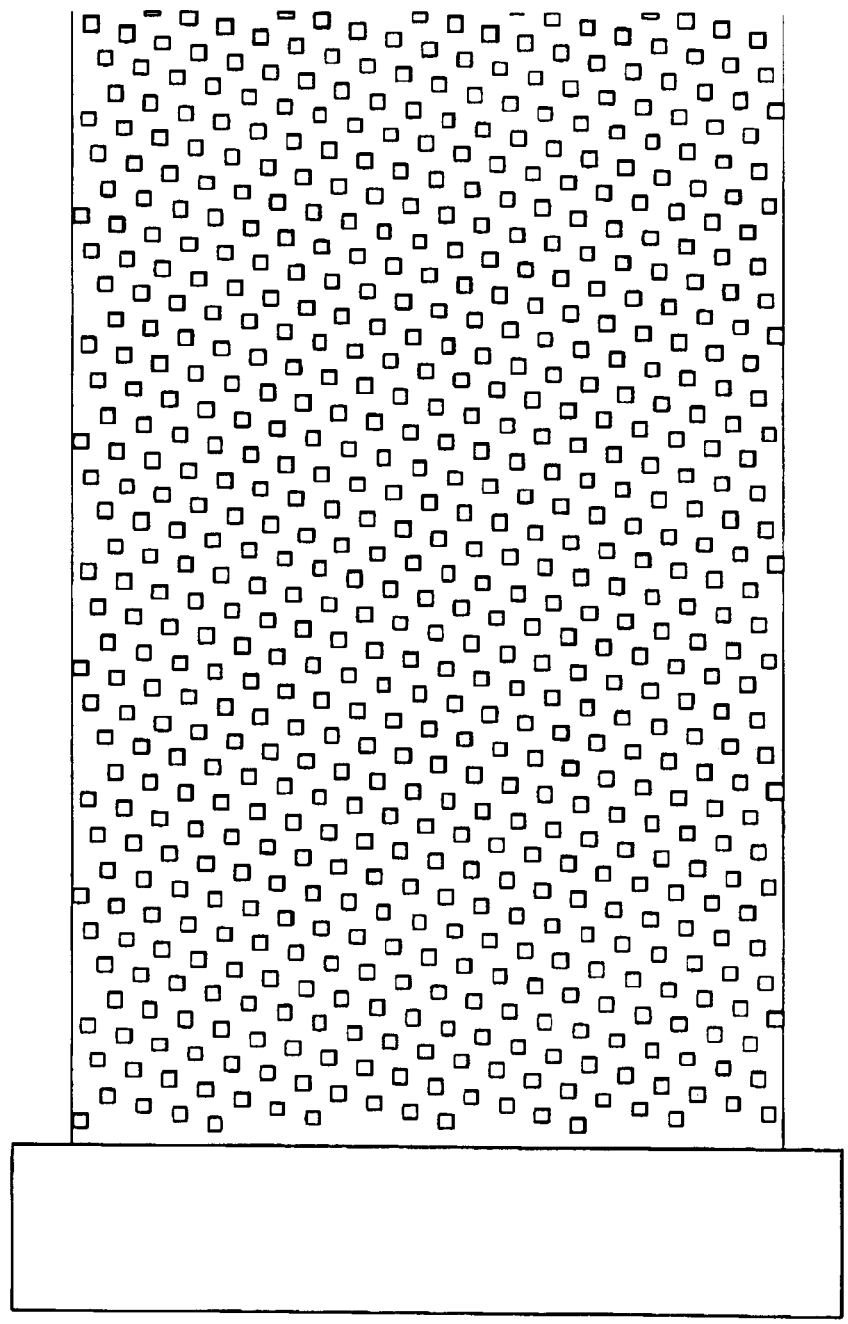
Figure 44B:
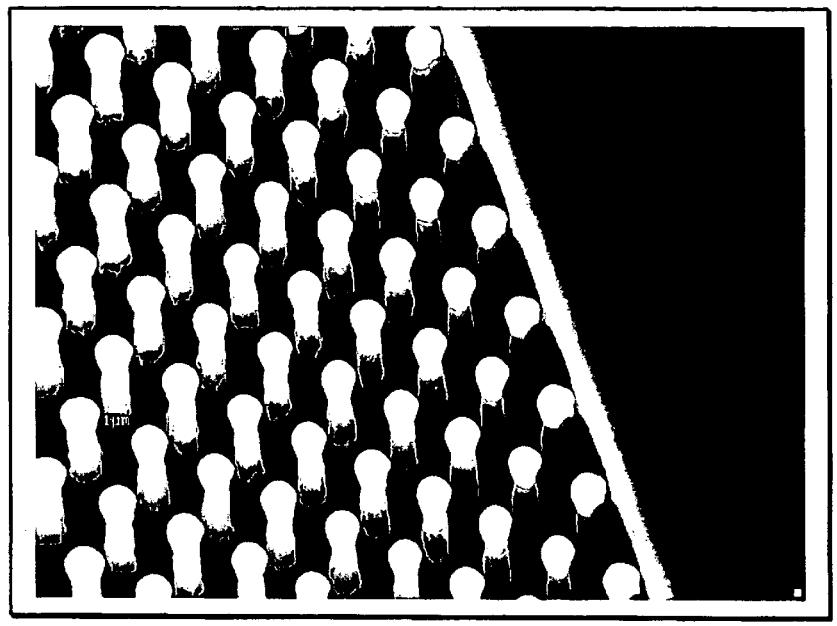
Figure 44C:
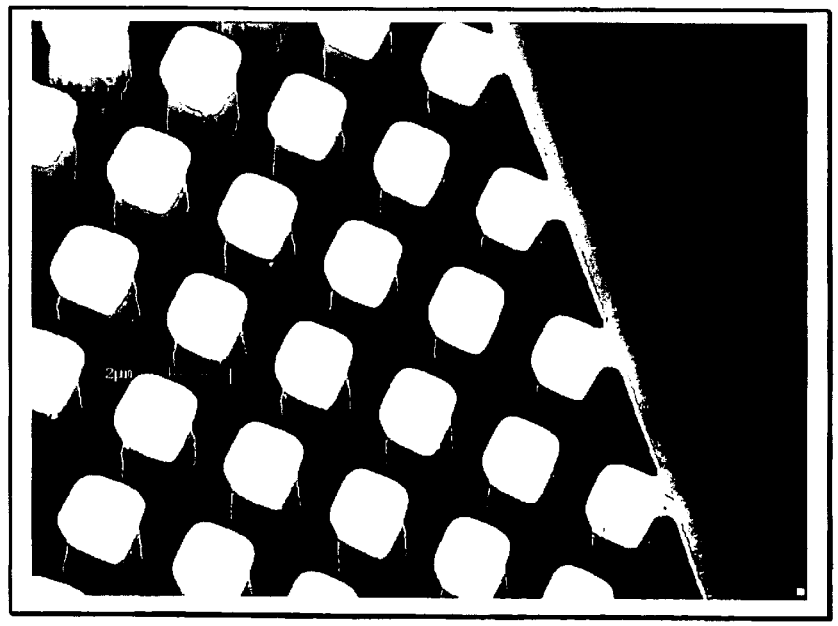

FIGS. 44A, 44B and 44C show scanning electron microscope photographs and design layout of portions of fabricated liquid chromatography devices. FIG. 44A shows a design layout of a portion of a reservoir and separation posts in a portion of a separation channel where the separation posts have rectangular cross-sectional shape. FIG. 44B shows separation posts in a portion of a separation channel, the separation posts having a circular cross-sectional shape and a diameter and inter-post spacing of approximately 1 $\mu$m. FIG. 44C shows separation posts in a portion of a separation channel, the separation posts having a rectangular or square cross-sectional shape with a dimension of 2 $\mu$m and inter-post spacing of approximately 1 $\mu$m.

Figure 45:
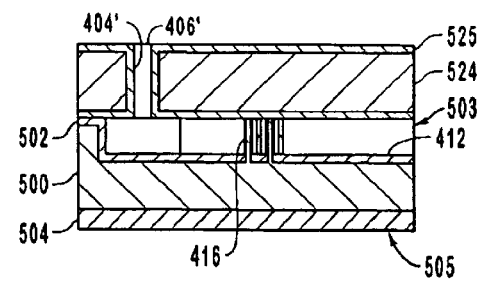

In a variation, the entrance orifice and the introduction channel for filling the fluid reservoir may be formed in the cover substrate 524 after a layer of silicon dioxide 525 is grown on all surfaces of the cover substrate 524, rather than in the substrate 500. As shown in FIG. 45, the cover substrate 524 may be bonded to the reservoir side 503 of the separation substrate 500. The entrance orifice 406' and the introduction channel 404' may be formed in the cover substrate 524 after alignment with respect to the reservoir 410. The entrance orifice 406' and the introduction channel 404' may be formed in the same or similar manner as described above by utilizing lithography to define the entrance orifice pattern and reactive-ion etching to create the entrance orifice and the through-cover introduction channel. The cover substrate 524 is again subjected to elevated temperature in an oxidizing ambient to grow a layer of oxide on the surface of the introduction channel 404'. Further, the introduction channel 404' may be formed from one or two sides of the cover substrate 524. If channel 404' is formed from two sides of the cover substrate, the cover substrate 524 may be bonded to substrate 500 after forming the channel 404' and after oxidation of the channel surface. One advantage of defining the entrance orifice on the same side of the completed liquid chromatography device as the reservoir and separation channel is that the back side of the substrate 500 is then free from any features and may then be bonded to a protective package without special provision for filling the reservoir through an entrance orifice defined on the back-side of the substrate.

Metallization for Fluid Flow Control

Figure 46A:
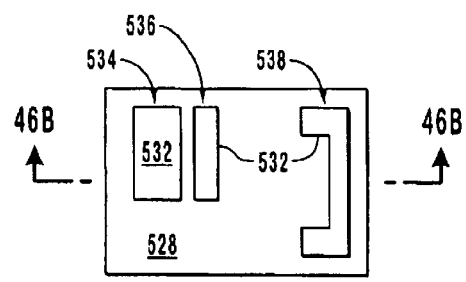
Figure 46B:
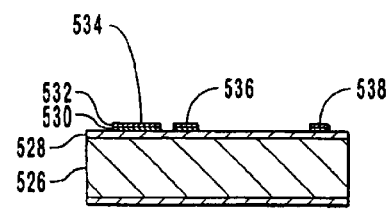

FIGS. 46A and 46B illustrate the formation of a reservoir, a filling, and an exit electrode as well as conductive lines or wires connecting the electrodes to bond pads in the cover substrate 526, preferably comprising glass and/or silicon. The cover substrate 526 shown in FIGS. 46A and 46B does not provide an entrance orifice or an introduction channel although the metallization process described herein may be easily adapted for a cover substrate providing an entrance orifice and an introduction channel.

As shown in the plan and cross-sectional view of FIGS. 46A and 46B, respectively, prior to the depositing of conductive material on the cover substrate 526, all surfaces of the cover substrate 526 are subjected to thermal oxidization in a manner that is the same as or similar to the process described above to create a film or layer of silicon dioxide 528. Such oxidization is not performed where the cover substrate 526 comprises glass.

The silicon dioxide layer 528 provides a surface on which conductive electrodes may be formed. The thickness of the silicon dioxide layer 528 is controllable through the oxidation temperature and time and the final thickness can be selected to provide the desired degree of electrical isolation, where a thicker layer of silicon dioxide provides a greater resistance to electrical breakdown. The silicon dioxide layer 528 electrically isolates all electrodes from the cover substrate 526 and isolates the fluid in the reservoir and the channel of the liquid chromatography device from the cover substrate 526. The ability to isolate the fluid from the cover substrate 526 complements the electrical isolation provided in the separation substrate through oxidation and ensures the complete electrical isolation of the fluid from both the separation substrate and the cover substrate 526. The complete electrical isolation of the sample fluid from both substrates allows for the application of electric potential differences between spatially separated locations in the fluidic flow path resulting in control of the fluid flow through the path.

The cover substrate 528 may be cleaned after oxidation utilizing an oxidizing solution such as an actively oxidizing chemical bath, for example, sulfuric acid ($H_2SO_4$) activated with hydrogen peroxide ($H_2O_2$). The cover substrate 528 is then thoroughly rinsed to eliminate organic contaminants and particulates. A layer of conductive material 530 such as aluminum is then deposited by any suitable method such as by DC magnetron sputtering in an argon ambient. The thickness of the aluminum is preferably approximately 3000 Å, although shown having a larger thickness for clarity. Although aluminum is utilized in the fabrication sequence described herein, any type of highly conductive material such as other metals, metallic multi-layers, silicides, conductive polymers, and conductive ceramics like indium tin oxide (ITO) may be utilized for the electrodes. The surface preparation for satisfactory adhesion may vary depending on the specific electrode material used. For example, the silicon dioxide layer 528 provides a surface to which aluminum electrodes may adhere as aluminum does not generally adhere well to native silicon.

A film of positive-working photoresist 532 is then deposited over the surface of the conductive material 530. Areas of the photoresist layer 532 corresponding to areas surrounding the electrodes (shown) and conductive lines or wires and bond pads which will be subsequently etched are selectively exposed through a mask by an optical lithographic exposure tool passing short-wavelength light, such as blue or near-ultraviolet at wavelengths of 365, 405, or 436 nanometers.

After development of the photoresist 532, the exposed areas of the photoresist are removed, leaving opening to the underlying aluminum conductive layer 530 while the unexposed areas 534, 536, 538 corresponding to the reservoir, filling and exit electrodes, respectively, as well as conductive lines or wires and bond pads remain protected by the photoresist. The conductive electrodes and the lines/bond pads may be etched, such as by a wet chemical etch or a reactive-ion etch, as appropriate for the particular conductive material. The etch is selective to the underlying silicon dioxide layer 528 or is terminated upon reaching the silicon dioxide layer 528 as determined by the etch time and rate. The remaining photoresist is removed in an oxygen plasma or in a solvent bath such as acetone. The fabrication sequence thus results in physically and electrically separate islands of conductive electrodes, lines and bond pads according to the pattern designed in the mask.

Figure 46C:
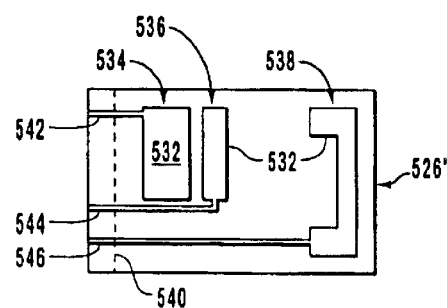

The cover substrate may be larger than the separation substrate to allow access to the bond pads and/or directly to the electrodes for the application of potential voltage(s) to the electrode(s). As shown in FIG. 46C, the cover substrate 526' is larger than the separation substrate such that the separation substrate only extends to dashed line 540 relative to the cover substrate 526'. Conductive lead-throughs such as connecting metal lines 542, 544 and 546 extend from the reservoir, filling and exit electrodes, 534, 536, 538, respectively, and enable the application of potential voltage(s) to the electrode(s).

Alternatively, a metal lead may be formed from each electrode to an otherwise unpatterned area of the separation substrate such that a through-substrate access channel formed in the cover substrate and filled with a conductive material by chemical vapor deposition (CVD) allows access to the electrode(s). As an alternative to chemical vapor deposition, the sidewalls of the through-substrate access channel may be sloped, for example by KOH etch, to facilitate continuous deposition of a conductive material thereon, thereby providing an electrically continuous path from the separation substrate to the top of the cover substrate where potential voltages can be applied. In these variations, the separation and the cover substrates may be of the same size.

Although the electrodes are preferably provided on a surface of the cover substrate, the electrodes may be alternatively and/or additionally provided on the separation substrate by appropriate modifications to the above-described fabrication process. For example, in such a variation, the side walls of the reservoir are preferably not at a 90° angle relative to the bottom wall and can be formed at least in part by, for example, a wet chemical potassium hydroxide (KOH) etch. The sloped reservoir side walls allow for the deposition of a conductive material thereon. In another variation, the electrodes may also be formed by a damascene process, known in the art of semiconductor fabrication. The damascene process provides the advantage of a planar surface without the step up and step down surface topography presented by a bond line or pad and thus facilitates the bonding of the separation and cover substrate, as described below.

The above described fabrication sequence for the liquid chromatography device may be easily adapted to and is applicable for the simultaneous fabrication of a monolithic system comprising multiple liquid chromatography devices including multiple reservoirs and/or multiple separation channels as described above embodied in a single monolithic substrate.

Further, although the fabrication sequence is described in terms of fabricating a single liquid chromatography device, the fabrication sequence facilitates and allows for massively parallel processing of similar devices. The multiple liquid chromatography devices or systems fabricated by massively parallel processing on a single wafer may then be cut or otherwise separated into multiple devices or systems.

Although control of the liquid chromatography device has been described above as comprising reservoir, filling and exit electrodes, any suitable combination of such and/or other electrodes in electrical contact with the fluid in the fluid path may be provided and easily fabricated by modifying the layout design. Further, any or all of the electrodes may be additionally or alternatively provided in the separation substrate. Electrodes may be formed in the separation substrate by modifying the fabrication sequence to include additional steps similar to or the same as the steps as described above with respect to the formation of the electrodes in the cover substrate.

Bonding Cover Substrate to Separation Substrate

As described above, the cover substrate is preferably hermetically bonded by any suitable method to the separation substrate for containment and isolation of the fluid in the liquid chromatography device. Examples of bonding silicon to silicon or glass to silicon include anodic bonding, sodium silicate bonding, eutectic bonding, and fusion bonding.

For example, to bond the separation substrate to a glass cover substrate by anodic bonding, the separation substrate and cover substrate are heated to approximately 400° C. and a voltage of 400–1200 Volts is applied, with the separation substrate chosen as the anode (the higher potential). Further, as the required bonding voltage depends on the surface oxide thickness, it may be desirable to remove the oxide film or layer from the back side 505 of the separation substrate prior to the bonding process in order to reduce the required bonding voltage. The oxide film or layer may be removed by, for example, an unpatterned etch in a fluorine-based plasma. The etch is continued until the entire oxide layer has been removed, and the degree of over-etch is unimportant. Thus, the etch is easily controlled and high-yielding.

Critical considerations in any of the bonding methods include the alignment of features in the separation and the cover substrates to ensure proper functioning of the liquid chromatography device after bonding and the provision in layout design for conductive lead-throughs such as the bond pads and/or metal lines so that the electrodes (if any) are accessible from outside the liquid chromatography device. Another critical consideration is the topography created through the fabrication sequence which may compromise the ability of the bonding method to hermetically seal the separation and cover substrates. For example, the step up and step down in the surface topography presented by a metal line or pad may be particularly difficult to form a seal therearound as the silicon or glass does not readily deform to conform to the shape of the metal line or pad, leaving a void near the interface between the metal and the oxide.

Integration of Liquid Chromatography and Electrospray Devices on a Chip

Figure 47:
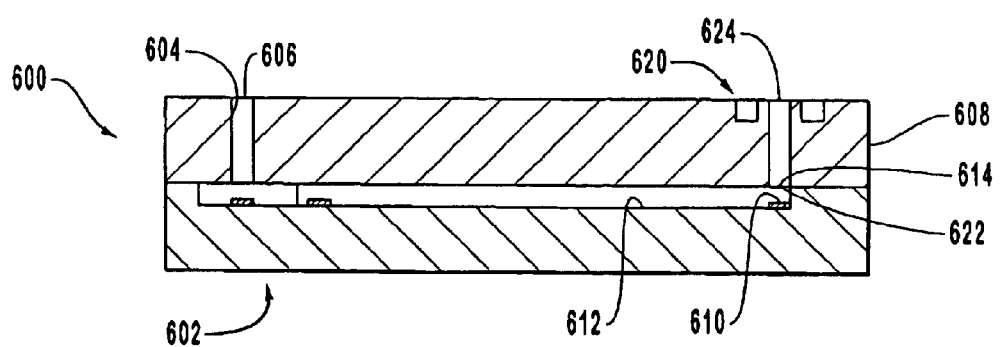
FIG. 47 shows a cross-sectional view of a system comprising a liquid chromatography device homogenously integrated with an electrospray device.

The cross-sectional schematic view of FIG. 47 shows a liquid chromatography-electrospray system 600 comprising a liquid chromatography device 602 of the present invention integrated with an electrospray device 620 of the present invention such that a homogeneous interface is formed between the exit orifice 614 of the liquid chromatography device 602 and the entrance orifice 622 of the electrospray device 620. The single integrated system 600 allows for the fluid exiting the exit orifice 614 of the liquid chromatography device 602 to be delivered on-chip to the entrance orifice 622 of the electrospray device 620 in order to generate an electrospray.

As shown in FIG. 47, the entrance orifice 606 and the introduction channel 604 of the liquid chromatography device 602 are formed in the cover substrate 608 along with the electrospray device 620. Alternatively, the liquid chromatography entrance orifice and the introduction channel may be formed in the separation substrate.

Fluid at the electrospray nozzle entrance 622 is at the exit voltage applied to the exit electrode 610 in the separation channel 612 near the liquid chromatography exit orifice 614. Thus, an electrospray entrance electrode is not necessary.

The single integrated system 600 provides the advantage of minimizing or eliminating extra fluid volume to reduce the risk of undesired fluid changes, such as by reactions and/or mixing. The single integrated system 600 also provides the advantage of eliminating the need for unreliable handling and attachment of components at the microscopic level and of minimizing or eliminating fluid leakage by containing the fluid within one integrated system.

The integrated liquid chromatography-electrospray system 600 may be utilized to deliver liquid samples to the sampling orifice of a mass spectrometer. The sampling orifice of the mass spectrometer may serve as an extraction electrode in the electrospray process when held at an appropriate voltage relative to the voltage of the electrospray nozzle 624. The liquid chromatography-electrospray system 600 may be positioned within 10 mm of the sampling orifice of the mass spectrometer for efficient extraction of the fluid from the electrospray nozzle 624.

Multiple Liquid Chromatography-Electrospray Systems on a Single Chip

Figure 48:
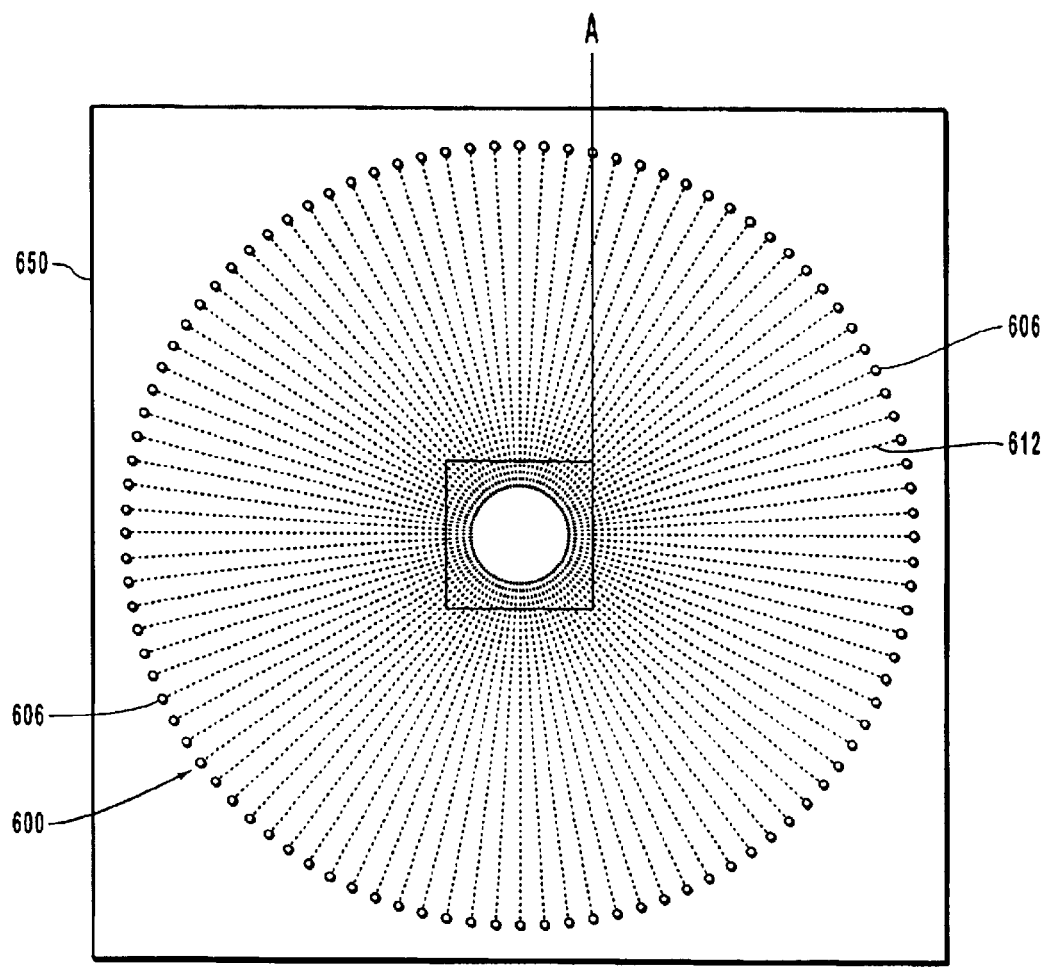
FIG. 48 shows a plan view of the system of FIG. 47.
Figure 49:
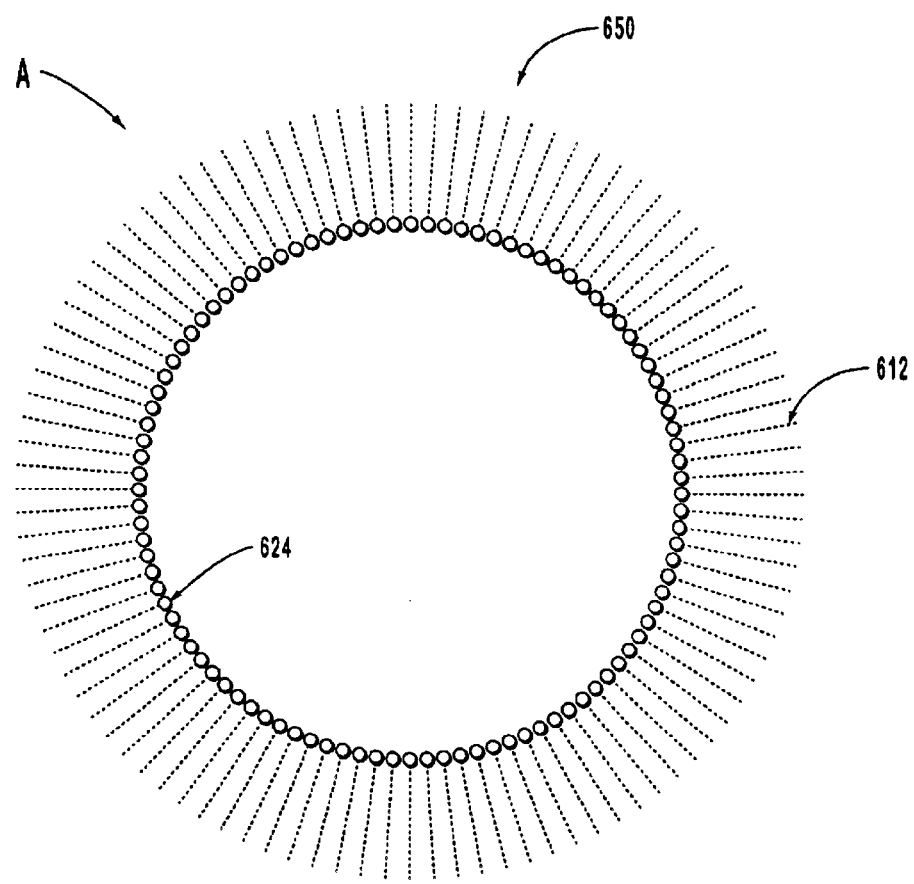
FIG. 49 shows a detailed view of the nozzles of the system of FIG. 47.

Multiples of the liquid chromatography-electrospray system 600 may be formed on a single chip to deliver a multiplicity of samples to a common point for subsequent sequential analysis. For example, FIG. 48 shows a plan view of multiple liquid chromatography-electrospray systems 600 on a single chip 650 and FIG. 49 shows a detailed view of area A of systems 600 with the separation channels shown in phantom and without the recessed portions for purposes of clarity. As shown, the multiple nozzles 624 of the electrospray devices 620 may be radially positioned about a circle having a relatively small diameter near the center of the single chip 650. The dimensions of the electrospray nozzles and the liquid chromatography channels limit the radius at which multiple nozzles are positioned on the multi-system chip 650. For example, the multi-system chip may provide 96 nozzles with widths of up to 50 $\mu$m positioned around a circle 2 mm in diameter such that the spacing between each pair of nozzles is approximately 65 $\mu$m.

Alternatively, an array of multiple electrospray devices without liquid chromatography devices may be formed on a single chip to deliver a multiplicity of samples to a common point for subsequent sequential analysis. The nozzles may be similarly radially positioned about a circle having a relatively small diameter near the center of the chip. The array of electrospray devices on a single microchip may be integrated upstream with multiple fluid delivery devices such as separation devices fabricated on a single microchip. For example, an array of radially distributed exit orifices of a radially distributed array of micro liquid chromatography columns may be integrated with radially distributed entrance orifices of electrospray devices such that the nozzles are arranged at a small radius near the orifice of a mass spectrometer. Thus, the electrospray devices may be utilized for rapid sequential analysis of multiple sample fluids. However, depending upon the specific application and/or the capabilities of the downstream mass spectrometer (or other downstream device), the multiples of the electrospray devices may be utilized one at a time or simultaneously, either all or a portion of the electrospray devices, to generate one or more electrosprays. In other words, the multiples of the electrospray devices may be operated in parallel, staggered or individually.

The single multi-system chip 650 may be fabricated entirely in silicon substrates, thereby taking advantage of well-developed silicon processing techniques described above. Such processing techniques allow the single multi-system chip 650 to be fabricated in a cost-effective manner, resulting in a cost performance that is consistent with use as a disposable device to eliminate cross-sample contamination. Furthermore, because the dimensions and positions of the liquid chromatography-electrospray systems are determined through layout design rather than through processing, the layout design may be easily adapted to fabricate multiple liquid chromatography-electrospray systems on a single chip.

Interface of a Multi-System Chip to Mass Spectrometer

The radially distributed array of electrospray nozzles 624 on a multi-system chip may be interfaced with a sampling orifice of a mass spectrometer by positioning the nozzles near the sampling orifice. The tight radial configuration of the electrospray nozzles 624 allows the positioning thereof in close proximity to the sampling orifice of a mass spectrometer.

The multi-system chip 650 may be rotated relative to the sampling orifice to position one or more of the nozzles for electrospray near the sampling orifice. Appropriate voltage (s) may then be applied to the one or more of the nozzles for electrospray. Alternatively, the multi-system chip 650 may be fixed relative to the sampling orifice of a mass spectrometer such that all nozzles, which converge in a relatively tight radius, are appropriately positioned for the electrospray process. As is evident, eliminating the need for nozzle repositioning allows for highly reproduced and quick alignment of the single multi-system chip and increases the speed of the analyses.

One, some or all the radially distributed nozzles 624 of the electrospray devices may generated electrosprays simultaneously, sequentially or randomly as controlled by the voltage applied to the appropriate electrodes of the electrospray device 620.

While specific and preferred embodiments of the invention have been described and illustrated herein, it will be appreciated that modifications can be made without departing from the spirit of the invention as found in the appended claims.

What is claimed is:

1. An electrospray device comprising:
    a. a substrate;
    b. a first channel communicating at one end with an exit orifice at a surface of the substrate;
    c. a recess formed in the surface of the substrate so as to surround said first channel, thereby forming a nozzle from which an electrospray may be emitted.

2. The device of claim 1, further comprising a plurality of additional channels communicating at one end with an exit orifice of the same surface of the substrate as that of the first channel so as to form a planar array of channels; each channel having a recess formed in the surface of the substrate so as to form a nozzle from which an electrospray may be emitted.

3. The device of claim 1, wherein the substrate is monolithic.

4. The device of claim 1, wherein the substrate is monolithic silicon.

5. The device of claim 1, wherein the cross-sectional area of the nozzle is less than 50,000 square micrometers.

* * * * *